US007863422B2

(12) United States Patent
Clark et al.

(10) Patent No.: US 7,863,422 B2
(45) Date of Patent: Jan. 4, 2011

(54) ANTI-PRO87299 ANTIBODIES

(75) Inventors: Hilary Clark, San Francisco, CA (US); Daniel L. Eaton, San Rafael, CA (US); Bernd Wranik, South San Francisco, CA (US); Wenjun Ouyang, Foster City, CA (US); Lino Gonzalez, Hollister, CA (US); Austin L. Gurney, San Francisco, CA (US); Kelly Loyet, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 108 days.

(21) Appl. No.: 12/180,427

(22) Filed: Jul. 25, 2008

(65) Prior Publication Data

US 2009/0022713 A1    Jan. 22, 2009

Related U.S. Application Data

(60) Division of application No. 10/987,663, filed on Nov. 12, 2004, now Pat. No. 7,479,544, which is a continuation-in-part of application No. 10/371,341, filed on Feb. 19, 2003, now Pat. No. 7,153,950.

(60) Provisional application No. 60/421,236, filed on Oct. 25, 2002.

(51) Int. Cl.
 *C07K 16/00* (2006.01)
(52) U.S. Cl. .................................... 530/387.1
(58) Field of Classification Search ........................ None
 See application file for complete search history.

(56) References Cited

U.S. PATENT DOCUMENTS

| 5,364,934 | A | 11/1994 | Drayna et al. |
| 6,569,992 | B1 | 5/2003 | LaFleur et al. |
| 7,153,950 | B2 | 12/2006 | Clark et al. |
| 7,479,544 | B2 * | 1/2009 | Clark et al. ............. 530/387.1 |
| 2004/0175380 | A1 | 9/2004 | Allison et al. |
| 2007/0161061 | A1 | 7/2007 | Clark et al. |
| 2009/0081229 | A1 | 3/2009 | Clark et al. |
| 2009/0175855 | A1 | 7/2009 | Clark et al. |

FOREIGN PATENT DOCUMENTS

| EP | 1 033 401 A2 | 9/2000 |
| JP | 2001-269182 | 10/2001 |
| JP | 2002-502589 | 1/2002 |
| WO | WO 99/40100 | 8/1999 |
| WO | WO 01/10482 | 2/2001 |
| WO | WO 01/75166 | 10/2001 |
| WO | 02/070706 A2 | 9/2002 |
| WO | WO 02/072794 | 9/2002 |
| WO | 2004/039394 A1 | 5/2004 |
| WO | 2004/101756 A2 | 11/2004 |
| WO | 2005/113003 A2 | 12/2005 |
| WO | 2006/054961 A2 | 5/2006 |
| WO | 2006/063067 A2 | 6/2006 |
| WO | 2007/001459 A2 | 1/2007 |

OTHER PUBLICATIONS

Altschul and Gish, "Local Alignment Statistics" *Methods in Enzymology* 266:460-480 (1996).
Attwood, Teresa K., "The Babel of Bioinformatics" *Science* 290:471-473 (2000).
Bolton, C.,, "Recent advances in the pharmacological control of experimental allergic encephalomyelitis (EAE) and the implications for multiple sclerosis treatment" *Multiple Sclerosis*. 1:143-149 (1995).
Carfi et al., "Herpes Simplex Virus Glycoprotein D Bound to the Human Receptor HveA" *Molecular Cell* 8:169-179 (Jul. 2001).
Chen et al., "Selection and Analysis of an Optimized Anti-VEGF Antibody: Crystal Structure of an Affinity-matured Fab in Complex with Antigen" *Journal of Molecular Biology* 293(4):865-881 (1999).
Cheung et al., "Evolutionarily divergent herpesviruses modulate T cell activation by targeting the herpresvirus entry mediator cosignaling pathway" *Proc. Natl. Acad. Sci. USA* 102:13218-13223 (2005).
Coligan et al., "Proliferative Assays for T Cell Function" *Current Protocols in Immunology*, John Wiley & Sons, Inc., Chapter 3.12, vol. 1 (1991).
Compaan et al., "Attenuating Lymphocyte Activity, The Crystal Structure of the BTLA-HVEM Complex" *The Journal of Biological Chemistry* 280:39553-39561 (2005).
Croft, Michael, "The evolving crosstalk between co-stimulatory and co-inhibitory receptors: HVEM-BTLA" *Trends in Immunology* 26:292-294 (2005).
Deppong et al, "Cutting Edge: B and T Lymphocyte Attenuator are Programmed Death Receptor-1 Inhibitory Receptors are Required for Termination of Acute Allergic Airway Inflammation" *Journal of Immunology* 176:3909-3913 (2006).
Gavrieli et al., "BTLA and HVEM Cross Talk Regulates Inhibition and Costimulation" *Advances in Immunology* 92:157-185 (2006).
Gonzalez et al., "A coreceptor interaction between the CD28 and TNF receptor family members B and T lymphocyte attenuator and herpesvirus entry mediator" *Proc. Natl. Acad. Sci. USA* 102:1116-1121 (2005).
Hakim et al., "Animal Models of Acute and Chronic Graft-Versus-Host Disease" *Current Protocols in Immunology* (unit 4.3, supplement 27), J E Coligan, A M Kruisbeek, D H Marglies, E M Shev, John Wiley & Sons, Inc (1998).
Hurchla et al, "B and T Lymphocyte Attenuator Exhibits Structural and Expression Polymorphisms and Is Highly Induced in Anergic CD4+ T Cells" *Journal of Immunology* 174:3377-3385 (2005).
Marsters et al., "Identification of a Ligand for the Death-Domain-Containing Receptor Apo3" *Current Biology* 8(9):525-528 (1998).
Mauri et al., "LIGHT, a new member of the TNF superfamily, and lymphotoxin α are ligands for herpesvirus entry mediator" *Immunity* 8(1):21-30 (Jan. 1998).
Metzler et al., "Solution structure of human CTLA-4 and delineation of a CD80/CD86 binding site conserved in CD28" *Nature Structural Biol.* 4(7):527-531 (Jul. 1997).

(Continued)

*Primary Examiner*—Ilia Ouspenski
(74) *Attorney, Agent, or Firm*—Danielle M. Pasqualone

(57) ABSTRACT

The present invention relates to compositions containing a novel protein and methods of using those compositions for the diagnosis and treatment of immune related disease.

12 Claims, 34 Drawing Sheets

OTHER PUBLICATIONS

Milne et al., "Function of Herpes Simplex Virus Type 1 gD Mutants with Different Receptor-Binding Affinities in Virus Entry and Fusion" *Journal of Virology* 77 (16) :8962-8972 (Aug. 2003).

Montgomery et al., "Herpes Simplex Virus-1 Entry into Cells Mediated by a Novel Member of the TNF/NGF Receptor Family" *Cell* 87(3) :427-436 (1996).

Murphy et al., "Balancing co-stimulation and inhibition with BTLA and HVEM" *Nature Reviews/Immunology* 6:671-681 (2006).

Sagawa et al., "The Protein-tyrosine Phosphatase SHP-2 Associates with Tyrosine-Phosphorylated Adhesion Molecule PECAM-1 (CD31)" *Journal of Biological Chemistry* 272(49) :31086-31091 (Dec. 5, 1997).

Sarrias et al., "The Three HveA Receptor Ligands, gD, LT-α and LIGHT Bind to Distinct Sites on HveA" *Molecular Immunology* 37:665-673 (2000).

Sedy et al., "B and T lymphocyte attenuator regulates T cell activation through interaction with herpesvirus entry mediator" *Nature Immunology* 6:90-98 (2005).

Skolnick et al., "From Genes to protein structure and function: novel applications of computational approahces in the genomic era" *TIBTECH* 18:34-39 (Jan. 2000).

Tao et al., "Differential Effects of B and T Lymphocyte Attenuator and Programmed Death-1 on Acceptance of Partially versus Fully MHC-Mismatched Cardiac Allografts" *Journal of Immunology* 175:5774-5782 (2005).

Watanabe N., et al.,, "BTLA is a Lymphocyte Inhibitory Receptor with Similarities to CTLA-4 and PD-1" *Nature Immunology* 4(7) : 670-679 (Jul. 2003).

Williams et al., "The immunoglobulin superfamily—domains for cell surface recognition" *Ann. Rev. Immunol.* 6:381-405 (1988).

Costello et al, "Stimulation of non-Hodgkin's lymphoma via HVEM: an alternate and safe way to increase Fas-induced apoptosis and improve tumor immunogenicity" *Leukemia* 17:2500-2507 (2003).

Notice of Rejection (translation) mailed Nov. 13, 2008, in JP Application No. 2004-548251.

PCT International Search Report and Written Opinion of the International Searching Authority, mailed Nov. 7, 2008, for PCT International Application No. PCT/US2008/056765, filed Mar. 13, 2008.

Vendel et al., "B and T Lymphocyte Attenuator Regulates B Cell Receptor Signaling by Targeting Syk and BLNK" *The Journal of Immunology* 182:1509-1517 (2009).

\* cited by examiner

CCTCGGTTCTATCGATTGAATTCATGAAGACATTGCCTGCCATGCTTGGAACTGGGAAAT
TATTTTGGGTCTTCTTCTTAATCCCATATCTGGACATCTGGAACATCCATGGGAAAGAAT
CATGTGATGTACAGCTTTATATAAAGAGACAATCTGAACACTCCATCTTAGCAGGAGATC
CCTTTGAACTAGAATGCCCTGTGAAATACTGTGCTAACAGGCCTCATGTGACTTGGTGCA
AGCTCAATGGAACAACATGTGTAAAACTTGAAGATAGACAAACAAGTTGGAAGGAAGAGA
AGAACATTTCATTTTTCATTCTACATTTTGAACCAGTGCTTCCTAATGACAATGGGTCAT
ACCGCTGTTCTGCAAATTTTCAGTCTAATCTCATTGAAAGCCACTCAACAACTCTTTATG
TGACAGATGTAAAAAGTGCTTCAGAACGACCCTCCAAGGACGAAATGGCAAGCAGACCCT
GGCTCCTGTATAGTTTACTTCCTTTGGGGGGATTGCCTCTACTCATCACTACCTGTTTCT
GCCTGTTCTGCTGCCTGAGAAGGCACCAAGGAAAGCAAAATGAACTCTCTGACACAGCAG
GAAGGGAAATTAACCTGGTTGATGCTCACCTTAAGAGTGAGCAAACAGAAGCAAGCACCA
GGCAAAATTCCCAAGTACTGCTATCAGAAACTGGAATTTATGATAATGACCCTGACCTTT
GTTTCAGAATGCAGGAAGGGTCTGAAGTTTATTCTAATCCATGCCTGGAAGAAAACAAAC
CAGGCATTGTTTATGCTTCCCTGAACCATTCTGTCATTGGACTGAACTCAAGACTGGCAA
GAAATGTAAAAGAAGCACCAACAGAATATGCATCCATATGTGTGAGGAGTTAAGGATCCT
CTAGAGTCGACCTGCAGAAGCTTGGCCGCCATGGCCCAACTTGTTTATTGCAGCTTATAA
GTGTTACAAATAAACAAATAATATTTCTCAATTTGAGAATTTTTACTTTAGAAATGTTCA
TGTTAGTGCTTGGGTCTGAAGGGTCCATAGGACAAATGATTAAAAT

FIG. 1

MKTLPAMLGTGKLFWVFFLIPYLDIWNIHGKESCDVQLYIKRQSEHSILAGDPFELECPV
KYCANRPHVTWCKLNGTTCVKLEDRQTSWKEEKNISFFILHFEPVLPNDNGSYRCSANFQ
SNLIESHSTTLYVTDVKSASERPSKDEMASRPWLLYSLLPLGGLPLLITTCFCLFCCLRR
HQGKQNELSDTAGREINLVDAHLKSEQTEASTRQNSQVLLSETGIYDNDPDLCFRMQEGS
EVYSNPCLEENKPGIVYASLNHSVIGLNSRLARNVKEAPTEYASICVRS

Signal sequence
none

Transmembrane domain
153-173

N-glycosylation site.
    75-78
    94-97
   110-113
   261-264 cAMP- and cGMP-dependent protein kinase phosphorylation site.
    41-44

Tyrosine kinase phosphorylation site.
    31-39

N-myristoylation site.
   111-116
   224-229
   254-259

ITIM domain
255-260

ITISM domain
280-285

Immunoglobulin domain
51-117

FIG. 2

GCCGCAGCAATGGCGCTGAGTTCCTCTGCTGGAGTTCATCCTGCTAGCTGGGTTCCCGAG
CTGCCGGTCTGAGCCTGAGGCATGGAGCCTCCTGGAGACTGGGGGCCTCCTCCCTGGAGA
TCCACCCCCAGAACCGACGTCTTGAGGCTGGTGCTGTATCTCACCTTCCTGGGAGCCCCC
TGCTACGCCCCAGCTCTGCCGTCCTGCAAGGAGGACGAGTACCCAGTGGGCTCCGAGTGC
TGCCCCAAGTGCAGTCCAGGTTATCGTGTGAAGGAGGCCTGCGGGGAGCTGACGGGCACA
GTGTGTGAACCCTGCCCTCCAGGCACCTACATTGCCCACCTCAATGGCCTAAGCAAGTGT
CTGCAGTGCCAAATGTGTGACCCAGCCATGGGCCTGCGCGCGAGCCGGAACTGCTCCAGG
ACAGAGAACGCCGTGTGTGGCTGCAGCCCAGGCCACTTCTGCATCGTCCAGGACGGGGAC
CACTGCGCCGCGTGCCGCGCTTACGCCACCTCCAGCCCGGGCCAGAGGGTGCAGAAGGGA
GGCACCGAGAGTCAGGACACCCTGTGTCAGAACTGCCCCCCGGGGACCTTCTCTCCCAAT
GGGACCCTGGAGGAATGTCAGCACCAGACCAAGTGCAGCTGGCTGGTGACGAAGGCCGGA
GCTGGGACCAGCAGCTCCCACTGGGTATGGTGGTTTCTCTCAGGGAGCCTCGTCATCGTC
ATTGTTTGCTCCACAGTTGGCCTAATCATATGTGTGAAAAGAAGAAAGCCAAGGGGTGAT
GTAGTCAAGGTGATCGTCTCCGTCCAGCGGAAAAGACAGGAGGCAGAAGGTGAGGCCACA
GTCATTGAGGCCCTGCAGGCCCCTCCGGACGTCACCACGGTGGCCGTGGAGGAGACAATA
CCCTCATTCACGGGGAGGAGCCCAAACCACTGACCCACAGACTCTGCACCCCGACGCCAG
AGATACCTGGAGCGACGGCTGCTGAAAGAGGCTGTCCACCTGGCGAAACCACCGGAGCCC
GGAGGCTTGGGGGCTCCGCCCTGGGCTGG

FIG. 3

MEPPGDWGPPPWRSTPRTDVLRLVLYLTFLGAPCYAPALPSCKEDEYPVGSECCPKCSPG
YRVKEACGELTGTVCEPCPPGTYIAHLNGLSKCLQCQMCDPAMGLRASRNCSRTENAVCG
CSPGHFCIVQDGDHCAACRAYATSSPGQRVQKGGTESQDTLCQNCPPGTFSPNGTLEECQ
HQTKCSWLVTKAGAGTSSSHWVWWFLSGSLVIVIVCSTVGLIICVKRRKPRGDVVKVIVS
VQRKRQEAEGEATVIEALQAPPDVTTVAVEETIPSFTGRSPNH

Signal sequence
    1-36

Transmembrane domain
    201-221

N-glycosylation site.

110-114
    173-177

N-myristoylation site.

81-87
    89-95
    104-110
    120-126
    153-159
    193-199
    195-201
    220-226

Cell attachment sequence.

231-234

TNFR/NGFR cysteine-rich region 42-75
    78-119

FIG. 4

GGTTTCCTCTGAGGTTGAAGGACCCAGGCGTGTCAGCCCTGCTCCAGACACCTTGGGCAT
GGAGGAGAGTGTCGTACGGCCCTCAGTGTTTGTGGTGGATGGACAGACCGACATCCCATT
CACGAGGCTGGGACGAAGCCACCGGAGACAGTCGTGCAGTGTGGCCCGGGTGGGTCTGGG
TCTCTTGCTGTTGCTGATGGGGGCCGGGCTGGCCGTCCAAGGCTGGTTCCTCCTGCAGCT
GCACTGGCGTCTAGGAGAGATGGTCACCCGCCTGCCTGACGGACCTGCAGGCTCCTGGGA
GCAGCTGATACAAGAGCGAAGGTCTCACGAGGTCAACCCAGCAGCGCATCTCACAGGGGC
CAACTCCAGCTTGACCGGCAGCGGGGGCCGCTGTTATGGGAGACTCAGCTGGGCCTGGC
CTTCCTGAGGGGCCTCAGCTACCACGATGGGGCCCTTGTGGTCACCAAAGCTGGCTACTA
CTACATCTACTCCAAGGTGCAGCTGGGCGGTGTGGGCTGCCCGCTGGGCCTGGCCAGCAC
CATCACCCACGGCCTCTACAAGCGCACACCCCGCTACCCCGAGGAGCTGGAGCTGTTGGT
CAGCCAGCAGTCACCCTGCGGACGGGCCACCAGCAGCTCCCGGGTCTGGTGGGACAGCAG
CTTCCTGGGTGGTGTGGTACACCTGGAGGCTGGGGAGGAGGTGGTCGTCCGTGTGCTGGA
TGAACGCCTGGTTCGACTGCGTGATGGTACCCGGTCTTACTTCGGGGCTTTCATGGTGTG
AAGGAAGGAGCGTGGTGCATTGGACATGGGTCTGACACGTGGAGAACTCAGAGGGTGCCT
CAGGGGAAAGAAAACTCACGAAGCAGAGGCTGGGCGTGGTGGCTCTCGCCTGTAATCCCA
GCACTTTGGGAGGCCAAGGCAGGCGGATCACCTGAGGTCAGGAGTTCGAGACCAGCCTGG
CTAACATGGCAAAACCCCATCTCTACTAAAAATACAAAAATTAGCCGGACGTGGTGGTGC
CTGCCTGTAATCCAGCTACTCAGGAGGCTGAGGCAGGATAATTTTGCTTAAACCCGGGAG
GCGGAGGTTGCAGTGAGCCGAGAṪCACACCACTGCACTCCAACCTGGGAAACGCAGTGAG
ACTGTGCCTCAAAAAAAAG

FIG. 5

MEESVVRPSVFVVDGQTDIPFTRLGRSHRRQSCSVARVGLGLLLLLMGAGLAVQGWFLLQ
LHWRLGEMVTRLPDGPAGSWEQLIQERRSHEVNPAAHLTGANSSLTGSGGPLLWETQLGL
AFLRGLSYHDGALVVTKAGYYYIYSKVQLGGVGCPLGLASTITHGLYKRTPRYPEELELL
VSQQSPCGRATSSSRVWWDSSFLGGVVHLEAGEEVVVRVLDERLVRLRDGTRSYFGAFMV

Signal sequence
    None

Transmembrane domain
    None

N-glycosylation site.
    102-106 cAMP- and cGMP-dependent protein kinase phosphorylation site.
    29-33

N-myristoylation site.
    48-54
    100-106
    153-159
    157-163

Leucine zipper pattern.
    44-66
    51-73

FIG. 6

ATGAAGACATTGCCTGCCATGCTTGGAACTGGGAAATTATTTTGGGTCTTCTTCTTAATC
CCATATCTGGACATCTGGAACATCCATGGGAAAGAATCATGTGATGTACAGCTTTATATA
AAGAGACAATCTGAACACTCCATCTTAGCAGGAGATCCCTTTGAACTAGAATGCCCTGTG
AAATACTGTGCTAACAGGCCTCATGTGACTTGGTGCAAGCTCAATGGAACAACATGTGTA
AAACTTGAAGATAGACAAACAAGTTGGAAGGAAGAGAAGAACATTTCATTTTTCATTCTA
CATTTTGAACCAGTGCTTCCTAATGACAATGGGTCATACCGCTGTTCTGCAAATTTTCAG
TCTAATCTCATTGAAAGCCACTCAACAACTCTTTATGTGACAGGAAAGCAAAATGAACTC
TCTGACACAGCAGGAAGGGAAATTAACCTGGTTGATGCTCACCTTAAGAGTGAGCAAACA
GAAGCAAGCACCAGGCAAAATTCCCAAGTACTGCTATCAGAAACTGGAATTTATGATAAT
GACCCTGACCTTTGTTTCAGGATGCAGGAAGGGTCTGAAGTTTATTCTAATCCATGCCTG
GAAGAAAACAAACCAGGCATTGTTTATGCTTCCCTGAACCATTCTGTCATTGGACTGAAC
TCAAGACTGGCAAGAAATGTAAAAGAAGCACCAACAGAATATGCATCCATATGTGTGAGG
AGTTAA

FIG. 7

MKTLPAMLGTGKLFWVFFLIPYLDIWNIHGKESCDVQLYIKRQSEHSILAGDPFELECPV
KYCANRPHVTWCKLNGTTCVKLEDRQTSWKEEKNISFFILHFEPVLPNDNGSYRCSANFQ
SNLIESHSTTLYVTGKQNELSDTAGREINLVDAHLKSEQTEASTRQNSQVLLSETGIYDN
DPDLCFRMQEGSEVYSNPCLEENKPGIVYASLNHSVIGLNSRLARNVKEAPTEYASICVRS

Signal sequence
None

Transmemebrane domain
None

N-glycosylation site.
    75-79
    94-98
    110-114
    213-217 cAMP- and cGMP-dependent protein kinase phosphorylation site.
    41-45

Tyrosine kinase phosphorylation site.
    31-40

N-myristoylation site.
    111-117
    176-182
    206-212

Immunoglobulin domain
    51-117

ITIM domain
207-212

ITISM domain
232-237

FIG. 8

ATGAAGACATTGCCTGCCATGCTTGGAACTGGGAAATTATTTTGGGTCTTCTTCTTAATC
CCATATCTGGACATCTGGAACATCCATGGGAAAGAATCATGTGATGTACAGCTTTATATA
AAGAGACAATCTGAACACTCCATCTTAGCAGGAGATCCCTTTGAACTAGAATGCCCTGTG
AAATACTGTGCTAACAGGCCTCATGTGACTTGGTGCAAGCTCAATGGAACAACATGTGTA
AAACTTGAAGATAGACAAACAAGTTGGAAGGAAGAGAAGAACATTTCATTTTTCATTCTA
CATTTTGAACCAGTGCTTCCTAATGACAATGGGTCATACCGCTGTTCTGCAAATTTTCAG
TCTAATCTCATTGAAAGCCACTCAACAACTCTTTATGTGACAGCATTTACTAACATTCCA
GATGTAAAAAGTGCCTCAGAACGACCCTCCAAGGACGAAATGGCAAGCAGACCCTGGCTC
CTGTATAGTTTACTTCCTTTGGGGGGATTGCCTCTACTCATCACTACCTGTTTCTGCCTG
TTCTGCTGCCTGAGAAGGCACCAAGGAAAGCAAAATGAACTCTCTGACACAGCAGGAAGG
GAAATTAACCTGGTTGATGCTCACCTTAAGAGTGAGCAAACAGAAGCAAGCACCAGGCAA
AATTCCCAAGTACTGCTATCAGAAACTGGAATTTATGATAATGACCCTGACCTTTGTTTC
AGGATGCAGGAAGGGTCTGAAGTTTATTCTAATCCATGCCTGGAAGAAAACAAACCAGGC
ATTGTTTATGCTTCCCTGAACCATTCTGTCATTGGACTGAACTCAAGACTGGCAAGAAAT
GTAAAAGAAGCACCAACAGAATATGCATCCATATGTGTGAGGAGTTAA

FIG. 9

MKTLPAMLGTGKLFWVFFLIPYLDIWNIHGKESCDVQLYIKRQSEHSILAGDPFELECPV
KYCANRPHVTWCKLNGTTCVKLEDRQTSWKEEKNISFFILHFEPVLPNDNGSYRCSANFQ
SNLIESHSTTLYVTAFTNIPDVKSASERPSKDEMASRPWLLYSLLPLGGLPLLITTCFCL
FCCLRRHQGKQNELSDTAGREINLVDAHLKSEQTEASTRQNSQVLLSETGIYDNDPDLCF
RMQEGSEVYSNPCLEENKPGIVYASLNHSVIGLNSRLARNVKEAPTEYASICVRS

Signal sequence
None

Transmembrane domain
158-178

N-glycosylation site.
    75-79
    94-98
    110-114
    267-271 cAMP- and cGMP-dependent protein kinase phosphorylation site.
    41-45

Tyrosine kinase phosphorylation site.
    31-40

N-myristoylation site
    111-117
    230-236
    260-266

ITIM domain
261-266

ITISM domain
286-291

FIG. 10

```
1012-25     1 ------------------ATGCTTGGAACTGGGAAATTATTTTGGGTCTT 32
1013-35     1 ------------------ATGCTTGGAACTGGGAAATTATTTTGGGTCTT 32
1020-40     1 ------------------ATGCTTGGAACTGGGAAATTATTTTGGGTCTT 32
1072-45     1 ------------------ATGCTTGGAACTGGGAAATTATTTTGGGTCTT 32
1075-49     1 ------------------ATGCTTGGAACTGGGAAATTATTTTGGGTCTT 32
1075-51     1 ------------------ATGCTTGGAACTGGGAAATTATTTTGGGTCTT 32
1076-59     1 ATGAAGACATTGCCTGCCATGCTTGGAACTGGGAAATTATTTTGGGTCTT 50
1077-62     1 ------------------ATGCTTGGAACTGGGAATTTATTTTGGGTCTT 32
1086-67     1 ------------------ATGCTTGGAACTGGGAAATTATTTTGGGTCTT 32
1086-69     1 ATGAAGACATTGCCTGCCATGCTTGGAACTGGGAAATTATTTTGGGTCTT 50
 330-8      1 ------------------ATGCTTGGAACTGGGAAATTATTTTGGGTCTT 32
1013-34     1 ------------------ATGCTTGGAACTGGGAAATTATTTTGGGTCTT 32
1020-38     1 ATGAAGACATTGCCTGCCATGCTTGGAACTGGGAAATTATTTTGGGTCTT 50
1072-47     1 ------------------ATGCTTGGAACTGGGAAATTATTTTGGGTCTT 32
1076-58     1 -----------------CATGCTTGGAACTGGGAAATTATTTTGGGTCTT 33
1077-61     1 ------------------ATGCTTGGAACTGGGGAATTATTTTGGGTCTT 32
1096-75     1 ATGAAGACATTGCCTGCCATGCTTGGAACTGGGAAATTATTTTGGGTCTT 50
1112-95     1 ATGAAGACATTGCCTGCCATGCTTGGAACTGGGAAATTATTTTGGGTCTT 50
 310-4      1 ------------------ATGCTTGGAACTGGGAAATTATTTTGGGTCTT 32
 362-14     1 ------------------ATGCTTGGAACTGGGAAATTATTTTGGGTCTT 32
 330-10SE   1 ------------------ATGCTTGGAACTGGGAAATTATTTTGGGTCTT 32
 362-13     1 ATGAAGACATTGCCTGCCATGCTTGGAACTGGGAAATTATTTTGGGTCTT 50
1098-83SE   1 ATGAAGACATTGCCTGCCATGCTTGGAACTGGGAAATTATTTTGGGTCTT 50

1012-25    33 CTTCTTAATCCCATATCTGGACATCTGGAACATCCATGGGAAAGAATCAT 82
1013-35    33 CTTCTTAATCCCATATCTGGACATCTGGAACATCCATGGGAAAGAATCAT 82
1020-40    33 CTTCTTAATCCCATATCTGGACATCTGGAACATCCATGGGAAAGAATCAT 82
1072-45    33 CTTCTTAATCCCATATCTGGACATCTGGAACATCCATGGGAAAGAATCAT 82
1075-49    33 CTTCTTAATCCCATATCTGGACATCTGGAACATCCATGGGAAAGAATCAT 82
1075-51    33 CTTCTTAATCCCATATCTGGACATCTGGAACATCCATGGGAAAGAATCAC 82
1076-59    51 CTTCTTAATCCCATATCTGGACATCTGGAACATCCATGGGAAAGAATCAT 100
1077-62    33 CTTCTTAATCCCATATCTGGACATCTGGAACATCCATGGGAAAGAATCAT 82
1086-67    33 CTTCTTAATCCCATATCTGGACATCTGGAACATCCATGGGAAAGAATCAT 82
1086-69    51 CTTCTTAATCCCATATCTGGACATCTGGAACATCCATGGGAAAGAATCAT 100
 330-8     33 CTTCTTAATCCCATATCTGGACATCTGGAACATCCATGGGAAAGAATCAT 82
1013-34    33 CTTCTTAATCCCATATCTGGACATCTGGAACATCCATGGGAAAGAATCAT 82
1020-38    51 CTTCTTAATCCCATATCTGGACATCTGGAACATCCATGGGAAAGAATCAT 100
1072-47    33 CTTCTTAATCCCATATCTGGACATCTGGAACATCCATGGGAAAGAATCAT 82
1076-58    34 CTTCTTAATCCCATATCTGGACATCTGGAACATCCATGGGAAAGAATCAT 83
1077-61    33 CTTCTTAATCCCATATCTGGACATCTGGAACATCCATGGGAAAGAATCAT 82
1096-75    51 CTTCTTAATCCCATATCTGGACATCTGGAACATCCATGGGAAAGAATCAT 100
1112-95    51 CTTCTTAATCCCATATCTGGACATCTGGAACATCCATGGGAAAGAATCAT 100
 310-4     33 CTTCTTAATCCCATATCTGGACATCTGGAACATCCATGGGAAAGAATCAT 82
 362-14    33 CTTCTTAATCCCATATCTGGACATCTGGAACATCCATGGGAAAGAATCAT 82
 330-10SE  33 CTTCTTAATCCCATATCTGGACATCTGGAACATCCATGGGAAAGAATCAT 82
 362-13    51 CTCCTTAATCCCATATCTGGACATCTGGAACATCCATGGGAAAGAATCAT 100
1098-83SE  51 CTTCTTAATCCCATATCTGGACATCTGGAACATCCATGGGAAAGAATCAT 100
```

FIG. 11A

```
1012-25     83  GTGATGTACAGCTTTATATAAAGAGACAATCTGAACACTCCATCTTAGCA 132
1013-35     83  GTGATGTACAGCTTTATATAAAGAGACAATCTGAACACTCCATCTTAGCA 132
1020-40     83  GTGATGTACAGCTTTATATAAAGAGACAATCTGAACACTCCATCTTAGCA 132
1072-45     83  GTGATGTACAGCTTTATATAAAGAGACAATCTGAACACTCCATCTTAGCA 132
1075-49     83  GTGATGTACAGCTTTATATAAAGAGACAATCTGAACACTCCATCTTAGCA 132
1075-51     83  GTGATGTACAGCTTTATATAAAGAGACAATCTGAACATTCCATCTTAGCA 132
1076-59    101  GTGATGTACAGCTTTATATAAAGAGACAATCTGAACACTCCATCTTAGCA 150
1077-62     83  GTGATGTACAGCTTTATATAAAGAGACAATCTGAACACTCCATCTTAGCA 132
1086-67     83  GTGATGTACAGCTTTATATAAAGAGACAATCTGAACACTCCATCTTAGCA 132
1086-69    101  GTGATGTACAGCTTTATATAAAGAGACAATCTGAACACTCCATCTTAGCA 150
 330-8      83  GTGATGTACAGCTTTATATAAAGAGACAATCTGAACACTCCATCTTAGCA 132
1013-34     83  GTGATGTACAGCTTTATATAAAGAGACAATCTGAACACTCCATCTTAGCA 132
1020-38    101  GTGATGTACAGCTTTATATAAAGAGACAATCTGAACACTCCATCTTAGCA 150
1072-47     83  GTGATGTACAGCTTTATATAAAGAGACAATCTGAACACTCCATCTTAGCA 132
1076-58     84  GTGATGTACAGCTTTATATAAAGAGTCAATCTGAACACTCCATCTTAGCA 133
1077-61     83  GTGATGTACAGCTTTATATAAAGCGACAATCTGAACACTCCATCTTAGCA 132
1096-75    101  GTGATGTACAGCTTTATATAAAGAGACAATCTGAACACTCCATCTTAGCA 150
1112-95    101  GTGATGTACAGCTTTATATAAAGAGACAATCTGAACACTCCATCTTAGCA 150
 310-4      83  GTGATGTACAGCTTTATATAAAGAGACAATCTGAACACTCCATCTTAGCA 132
 362-14     83  GTGATGTACAGCTTTATATAAAGAGACAATCTGAACACTCCATCTTAGCA 132
 330-10SE   83  GTGATGTACAGCTTTATATAAAGAGACAATCTGAACACTCCATCTTAGCA 132
 362-13    101  GTGATGTACAGCTTTATATAAAGAGACAATCTGAACACTCCATCTTAGCA 150
1098-83SE  101  GTGATGTACAGCTTTATATAAAGAGACAATCTGAACACTCCATCTTAGCA 150

1012-25    133  GGAGATCCCTTTGAACTAGAATGCCCTGTGAAATACTGTGCTAACAGGCC 182
1013-35    133  GGAGATCCCTTTGAACTAGAATGCCCTGTGAAATACTGTGCTAACAGGCC 182
1020-40    133  GGAGATCCCTTTGAACTAGAATGCCCTGTGAAATACTGTGCTAACAGGCC 182
1072-45    133  GGAGATCCCTTTGAACTAGAATGCCCTGTGAAATACTGTGCTAACAGGCC 182
1075-49    133  GGAGATCCCTTTGAACTAGAATGCCCTGTGAAATACTGTGCTAACAGGCC 182
1075-51    133  GGAGATCCCTTTGAACTAGAATGCCCTGTGAAATACTGTGCTAACAGGCC 182
1076-59    151  GGAGATCCCTTTGAACTAGAATGCCCTGTGAAATACTGTGCTAACAGGCC 200
1077-62    133  GGAGATCCCTTTGAACTAGAATGCCCTGTGAAATACTGTGCTAACAGGCC 182
1086-67    133  GGAGATCCCTTTGAACTAGAATGCCCTGTGAAATACTGTGCTAACAGGCC 182
1086-69    151  GGAGATCCCTTTGAACTAGAATGCCCTGTGAAATACTGTGCTAACAGGCC 200
 330-8     133  GGAGATCCCTTTGAACTAGAATGCCCTGTGAAATACGGTGCTAACAGGCC 182
1013-34    133  GGAGATCCCTTTGAACTAGAATGCCCTGTGAAATACTGTGCTAACAGGCC 182
1020-38    151  GGAGATCCCTTTGAACTAGAATGCCCTGTGAAATACTGTGCTAACAGGCC 200
1072-47    133  GGAGATCCCTTTGAACTAGAATGCCCTGTGAAATACTGTGCTAACAGGCC 182
1076-58    134  GGAGATCCCTTTGAACTAGAATGCCCTGTGAAATACTGTGCTAACAGGCC 183
1077-61    133  GGAGATCCCTTTGAACTAGAATGCCCTGTGAAATACTGTGCTAACAGGCC 182
1096-75    151  GGAGATCCCTTTGAACTAGAATGCCCTGTGAAATACTGTGCTAACAGGCC 200
1112-95    151  GGAGATCCCTTTGAACTAGAATGCCCTGTGAAATACTGTGCTAACAGGCC 200
 310-4     133  GGAGATCCCTTTGAACTAGAATGCCCTGTGAAATACTGTGCTAACAGGCC 182
 362-14    133  GGAGATCCCTTTGAACTAGAATGCCCTGTGAAATACTGTGCTAACAGGCC 182
 330-10SE  133  GGAGATCCCTTTGAACTAGAATGCCCTGTGAAATACTGTGCTAACAGGCC 182
 362-13    151  GGAGATCCCTTTGAACTAGAATGCCCTGTGAAATACTGTGCTAACAGGCC 200
1098-83SE  151  GGAGATCCCTTTTAACTAGAATGCCCTGTGAAATACTGTGCTAACAGGCC 200
```

FIG. 11B

```
1012-25    183 TCATGTGACTTGGTGCAAGCTCAATGGAACAACATGTGTAAAACTTGAAG 232
1013-35    183 TCATGTGACTTGGTGCAAGCTCAATGGAACAACATGTGTAAAACTTGAAG 232
1020-40    183 TCATGTGACTTGGTGCAAGCTCAATGGAACAACATGTGTAAAACTTGAAG 232
1072-45    183 TCATGTGACTTGGTGCAAGCTCAATGGAACAACATGTGTAAAACTTGAAG 232
1075-49    183 TCATGTGACTTGGTGCAAGCTCAATGGAACAACATGTGTAAAACTTGAAG 232
1075-51    183 TCATGTGACTTGGTGCAAGCTCAATGGAACAACATGTGTAAAACTTGAAG 232
1076-59    201 TCATGTGACTTGGTGCAAGCTCAATGGAACAACATGTGTAAAACTTGAAG 250
1077-62    183 TCATGTGACCTGGTGCAAGCTCAATGGAACAACATGTGTAAAACTTGAAG 232
1086-67    183 TCATGTGACTTGGTGCAAGCTCAATGGAACAACATGTGTAAAACTTGAAG 232
1086-69    201 TCATGTGACTTGGTGCAAGCTCAATGGAACAGCATGTGTAAAACTTGAAG 250
 330-8     183 TCATGTGACTTGGTGCAAGCTCAATGGAACAACATGTGTAAAACTTGGAG 232
1013-34    183 TCATGTGACTTGGTGCAAGCTCAATGGAACAACATGTGTAAAACTTGAAG 232
1020-38    201 TCATGTGACTTGGTGCAAGCTCAATGGAACAACATGTGTAAAACTTGAAG 250
1072-47    183 TCATGTGACTTGGTGCAAGCTCAATGGAACAACATGTGTAAAACTTGAAG 232
1076-58    184 TCATGTGACTTGGTGCAAGCTCAATGGAACAACATGTGTAAAACTTGAAG 233
1077-61    183 TCATGTGACTTGGTGCAAGCTCAATGGAACAACATGTGTAAAACTTGAAG 232
1096-75    201 TCATGTGACTTGGTGCAAGCTCAATGGAACAACATGTGTAAAACTTGAAG 250
1112-95    201 TCATGTGACTTGGTGCAAGCTCAATGGAACAACATGTGTAAAACTTGAAG 250
 310-4     183 TCATGTGACTTGGTGCAAGCTCAATGGAACAACATGTGTAAAACTTGAAG 232
 362-14    183 TCATGTGACTTGGTGCAAGCTCAATGGAACAACATGTGTAAAACTTGAAG 232
330-10SE   183 TCATGTGACTTGGTGCAAGCTCAATGGAACAACATGTGTAAAACTTGAAG 232
 362-13    201 TCATGTGACTTGGTGCAAACTCAATGGAACAACATGTGTAAAACTTGAAG 250
1098-83SE  201 TCATGTGACTTGGTGCAAGCTCAATGGAACAACATGTGTAAAACTTGAAG 250

1012-25    233 ATAGACAAACAAGTTGGAAGGAAGAGAAGAACATTTCATTTTTCATTCTA 282
1013-35    233 ATAGACAAACAAGTTGGAAGGAAGAGAAGAACATTTCATTTTTCATTCTA 282
1020-40    233 ATAGACAAACAAGTTGGAAGGAAGAGAAGAACATTTCATTTTTCATTCTA 282
1072-45    233 ATAGACAAACAAGTTGGAAGGAAGAGAAGAACATTTCATTTTTCATTCTA 282
1075-49    233 ATAGACAAACAAGTTGGAAGGAAGAGAAGAACATTTCATTTTTCATTCTA 282
1075-51    233 ATAGACAAACAAGTTGGAAGGAAGAGAAGAACATTTCATTTTTCATTCTA 282
1076-59    251 ATAGACAAACAAGTTGGAAGGAAGAGAAGAACATTTCATTTTTCATTCTA 300
1077-62    233 ATAGACAAACAAGTTGGAAGGAAGAGAAGAACATTTCATTTTTCATTCTA 282
1086-67    233 ATAGACAAACAAGTTGGAAGGGAGAGAAGAACATTTCATTTTTCATTCTA 282
1086-69    251 ATAGACAAACAAGTTGGAAGGAAGAGAAGAACATTTCATTTTTCATTCTA 300
 330-8     233 ATAGACAAACAAGTTGGAAGGAAGAGAAGAACATTTCATTTTTCATTCTA 282
1013-34    233 ATAGACAAACAAGTTGGAAGGAAGAGAAGAACATTTCATTTTTCATTCTA 282
1020-38    251 ATAGACAAACAAGTTGGAAGGAAGAGAAGAACATTTCATTTTTCATTCTA 300
1072-47    233 ATAGACAAACAAGTTGGAAGGAAGAGAAGAACATTTCATTTTTCATTCTA 282
1076-58    234 ATAGACAAACAAGTTGGAAGGAAGAGAAGAACATTTCATTTTTCATTCTA 283
1077-61    233 ATAGACAAACAAGTTGGAAGGAAGAGAAGAACATTTCATTTTTCATTCTA 282
1096-75    251 ATAGACAAACAAGTTGGAAGGAAGAGAAGAACATTTCATTTTTCATTCTA 300
1112-95    251 ATAGACAAACAAGTTGGAAGGAAGAGAAGAACATTTCATTTTTCATTCTA 300
 310-4     233 ATAGACAAACAAGTTGGAAGGAAGAGAAGAACATTTCATTTTTCATTCTA 282
 362-14    233 ATAGACAAACAAGTTGGAAGGAAGAGAAGAACATTTCATTTTTCATTCTA 282
330-10SE   233 ATAGACAAACAAGTTGGAAGGAAGAGAAGAACATTTCATTTTTCATTCTA 282
 362-13    251 ATAGACAAACAAGTTGGAAGGAAGAGAAGAACATTTCATCTTTCATTCTA 300
1098-83SE  251 ATAGACAAACAAGTTGGAAGGAAGAGAAGAACATTTCATTTTTCATTCTA 300
```

FIG. 11C

```
1012-25    283 CGTTTTGAACCAGTGCTTCCTAATGACAATGGGTCATACCGCTGTTCTGC 332
1013-35    283 CATTTTGAACCAGTGCTTCCTAATGACAATGGGTCATACCGCTGTTCTGC 332
1020-40    283 CATTTTGAACCAGTGCTTCCTAATGACGATGGGTCATACCGCTGTTCTGC 332
1072-45    283 CATTTTGAACCAGTGCTTCCTAATGACAATGGGTCATACCGCTGTTCTGC 332
1075-49    283 CATTTTGAACCAGTGCTTCCTAATGACAATGGGTCATACCGCTGTTCTGC 332
1075-51    283 CATTTTGAACCAGTGCTTCCTAATGACAATGGGTCATACCGCTGTTCTGC 332
1076-59    301 CATTTTGAACCAGTGCTTCCTAATGACAATGGGTCATACCGCTGTTCTGC 350
1077-62    283 CACTTTGAACCAGTGCTTCCTAATGACAATGGGTCATACCGCTGTTCTGC 332
1086-67    283 CATTTTGAACCAGTGCTTCCTAATGACAATGGGTCATACCGCTGTTCTGC 332
1086-69    301 CATTTTGAACCAGTGCTTCCTAATGACAATGGGTCATACCGCTGTTCTGC 350
 330-8     283 CATTTTGAACCAGTGCTTCCTAATGACAATGGGTCATACCGCTGTTCTGC 332
1013-34    283 CATTTTGAACCAGTGCTTCCTAATGACAATGGGTCATACCGCTGTTCTGC 332
1020-38    301 CATTTTGAACCAGTGCTTCCTAATGACAATGGGTCATACCGCTGTTCTGC 350
1072-47    283 CATTTTGAACCAGTGCTTCCTAATGACAATGGGTCATACCGCTGTTCTGC 332
1076-58    284 CATTTTGAACCAGTGCTTCCTAATGACAATGGGTCATACCGCTGTTCTGC 333
1077-61    283 CATTTTGAACCAGCGCTTCCTAATGACAATGGGTCATACCGCTGTTCTGC 332
1096-75    301 CATTTTGAACCAGTGCTTCCTAATGACAATGGGTCATACCGCTGTTCTGC 350
1112-95    301 CATTTTGAACCAGTGCTTCCTAATGACAATGGGTCATACCGCTGTTCTGC 350
 310-4     283 CATTTTGAACCAGTGCTTCCTAATGACAATGGGTCATACCGCTGTTCTGC 332
 362-14    283 CATTTTGAACCAGTGCTTCCTAATGACAATGGGTCATACCGCTGTTCTGC 332
 330-10SE  283 CATTTTGAACCAGTGCTTCCTAATGACAATGGGTCATACCGCTGTTCTGC 332
 362-13    301 CATTTTGAACCAGTGCTTCCTAATGACAATGGGTCATACCGCTGTTCTGC 350
1098-83SE  301 CATTTTGAACCAGTGCTTCCTAATGACAATGGGTCATACCGCTGTTCTGC 350

1012-25    333 AAATTTTCAGTCTAATCTCATTGAAAGCCACTCAACAACTCTTTATGTGA 382
1013-35    333 AAATTTTCAGTCTAATCTCATTGAAAGCCACTCAACAACTCTTTATGTGA 382
1020-40    333 AAATTTTCAGTCTAATCTCATTGAAAGCCACTCAACAACTCTTTATGTGA 382
1072-45    333 AAATTTTCAGTCTAATCTCATTGAAAGCCACTCAACAACTCTTTATGTGA 382
1075-49    333 AAATTTTCAGTCTAATCTCATTGAAAGCCACTCAACAACTCTTTATGTGA 382
1075-51    333 AAATTTTCAGTCTAATCTCATTGAAAGCCACTCAACAACTCTTTATGTGA 382
1076-59    351 AAATTTTCAGTCTAATCTCATTGAAAGCCACTCAACAACTCTTTATGTGA 400
1077-62    333 AAATTTTCAGTCTAATCTCATTGAAAGCCACTCAACAACTCTTTATGTGG 382
1086-67    333 AAATTTTCAGTCTAATCTCATTGAAAGCCACTCAACAACTCTTTATGTGA 382
1086-69    351 AAATTTTCAGTCTAATCTCATTGAAAGCCACTCAACAACTCTTTATGTGA 400
 330-8     333 AAATTTTCAGTCTAATCTCATTGAAAGCCACTCAACAACTCTTTATGTGA 382
1013-34    333 AAATTTTCAGTCTAATCTCATTGAAAGCCACTCAACAACTCTTTATGTGA 382
1020-38    351 AAATTTTCAGTCTAATCTCATTGAAAGCCACTCAACAACTCTTTATGTGA 400
1072-47    333 AAATTTTCAGTCTAATCTCATTGAAAGCCACTCAACAACTCTTTATGTGA 382
1076-58    334 AAATTTTCAGTCTAATCTCATTGAAAGCCACTCAACAACTCTTTATGTGA 383
1077-61    333 AAATTTTCAGTCTAATCTCATTGAAAGCCACTCAACAACTCTTTATGTGA 382
1096-75    351 AAATTTTCAGTCTAATCTCATTGAAAGCCACTCAACAACTCTTTACGTGA 400
1112-95    351 AAATTTTCAGTCTAATCTCATTGAAAGCCACTCAACAACTCTTTATGTGA 400
 310-4     333 AAATTTTCAGTCTAATCTCATTGAAAGCCACTCAACAACTCTTTATGTGA 382
 362-14    333 AAATTTTCAGTCTAATCTCATTGAAAGCCACTCAACAACTCTTTATGTGA 382
 330-10SE  333 AAATTTTCAGTCTAATCTCATTGAAAGCCACTCAACAACTCTTTATGTGA 382
 362-13    351 AAATTTTCAGTCTAATCTCATTGAAAGCCACTCAACAACTCTTTATGTGA 400
1098-83SE  351 AAATTTTCAGTCTAATCTCATTGAAAGCCACTCAACAACTCTTTATGTGA 400
```

FIG. 11D

```
1012-25    383 CAG---------------------------------------------- 385
1013-35    383 CAG---------------------------------------------- 385
1020-40    383 CAG---------------------------------------------- 385
1072-45    383 CAG---------------------------------------------- 385
1075-49    383 CAG---------------------------------------------- 385
1075-51    383 CAG---------------------------------------------- 385
1076-59    401 CAG---------------------------------------------- 403
1077-62    383 CAG---------------------------------------------- 385
1086-67    383 CAG---------------------------------------------- 385
1086-69    401 CAG---------------------------------------------- 403
330-8      383 CAG---------------------------------------------- 385
1013-34    383 CAGA-----------------TGTAAAAAGTGCCTCAGAACGACCCTCC 414
1020-38    401 CAGA-----------------TGTAAAAAGTGCCTCAGAACGACCCTCC 432
1072-47    383 CAG-----------------ATGTAAAAAGTGCCTCAGAACGACCCTCC 414
1076-58    384 CAG-----------------ATGTAAAAAGTGCCTCAGAACGACCCTCC 415
1077-61    383 CAG-----------------ATGTAAAAAGTGCCTCAGAACGACCCTCC 414
1096-75    401 CAGA-----------------TGTAAAAAGTGCCTCAGAACGACCCTCC 432
1112-95    401 CAG-----------------ATGTAAAAAGTGCCTCAGAACGACCCTCC 432
310-4      383 CAG-----------------ATGTAAAAAGTGCCTCAGAACGACCCTCC 314
362-14     383 CAG-----------------ATGTAAAAAGTGCCTCAGAACGACCCTCC 314
330-10SE   383 CAGCATTTACTAACATTCCAGATGTAAAAAGTGCCTCAGAACGACCCTCC 432
362-13     401 CAGCATTTACTAACATTCCAGATGTAAAAAGTGCCTCAGAACGACCCTCC 450
1098-83SE  401 CAGA-----------------TGTAAAAAGTGCCTCAGAACGACCCTCC 432

1012-25    385 -------------------------------------------------- 385
1013-35    385 -------------------------------------------------- 385
1020-40    385 -------------------------------------------------- 385
1072-45    385 -------------------------------------------------- 385
1075-49    385 -------------------------------------------------- 385
1075-51    385 -------------------------------------------------- 385
1076-59    403 -------------------------------------------------- 403
1077-62    385 -------------------------------------------------- 385
1086-67    385 -------------------------------------------------- 385
1086-69    403 -------------------------------------------------- 403
330-8      385 -------------------------------------------------- 385
1013-34    415 AAGGACGAAATGGCAAGCAGACCCTGGCTCCTGTATAGTTTACTTCCTTT 464
1020-38    433 AAGGACGAAATGGCAAGCAGACCCTGGCTCCTGTATAGTTTACTTCCTTT 482
1072-47    415 AAGGACGAAATGGCAAGCAGACCCTGGCTCCTGTATAGTTTACTTCCTTT 464
1076-58    416 AAGGACGAAATGGCAAGCAGACCCTGGCTCCTGTATAGTTTACTTCCTTT 465
1077-61    415 AAGGACGAAATGGCAAGCAGACCCTGGCTCCTGTATAGTTTACTTCCTTT 464
1096-75    433 AAGGACGAAATGGCAAGCAGACCCTGGCTCCTGTATAGTTTACTTCCTTT 482
1112-95    433 AAGGACGAAATGGCAAGCAGACCCTGGCTCCTGTATAGTTTACTTCCTTT 482
310-4      415 AAGGACGAAATGGCAAGCAGACCCTGGCTCCTGTATAGTTTACTTCCTTT 464
362-14     415 AAGGACGAAATGGCAAGCAGACCCTGGCTCCTGTATAGTTTACTTCCTTT 464
330-10SE   433 AAGGACGAAATGGCAAGCAGACCCTGGCTCCTGTATAGTTTACTTCCTTT 482
362-13     451 AAGGACGAAATGGCAAGCAGACCCTGGCTCCTGTATAGTTTACTTCCTTT 500
1098-83SE  433 AAGGACGAAATGGCAAGCAGACCCTGGCTCCTGTATAGTTTACTTCCTTT 482
```

FIG. 11E

```
1012-25     385 ------------------------------------------------ 385
1013-35     385 ------------------------------------------------ 385
1020-40     385 ------------------------------------------------ 385
1072-45     385 ------------------------------------------------ 385
1075-49     385 ------------------------------------------------ 385
1075-51     385 ------------------------------------------------ 385
1076-59     403 ------------------------------------------------ 403
1077-62     385 ------------------------------------------------ 385
1086-67     385 ------------------------------------------------ 385
1086-69     403 ------------------------------------------------ 403
 330-8      385 ------------------------------------------------ 385
1013-34     465 GGGGGGATTGCCTCTACTCATCACTACCTGTTTCTGCCTGTTCTGCTGCC 514
1020-38     483 GGGGGGATTGCCTCTACTCATCACTACCTGTTTCTGCCTGTTCTGCTGCC 532
1072-47     465 GGGGGGATTGCCTCTACTCATCACTACCTGTTTCTGCCTGTTCTGCTGCC 514
1076-58     466 GGGGGGATTGCCTCTACTCATCACTACCTGTTTCTGCCTGTTCTGCTGCC 515
1077-61     465 GGGGGGATTGCCTCTACTCATCACTACCTGTTTCTGCCTGTTCTGCTGCC 514
1096-75     483 GGGGGGATTGCCTCTACTCATCACTACCTGTTTCTGCCTGTTCTGCTGCC 532
1112-95     483 GGGGGGATTGCCTCTACTCATCACTACCTGTTTCTGCCTGTTCTGCTGCC 532
 310-4      465 GGGGGGATTGCCTCTACTCATCACTACCTGTTTCTGCCTGTTCTGCTGCC 514
 362-14     465 GGGGGGATTGCCTCTACTCATCACTACCTGTTTCTGCCTGTTCTGCTGCC 514
 330-10SE   483 GGGGGGATTGCCTCTACTCATCACTACCTGTTTCTGCCTGTTCTGCTGCC 532
 362-13     501 GGGGGGATTGCCTCTACTCATCACTACCTGTTTCTGCCTGTTCTGCTGCC 550
1098-83SE   483 GGGGGGATTGCCTCTACTCATCACTACCTGTTTCTGCCTGTTCTGCTGCC 532

1012-25     386 ------G---------AAAGCAAAATGAACTCTCTGACACAGCAGGAAGG 420
1013-35     386 ----------------GAAAGCAAAATGAACTCTCTGACACAGCAGGAAGG 420
1020-40     386 ----------------GAAAGCAAAATGAACTCTCTGACACAGCAGGAAGG 420
1072-45     386 ----------------GAAAGCAAAATGAACTCTCTGACACAGCAGGAAGG 420
1075-49     386 ----------------GAAAGCAAAATGAACTCTCTGACACAGCAGGAAGG 420
1075-51     386 ----------------GAAAGCAAAATGAACTCTCTGACACAGCAGGAAGG 420
1076-59     404 ----------------GAAAGCAAAATGAACTCTCTGACACAGCAGGAAGG 438
1077-62     386 ----------------GAAAGCAAAATGAACTCTCTGACACAGCAGGAAGG 420
1086-67     386 ----------------GAAAGCAAAATGAACTCTCTGACACAGCAGGAAGG 420
1086-69     404 ----------------GAAAGCAAAATGAACTCTCTGACACAGCAGGAAGG 438
 330-8      386 ----------------GAAAGCAAAATGAACTCTCTGACACAGCAGGAAGG 420
1013-34     515 TGAGAAGGCACCAAGGAAAGCAAAATGAACTCTCTGACACAGCAGGAAGG 564
1020-38     533 TGAGAAGGCACCAAGGAAAGCAAAATGAACTCTCTGACACAGCAGGAAGG 582
1072-47     515 TGAGAAGGCACCAAGGAAAGCAAAATGAACTCTCTGACACAGCAGGAAGG 564
1076-58     516 TGAGAAGGCACCAAGGAAAGCAAAATGAACTCTCTGACACAGCAGGAAGG 565
1077-61     515 TGAGAAGGCACCAAGGAAAGCAAAATGAACTCTCTGACACAGCAGGAAGG 564
1096-75     533 TGAGAAGGCACCAAGGAAAGCAAAATGAACTCTCTGACACAGCAGGAAGG 582
1112-95     533 TGAGAAGGCACCAAGGAAAGCAAAATGAACTCTCTGACACAGCAGGAAGG 582
 310-4      515 TGAGAAGGCACCAAGGAAAGCAAAATGAACTCTCTGACACAGCAGGAAGG 564
 362-14     515 TGAGAAGGCACCAAGGAAAGCAAAATGAACTCTCTGACACAGCAGGAAGG 564
 330-10SE   533 TGAGAAGGCACCAAGGAAAGCAAAATGAACTCTCTGACACAGCAGGAAGG 582
 362-13     551 TGAGAAGGCACCAAGGAAAGCAAAATGAACTCTCTGACACAGCAGGAAGG 600
1098-83SE   533 TGAGAAGGCACCAAGGAAAGCAAAATGAACTCTCTGACACAGCAGGAAGG 582
```

FIG. 11F

```
1012-25     421 GAAATTAACCTGGTTGATGCTCACCTTAAGAGTGAGCAAACAGAAGCAAG 470
1013-35     421 GAAATTAACCTGGTTGATGCTCACCTTAAGAGTGAGCAAACAGAAGCAAG 470
1020-40     421 GAAATTAACCTGGTTGATGCTCACCTTGAGAGTGAGCAAACAGAAGCAAG 470
1072-45     421 GAAATTAACCTGGTTGATGCTCACCTTAAGAGTGAGCAAACAGAAGCAAG 470
1075-49     421 GAAATTAACCTGGTTGATGCTCACCTTAAGAGTGAGCAAACAGAAGCAAG 470
1075-51     421 GAAATTAACCTGGTTGATGCTCACCTTAAGAGTGAGCAAACAGAAGCAAG 470
1076-59     439 GAAATTAACCTGGTTGATGCTCACCTTAAGAGTGAGCAAACAGAAGCAAG 488
1077-62     421 GAAATTAACCTGGTTGATGCTCACCTTAAGAGTGAGCAAACAGAAGCAAG 470
1086-67     421 GAAATTAACCTGGTTGATGCTCACCTTAAGAGTGAGCAAACAGAAGCAAG 470
1086-69     439 GAAATTAACCTGGTTGATGCTCACCTTAAGAGTGAGCAAACAGAAGCAAG 488
330-8       421 GAAATTAACCTAGTTGATGCTCACCTTAAGAGTGAGCAAACAGAAGCAAG 470
1013-34     565 GAAATTAACCTGGTTGATGCTCACCTTAAGAGTGAGCAAACAGAAGCAAG 614
1020-38     583 GAAATTAACCTGGTTGATGCTCACCTTAAGAGTGAGCAAACAGAAGCAAG 632
1072-47     565 GAAATTAACCTGGTTGATGCTCACCTTAAGAGTGAGCAAACAGAAGCAAG 614
1076-58     566 GAAATTAACCTGGTTGATGCTCACCTTAAGAGTGAGCAAACAGAAGCAAG 615
1077-61     565 GAAATTAACCTGGTTGATGCTCACCTTAAGAGTGAGCAAACAGAAGCAAG 614
1096-75     583 GAAATTAACCTGGTTGATGCTCACCTTAAGAGTGAGCAAACAGAAGCAAG 632
1112-95     583 GAAATTAACCTGGTTGATGCTCACCTTAAGAGTGAGCAAACAGAAGCAAG 632
310-4       565 GAAATTAACCTGGTTGATGCTCACCTTAAGAGTGAGCAAACAGAAGCAAG 614
362-14      565 GAAATTAACCTGGTTGATGCTCACCTTAAGAGTGAGCAAACAGAAGCAAG 614
330-10SE    583 GAAATTAACCTGGTTGATGCTCACCTTAAGAGTGAGCAAACAGAAGCAAG 632
362-13      601 GAAATTAACCTGGTTGATGCTCACCTTAAGAGTGAGCAAACAGAAGCAAG 650
1098-83SE   583 GAAATTAACCTGGTTGATGCTCACCTTAAGAGTGAGCAAACAGAAGCAAG 632

1012-25     471 CACCAGGCAAAATTCCCAAGTACTGCTATCAGAAACTGGAATTTATGATA 520
1013-35     471 CACCAGGCAAAATTCCCAAGTACTGCTATCAGAAACTGGAATTTATGATA 520
1020-40     471 CACCAGGCAAAATTCCCAAGTACTGCTATCAGAAACTGGAATTTATGATA 520
1072-45     471 CACCAGGCAAAATTCCCAAGTACTGCTATCAGAAACTGGAATTTATGATA 520
1075-49     471 CACCAGGCAAAATTCCCAAGTACTGCTATCAGAAACTGGAATTTATGATA 520
1075-51     471 CACCAGGCAAAATTCCCAAGTACTGCTATCAGAAACTGGAATTTATGATA 520
1076-59     489 CACCAGGCAAAATTCCCAAGTACTGCTATCAGAAACTGGAATTTATGATA 538
1077-62     471 CACCAGGCAAAATTCCCAAGTACTGCTATCAGAAACTGGAATTTATGATA 520
1086-67     471 CACCAGGCAAAATTCCCAAGTACTGCTATCAGAAACTGGAATTTATGATA 520
1086-69     489 CACCAGGCAAAATTCCCAAGTACTGCTATCAGAAACTGGAATTTATGATA 538
330-8       471 CACCAGGCAAAATTCCCAAGTACTGCTATCAGAAACTGGAATTTATGATA 520
1013-34     615 CATCAGGCAAAATTCCCAAGTACTGCTATCAGAAACTGGAATTTATGATA 664
1020-38     633 CACCAGGCAAAATTCCCAAGTACTGCTATCAGAAACTGGAATTTATGATA 682
1072-47     615 CACCAGGCAAAATTCCCAAGTACTGCTATCAGAAACTGGAATTTATGATA 664
1076-58     616 CACCAGGCAAAATTCCCAAGTACTGCTATCAGAAACTGGAATTTATGATA 665
1077-61     615 CACCAGGCAAAATTCCCAAGTACTGCTATCAGAAACTGGAATTTATGATA 664
1096-75     633 CACCAGGCAAAATTCCCAAGTACTGCTATCAGAAACTGGAATTTATGATA 682
1112-95     633 CACCAGGCAAAATTCCCAAGTACTGCTATCAGAAACTGGAATTTATGATA 682
310-4       615 CACCAGGCAAAATTCCCGAGTACTGCTATCAGAAACTGGAATTTATGATA 664
362-14      615 CACCAGGCAAAATTCCCAAGTACTGCTATCAGAAACTGGAATTTATGATA 664
330-10SE    633 CACCAGGCAAAATTCCCAAGTACTGCTATCAGAAACTGGAATTTATGATA 682
362-13      651 CACCAGGCAAAATTCCCAAGTACTGCTATCAGAAACTGGAATTTATGATA 700
1098-83SE   633 CACCAGGCAAAATTCCCAAGTACTGCTATCAGAAACTGGAATTTATGATA 682
```

FIG. 11G

| | | | |
|---|---|---|---|
| 1012-25 | 521 | ATGACCCTGACCTTTGTTTCAGGATGCAGGAAGGGTCTGAAGTTTATTCT | 570 |
| 1013-35 | 521 | ATGACCCTGACCTTTGTTTCAGGATGCAGGAAGGGTCTGAAGTTTATTCT | 570 |
| 1020-40 | 521 | ATGACCCTGACCTTTGTTTCAGGATGCAGGAAGGGTCTGAAGTTTATTCT | 570 |
| 1072-45 | 521 | ATGACCCTGACCTTTGTTTCAGGATGCAGGAAGGGTCTGAAGTTTATTCT | 570 |
| 1075-49 | 521 | ATGACCCTGACCTTTGTTTCAGGATGCAGGAAGGGTCTGAAGTTTATTCT | 570 |
| 1075-51 | 521 | ATGACCCTGACCTTTGTTTCAGGATGCAGGAAGGGTCTGAAGTTTATTCT | 570 |
| 1076-59 | 539 | ATGACCCTGACCTTTGTTTCAGGATGCAGGAAGGGTCTGAAGTTTATTCT | 588 |
| 1077-62 | 521 | ATGACCCTGACCTTTGTTTCAGGATGCAGGAAGGGTCTGAAGTTTATTCT | 570 |
| 1086-67 | 521 | ATGACCCTGACCTTTGTTTCAGGATGCAGGAAGGGTCTGAAGTTTATTCT | 570 |
| 1086-69 | 539 | ATGACCCTGACCTTTGTTTCAGGATGCAGGAAGGGTCTGAAGTTTATTCT | 588 |
| 330-8 | 521 | ATGACCCTGACCTTTGTTTCAGGATGCAGGAAGGGTCTGAAGTTTATTCT | 570 |
| 1013-34 | 665 | ATGACCCTGACCTTTGTTTCAGGATGCAGGAAGGGTCTGAAGTTTATTCT | 714 |
| 1020-38 | 683 | ATGACCCTGACCTTTGTTTCAGGATGCAGGAAGGGTCTGAAGTTTATTCT | 732 |
| 1072-47 | 665 | ATGACCCTGACCTTTGTTTCAGGATGCAGGAAGGGTCTGAAGTTTATTCT | 714 |
| 1076-58 | 666 | ATGACCCTGACCTTTGTTTCAGGATGCAGGAAGGGTCTGAAGTTTATTCT | 715 |
| 1077-61 | 665 | ATGACCCTGACCTTTGTTTCAGGATGCAGGAAGGGTCTGAAGTTTATTCT | 714 |
| 1096-75 | 683 | ATGACCCTGACCTTTGTTTCAGGATGCAGGAAGGGTCTGAAGTTTATTCT | 732 |
| 1112-95 | 683 | ATGACCCTGACCTTTGTTTCAGGATGCAGGAAGGGTCTGAAGTTTATTCT | 732 |
| 310-4 | 665 | ATGACCCTGACCTTTGTTTCAGGATGCGGGAAGGGTCTGAAGTTTATTCT | 714 |
| 362-14 | 665 | ATGACCCTGACCTTTGTTTCAGGATGCAGGAAGGGTCTGAAGTTTATTCT | 714 |
| 330-10SE | 683 | ATGACCCTGACCTTTGTTTCAGGATGCAGGAAGGGTCTGAAGTTTATTCT | 732 |
| 362-13 | 701 | ATGACCCTGACCTTTGTTTCAGGATGCAGGAAGGGTCTGAAGTTTATTCT | 750 |
| 1098-83SE | 683 | ATGACCCTGACCTTTGTTTCAGGATGCAGGAAGGGTCTGAAGTTTATTCT | 732 |

| | | | |
|---|---|---|---|
| 1012-25 | 571 | AATCCATGCCTGGAAGAAAACAAACCAGGCATTGTTTATGCTTCCCTGAA | 620 |
| 1013-35 | 571 | AATCCATGCCTGGAAGAAAACAAACCAGGCATTGTTTATGCTTCCCTGAA | 620 |
| 1020-40 | 571 | AATCCATGCCTGGAAGAAAACAAACCAGGCATTGTTTATGCTTCCCTGAA | 620 |
| 1072-45 | 571 | AATCCATGCCTGGAAGAAAACAAACCAGGCATTGTTTATGCTTCCCTGAA | 620 |
| 1075-49 | 571 | AATCCATGCCTGGAAGAAAACAAACCAGGCATTGTTTATGCTTCCCTGAA | 620 |
| 1075-51 | 571 | AATCCATGCCTGGAAGAAAACAAACCAGGCATTGTTTATGCTTCCCTGAA | 620 |
| 1076-59 | 589 | AATCCATGCCTGGAAGAAAACAAACCAGGCATTGTTTATGCTTCCCTGAA | 638 |
| 1077-62 | 571 | AATCCATGCCTGGAAGAAAACAAACCAGGCATTGTTTATGCTTCCCTGAA | 620 |
| 1086-67 | 571 | AATCCATGCCTGGAAGAAAACAAACCAGGCATTGTTTATGCTTCCCTGAA | 620 |
| 1086-69 | 589 | AATCCATGCCTGGAAGAAAACAAACCAGGCATTGTTTATGCTTCCCTGAA | 638 |
| 330-8 | 571 | AATCCATGCCTGGAAGAAAACAAACCAGGCATTGTTTATGCTTCCCTGAA | 620 |
| 1013-34 | 715 | AATCCATGCCTGGAAGAAAACAAACCAGGCATTGTTTATGCTTCCCTGAA | 764 |
| 1020-38 | 733 | AATCCATGCCTGGAAGAAAACAAACCAGGCATTGTTTATGCTTCCCTGAA | 782 |
| 1072-47 | 715 | AATCCATGCCTGGAAGAAAACAAACCAGGCATTGTTTATGCTTCCCTGAA | 764 |
| 1076-58 | 716 | AATCCATGCCTGGAAGAAAACAAACCAGGCATTGTTTATGCTTCCCTGAA | 765 |
| 1077-61 | 715 | AATCCATGCCTGGAAGAAAACAAACCAGGCATTGTTTATGCTTCCCTGAA | 764 |
| 1096-75 | 733 | AATCCATGCCTGGAAGAAAACAAACCAGGCATTGTTTATGCTTCCCTGAA | 782 |
| 1112-95 | 733 | AATCCATGCCTGGAAGAAAACAAACCAGGCATTGTTTATGCTTCCCTGAA | 782 |
| 310-4 | 715 | AATCCATGCCTGGAAGAAAACAAACCAGGCATTGTTTATGCTTCCCTGAA | 764 |
| 362-14 | 715 | AATCCATGCCTGGAAGAAAACAAACCAGGCATTGTTTATGCTTCCCTGAA | 764 |
| 330-10SE | 733 | AATCCATGCTTGGAAGAAAACAAACCAGGCATTGTTTATGCTTCCCTGAA | 782 |
| 362-13 | 751 | AATCCATGCCTGGAAGAAAACAAACCAGGCATTGTTTATGCTTCCCTGAA | 800 |
| 1098-83SE | 733 | AATCCATGCCTGGAAGAAAACAAACCAGGCATTGTTTATGCTTCCCTGAA | 782 |

*FIG. 11H*

```
1012-25     621 TCATTCTGTCATTGGACTGAACTCAAGACTGGCAAGAAATGTAAAAGAAG 670
1013-35     621 CCATTCTGTCATTGGACCGAACTCAAGACTGGCAAGAAATGTAAAAGAAG 670
1020-40     621 CCATTCTGTCATTGGACTGAACTCAAGACTGGCAAGAAATGTAAAAGAAG 670
1072-45     621 CCATTCTGTCATTGGACTGAACTCAAGACTGGCAAGAAATGTAAAAGAAG 670
1075-49     621 CCATTCTGTCATTGGACTGAACTCAAGACTGGCAAGAAATGTAAAAGAAG 670
1075-51     621 CCATTCTGTCATTGGACCGAACTCAAGACTGGCAAGAAATGTGAAAGAAG 670
1076-59     639 CCATTCTGTCATTGGACTGAACTCAAGACTGGCAAGAAATGTAAAAGAAG 688
1077-62     621 CCATTCTGTCATTGGACTGAACTCAAGACTGGCAAGAAATGTAAAAGAAG 670
1086-67     621 CCATTCTGTCATTGGACCGAACTCAAGACTGGCAAGAAATGTAAAAGAAG 670
1086-69     639 CCATTCTGTCATTGGACTGAACTCAAGACTGGCAAGAAATGTAAAAGAAG 688
 330-8      621 CCATTCTGTCATTGGACCGAACTCAAGACTGGCAAGAAATGTAAAAGAAG 670
1013-34     765 CCATTCTGTCATTGGACCGAACTCAAGACTGGCAAGAAATGTAAAAGAAG 814
1020-38     783 CCATTCTGTCATTGGACTGAACTCAAGACTGGCAAGAAATGTAAAAGAAG 832
1072-47     765 CCATTCTGTCATTGGACTGAACTCAAGACTGGCAAGAAATGTAAAAGAAG 814
1076-58     766 CCATTCTGTCATTGGACTGAACTCAAGACTGGCAAGAAATGTAAAAGAAG 815
1077-61     765 CCATTCTGTCATTGGACTGAACTCAAGACTGGCAAGAAATGTAAAAGAAG 814
1096-75     783 CCATTCTGTCATTGGACTGAACTCAAGACTGGCAAGAAATGTAAAAGAAG 832
1112-95     783 CCATTCTGTCATTGGACTGAACTCAAGACTGGCAAGAAATGTAAAAGAAG 832
 310-4      765 CCATTCTGTCATTGGACTGAACTCAAGACTGGCAAGAAATGTAAAAGAAG 814
 362-14     765 CCATTCTGTCATTGGACTGAACTCAAGACTGGCAAGAAATGTAAAAGAAG 814
 330-10SE   783 CCATTCTGTCATTGGACTGAACTCAAGACTGGCAAGAAATGTAAAAGAAG 832
 362-13     801 CCATTCTGTCATTGGACTGAACTCAAGACTGGCAAGAAATGTAAAAGAAG 850
1098-83SE   783 CCATTCTGTCATTGGACTGAACTCAAGACTGGCAAGAAATGTAAAAGAAG 832

1012-25     671 CACCAACAGAATATGCA-CCATATGTGTGA-------- 699
1013-35     671 CACCAACAGAATATGCATCCATATGTGTGAGGAGTTAA 708
1020-40     671 CACCAACAGAATATGCATCCATATGTGTGAGGAGTTAA 708
1072-45     671 CACCAACAGAATATGCATCCATATGTGTGAGGAGTTAA 708
1075-49     671 CACCAACAGAATATGCATCCATATGTGTGAGGAGTTAA 708
1075-51     671 CACCAACAGAATATGCATCCATATGTGTGAGGAGTTAA 708
1076-59     689 CACCAACAGAATATGCATCCATATGTGTGAGGAGTTAA 726
1077-62     671 CACCAACAGAATATGCATCCATATGTGTGAGGAGTTAA 708
1086-67     671 CACCAACAGAATATGCATCCATATGTGTGAGGAGTTAA 708
1086-69     689 CACCAACAGAATATGCATCCATATGTGTGAGGAGTTAA 726
 330-8      671 CACCAACAGAATATGCATCCATATGTGTGAGGAGTTAA 708
1013-34     815 CACCAACAGAATATGCATCCATATGTGTGAGGAGTTAA 852
1020-38     833 CACCAACAGAATATGCATCCATATGTGTGAGGAGTTAA 870
1072-47     815 CACCAACAGAATATGCATCCATATGTGTGAGGAGTTAA 852
1076-58     816 CACCAACAGAATATGCATCCATATGTGTGAGGAGTTAA 853
1077-61     815 CACCAACAGAATATGCATCCATATGTGTGAGGAGTTAA 852
1096-75     833 CACCAACAGAATATGCATCCATATGTGTGAGGAGTTAA 870
1112-95     833 CACCAACAGAATATGCATCCATATGTGTGAGGAGTTAA 870
 310-4      815 CACCAACAGAATATGCATCCATATGTGTGAGGAGTTAA 852
 362-14     815 CACCAACAGAATATGCATCCATATGTGTGAGGAGTTAA 852
 330-10SE   833 CACCAACAGAATATGCATCCATATGTGTGAGGAGT--- 867
 362-13     851 CACCAACAGAATATGCATCCATATGTGTGAGGAGTTAA 888
1098-83SE   833 CACCAACAGAATATGCATCCATATGTGTGAGGAGTTAA 870
```

FIG. 11I

```
1012-25     1 ------MLGTGKLFWVFFLIPYLDIWNIHGKESCDVQLYIKRQSEHSILA 44
1013-35     1 ------MLGTGKLFWVFFLIPYLDIWNIHGKESCDVQLYIKRQSEHSILA 44
1020-40     1 ------MLGTGKLFWVFFLIPYLDIWNIHGKESCDVQLYIKRQSEHSILA 44
1072-45     1 ------MLGTGKLFWVFFLIPYLDIWNIHGKESCDVQLYIKRQSEHSILA 44
1075-49     1 ------MLGTGKLFWVFFLIPYLDIWNIHGKESCDVQLYIKRQSEHSILA 44
1075-51     1 ------MLGTGKLFWVFFLIPYLDIWNIHGKESRDVQLYIKRQSEHSILA 44
1076-59     1 MKTLPAMLGTGKLFWVFFLIPYLDIWNIHGKESCDVQLYIKRQSEHSILA 50
1077-62     1 ------MLGTGNLFWVFFLIPYLDIWNIHGKESCDVQLYIKRQSEHSILA 44
1086-67     1 ------MLGTGKLFWVFFLIPYLDIWNIHGKESCDVQLYIKRQSEHSILA 44
1086-69     1 MKTLPAMLGTGKLFWVFFLIPYLDIWNIHGKESCDVQLYIKRQSEHSILA 50
330-8       1 ------MLGTGKLFWVFFLIPYLDIWNIHGKESCDVQLYIKRQSEHSILA 44
1013-34     1 ------MLGTGKLFWVFFLIPYLDIWNIHGKESCDVQLYIKRQSEHSILA 44
1020-38     1 MKTLPAMLGTGKLFWVFFLIPYLDIWNIHGKESCDVQLYIKRQSEHSILA 50
1072-47     1 ------MLGTGKLFWVFFLIPYLDIWNIHGKESCDVQLYIKRQSEHSILA 44
1076-58     1 ------MLGTGKLFWVFFLIPYLDIWNIHGKESCDVQLYIKSQSEHSILA 44
1077-61     1 ------MLGTGELFWVFFLIPYLDIWNIHGKESCDVQLYIKRQSEHSILA 44
1096-75     1 MKTLPAMLGTGKLFWVFFLIPYLDIWNIHGKESCDVQLYIKRQSEHSILA 50
1112-95     1 MKTLPAMLGTGKLFWVFFLIPYLDIWNIHGKESCDVQLYIKRQSEHSILA 50
310-4       1 ------MLGTGKLFWVFFLIPYLDIWNIHGKESCDVQLYIKRQSEHSILA 44
362-14      1 ------MLGTGKLFWVFFLIPYLDIWNIHGKESCDVQLYIKRQSEHSILA 44
597-22      1 MKTLPAMLGTGKLFWVFFLIPYLDIWNIHGKESCDVQLYIKRQSEHSILA 50
1098-83SE   1 MKTLPAMLGTGKLFWVFFLIPYLDIWNIHGKESCDVQLYIKRQSEHSILA 50
362-13      1 MKTLPAMLGTGKLFWVFSLIPYLDIWNIHGKESCDVQLYIKRQSEHSILA 50
330-10SE    1 ------MLGTGKLFWVFFLIPYLDIWNIHGKESCDVQLYIKRQSEHSILA 44

1012-25    45 GDPFELECPVKYCANRPHVTWCKLNGTTCVKLEDRQTSWKEEKNISFFIL 94
1013-35    45 GDPFELECPVKYCANRPHVTWCKLNGTTCVKLEDRQTSWKEEKNISFFIL 94
1020-40    45 GDPFELECPVKYCANRPHVTWCKLNGTTCVKLEDRQTSWKEEKNISFFIL 94
1072-45    45 GDPFELECPVKYCANRPHVTWCKLNGTTCVKLEDRQTSWKEEKNISFFIL 94
1075-49    45 GDPFELECPVKYCANRPHVTWCKLNGTTCVKLEDRQTSWKEEKNISFFIL 94
1075-51    45 GDPFELECPVKYCANRPHVTWCKLNGTTCVKLEDRQTSWKEEKNISFFIL 94
1076-59    51 GDPFELECPVKYCANRPHVTWCKLNGTTCVKLEDRQTSWKEEKNISFFIL 100
1077-62    45 GDPFELECPVKYCANRPHVTWCKLNGTTCVKLEDRQTSWKEEKNISFFIL 94
1086-67    45 GDPFELECPVKYCANRPHVTWCKLNGTTCVKLEDRQTSWKGEKNISFFIL 94
1086-69    51 GDPFELECPVKYCANRPHVTWCKLNGTACVKLEDRQTSWKEEKNISFFIL 100
330-8      45 GDPFELECPVKYGANRPHVTWCKLNGTTCVKLGDRQTSWKEEKNISFFIL 94
1013-34    45 GDPFELECPVKYCANRPHVTWCKLNGTTCVKLEDRQTSWKEEKNISFFIL 94
1020-38    51 GDPFELECPVKYCANRPHVTWCKLNGTTCVKLEDRQTSWKEEKNISFFIL 100
1072-47    45 GDPFELECPVKYCANRPHVTWCKLNGTTCVKLEDRQTSWKEEKNISFFIL 94
1076-58    45 GDPFELECPVKYCANRPHVTWCKLNGTTCVKLEDRQTSWKEEKNISFFIL 94
1077-61    45 GDPFELECPVKYCANRPHVTWCKLNGTTCVKLEDRQTSWKEEKNISFFIL 94
1096-75    51 GDPFELECPVKYCANRPHVTWCKLNGTTCVKLEDRQTSWKEEKNISFFIL 100
1112-95    51 GDPFELECPVKYCANRPHVTWCKLNGTTCVKLEDRQTSWKEEKNISFFIL 100
310-4      45 GDPFELECPVKYCANRPHVTWCKLNGTTCVKLEDRQTSWKEEKNISFFIL 94
362-14     45 GDPFELECPVKYCANRPHVTWCKLNGTTCVKLEDRQTSWKEEKNISFFIL 94
597-22     51 GDPFELECPVKYCANRPHVTWCKLNGTTCVKLEDRQTSWKEEKNISFFIL 100
1098-83SE  51 GDPF-LECPVKYCANRPHVTWCKLNGTTCVKLEDRQTSWKEEKNISFFIL 99
362-13     51 GDPFELECPVKYCANRPHVTWCKLNGTTCVKLEDRQTSWKEEKNISSFIL 100
330-10SE   45 GDPFELECPVKYCANRPHVTWCKLNGTTCVKLEDRQTSWKEEKNISFFIL 94
```

FIG. 12A

```
1012-25     95 RFEPVLPNDNGSYRCSANFQSNLIESHSTTLYVT---------------- 128
1013-35     95 HFEPVLPNDNGSYRCSANFQSNLIESHSTTLYVT---------------- 128
1020-40     95 HFEPVLPNDDGSYRCSANFQSNLIESHSTTLYVT---------------- 128
1072-45     95 HFEPVLPNDNGSYRCSANFQSNLIESHSTTLYVT---------------- 128
1075-49     95 HFEPVLPNDNGSYRCSANFQSNLIESHSTTLYVT---------------- 128
1075-51     95 HFEPVLPNDNGSYRCSANFQSNLIESHSTTLYVT---------------- 128
1076-59    101 HFEPVLPNDNGSYRCSANFQSNLIESHSTTLYVT---------------- 134
1077-62     95 HFEPVLPNDNGSYRCSANFQSNLIESHSTTLYVA---------------- 128
1086-67     95 HFEPVLPNDNGSYRCSANFQSNLIESHSTTLYVT---------------- 128
1086-69    101 HFEPVLPNDNGSYRCSANFQSNLIESHSTTLYVT---------------- 134
 330-8      95 HFEPVLPNDNGSYRCSANFQSNLIESHSTTLYVT---------------- 128
1013-34     95 HFEPVLPNDNGSYRCSANFQSNLIESHSTTLYVT------DVKSASERPS 138
1020-38    101 HFEPVLPNDNGSYRCSANFQSNLIESHSTTLYVT------DVKSASERPS 144
1072-47     95 HFEPVLPNDNGSYRCSANFQSNLIESHSTTLYVT------DVKSASERPS 138
1076-58     95 HFEPVLPNDNGSYRCSANFQSNLIESHSTTLYVT------DVKSASERPS 138
1077-61     95 HFEPALPNDNGSYRCSANFQSNLIESHSTTLYVT------DVKSASERPS 138
1096-75    101 HFEPVLPNDNGSYRCSANFQSNLIESHSTTLYVT------DVKSASERPS 144
1112-95    101 HFEPVLPNDNGSYRCSANFQSNLIESHSTTLYVT------DVKSASERPS 144
 310-4      95 HFEPVLPNDNGSYRCSANFQSNLIESHSTTLYVT------DVKSASERPS 138
 362-14     95 HFEPVLPNDNGSYRCSANFQSNLIESHSTTLYVT------DVKSASERPS 138
 597-22    101 HFEPVLPNDNGSYRCSANFQSNLIESHSTTLYVT------DVKSASERPS 144
1098-83SE  100 HFEPVLPNDNGSYRCSANFQSNLIESHSTTLYVT------DVKSASERPS 143
 362-13    101 HFEPVLPNDNGSYRCSANFQSNLIESHSTTLYVTAFTNIPDVKSASERPS 150
 330-10SE   95 HFEPVLPNDNGSYRCSANFQSNLIESHSTTLYVTAFTNIPDVKSASERPS 144

1012-25    129 --------------------------------GKQNELSDTAGR 140
1013-35    129 --------------------------------GKQNELSDTAGR 140
1020-40    129 --------------------------------GKQNELSDTAGR 140
1072-45    129 --------------------------------GKQNELSDTAGR 140
1075-49    129 --------------------------------GKQNELSDTAGR 140
1075-51    129 --------------------------------GKQNELSDTAGR 140
1076-59    135 --------------------------------GKQNELSDTAGR 146
1077-62    129 --------------------------------GKQNELSDTAGR 140
1086-67    129 --------------------------------GKQNELSDTAGR 140
1086-69    135 --------------------------------GKQNELSDTAGR 146
 330-8     129 --------------------------------GKQNELSDTAGR 140
1013-34    139 KDEMASRPWLLYSLLPLGGLPLLITTCFCLFCCLRRHQGKQNELSDTAGR 188
1020-38    145 KDEMASRPWLLYSLLPLGGLPLLITTCFCLFCCLRRHQGKQNELSDTAGR 194
1072-47    139 KDEMASRPWLLYSLLPLGGLPLLITTCFCLFCCLRRHQGKQNELSDTAGR 188
1076-58    139 KDEMASRPWLLYSLLPLGGLPLLITTCFCLFCCLRRHQGKQNELSDTAGR 188
1077-61    139 KDEMASRPWLLYSLLPLGGLPLLITTCFCLFCCLRRHQGKQNELSDTAGR 188
1096-75    145 KDEMASRPWLLYSLLPLGGLPLLITTCFCLFCCLRRHQGKQNELSDTAGR 194
1112-95    145 KDEMASRPWLLYSLLPLGGLPLLITTCFCLFCCLRRHQGKQNELSDTAGR 194
 310-4     139 KDEMASRPWLLYSLLPLGGLPLLITTCFCLFCCLRRHQGKQNELSDTAGR 188
 362-14    139 KDEMASRPWLLYSLLPLGGLPLLITTCFCLFCCLRRHQGKQNELSDTAGR 188
 597-22    145 KDEMASRPWLLYSLLPLGGLPLLITTCFCLFCCLRRHQGKQNELSDTAGR 194
1098-83SE  144 KDEMASRPWLLYSLLPLGGLPLLITTCFCLFCCLRRHQGKQNELSDTAGR 193
 362-13    151 KDEMASRPWLLYSLLPLGGLPLLITTCFCLFCCLRRHQGKQNELSDTAGR 200
 330-10SE  145 KDEMASRPWLLYSLLPLGGLPLLITTCFCLFCCLRRHQGKQNELSDTAGR 194
```

FIG. 12B

```
1012-25    141 EINLVDAHLKSEQTEASTRQNSQVLLSETGIYDNDPDLCFRMQEGSEVYS 190
1013-35    141 EINLVDAHLKSEQTEASTRQNSQVLLSETGIYDNDPDLCFRMQEGSEVYS 190
1020-40    141 EINLVDAHLESEQTEASTRQNSQVLLSETGIYDNDPDLCFRMQEGSEVYS 190
1072-45    141 EINLVDAHLKSEQTEASTRQNSQVLLSETGIYDNDPDLCFRMQEGSEVYS 190
1075-49    141 EINLVDAHLKSEQTEASTRQNSQVLLSETGIYDNDPDLCFRMQEGSEVYS 190
1075-51    141 EINLVDAHLKSEQTEASTRQNSQVLLSETGIYDNDPDLCFRMQEGSEVYS 190
1076-59    147 EINLVDAHLKSEQTEASTRQNSQVLLSETGIYDNDPDLCFRMQEGSEVYS 196
1077-62    141 EINLVDAHLKSEQTEASTRQNSQVLLSETGIYDNDPDLCFRMQEGSEVYS 190
1086-67    141 EINLVDAHLKSEQTEASTRQNSQVLLSETGIYDNDPDLCFRMQEGSEVYS 190
1086-69    147 EINLVDAHLKSEQTEASTRQNSQVLLSETGIYDNDPDLCFRMQEGSEVYS 196
 330-8     141 EINLVDAHLKSEQTEASTRQNSQVLLSETGIYDNDPDLCFRMQEGSEVYS 190
1013-34    189 EINLVDAHLKSEQTEASIRQNSQVLLSETGIYDNDPDLCFRMQEGSEVYS 238
1020-38    195 EINLVDAHLKSEQTEASTRQNSQVLLSETGIYDNDPDLCFRMQEGSEVYS 244
1072-47    189 EINLVDAHLKSEQTEASTRQNSQVLLSETGIYDNDPDLCFRMQEGSEVYS 238
1076-58    189 EINLVDAHLKSEQTEASTRQNSQVLLSETGIYDNDPDLCFRMQEGSEVYS 238
1077-61    189 EINLVDAHLKSEQTEASTRQNSQVLLSETGIYDNDPDLCFRMQEGSEVYS 238
1096-75    195 EINLVDAHLKSEQTEASTRQNSQVLLSETGIYDNDPDLCFRMQEGSEVYS 244
1112-95    195 EINLVDAHLKSEQTEASTRQNSQVLLSETGIYDNDPDLCFRMQEGSEVYS 244
 310-4     189 EINLVDAHLKSEQTEASTRQNSRVLLSETGIYDNDPDLCFRMREGSEVYS 238
 362-14    189 EINLVDAHLKSEQTEASTRQNSQVLLSETGIYDNDPDLCFRMQEGSEVYS 238
 597-22    195 EINLVDAHLKSEQTEASTRQNSQVLLSETGIYDNDPDLCFRMQEGSEVYS 244
1098-83SE  194 EINLVDAHLKSEQTEASTRQNSQVLLSETGIYDNDPDLCFRMQEGSEVYS 243
 362-13    201 EINLVDAHLKSEQTEASTRQNSQVLLSETGIYDNDPDLCFRMQEGSEVYS 250
 330-10SE  195 EINLVDAHLKSEQTEASTRQNSQVLLSETGIYDNDPDLCFRMQEGSEVYS 244

1012-25    191 NPCLEENKPGIVYASLNHSVIGLNSRLARNVKEAPTEYAPYV---    232
1013-35    191 NPCLEENKPGIVYASLNHSVIGPNSRLARNVKEAPTEYASICVRS  235
1020-40    191 NPCLEENKPGIVYASLNHSVIGLNSRLARNVKEAPTEYASICVRS  235
1072-45    191 NPCLEENKPGIVYASLNHSVIGLNSRLARNVKEAPTEYASICVRS  235
1075-49    191 NPCLEENKPGIVYASLNHSVIGLNSRLARNVKEAPTEYASICVRS  235
1075-51    191 NPCLEENKPGIVYASLNHSVIGPNSRLARNVKEAPTEYASICVRS  235
1076-59    197 NPCLEENKPGIVYASLNHSVIGLNSRLARNVKEAPTEYASICVRS  241
1077-62    191 NPCLEENKPGIVYASLNHSVIGLNSRLARNVKEAPTEYASICVRS  235
1086-67    191 NPCLEENKPGIVYASLNHSVIGPNSRLARNVKEAPTEYASICVRS  235
1086-69    197 NPCLEENKPGIVYASLNHSVIGLNSRLARNVKEAPTEYASICVRS  241
 330-8     191 NPCLEENKPGIVYASLNHSVIGPNSRLARNVKEAPTEYASICVRS  235
1013-34    239 NPCLEENKPGIVYASLNHSVIGPNSRLARNVKEAPTEYASICVRS  283
1020-38    245 NPCLEENKPGIVYASLNHSVIGLNSRLARNVKEAPTEYASICVRS  289
1072-47    239 NPCLEENKPGIVYASLNHSVIGLNSRLARNVKEAPTEYASICVRS  283
1076-58    239 NPCLEENKPGIVYASLNHSVIGLNSRLARNVKEAPTEYASICVRS  283
1077-61    239 NPCLEENKPGIVYASLNHSVIGLNSRLARNVKEAPTEYASICVRS  283
1096-75    245 NPCLEENKPGIVYASLNHSVIGLNSRLARNVKEAPTEYASICVRS  289
1112-95    245 NPCLEENKPGIVYASLNHSVIGLNSRLARNVKEAPTEYASICVRS  289
 310-4     239 NPCLEENKPGIVYASLNHSVIGLNSRLARNVKEAPTEYASICVRS  283
 362-14    239 NPCLEENKPGIVYASLNHSVIGLNSRLARNVKEAPTEYASICVRS  283
 597-22    245 NPCLEENKPGIVYASLNHSVIGLNSRLARNVKEAPTEYASICVRS  289
1098-83SE  244 NPCLEENKPGIVYASLNHSVIGLNSRLARNVKEAPTEYASICVRS  288
 362-13    251 NPCLEENKPGIVYASLNHSVIGLNSRLARNVKEAPTEYASICVRS  295
 330-10SE  245 NPCLEENKPGIVYASLNHSVIGLNSRLARNVKEAPTEYASICVRS  289
```

FIG. 12C

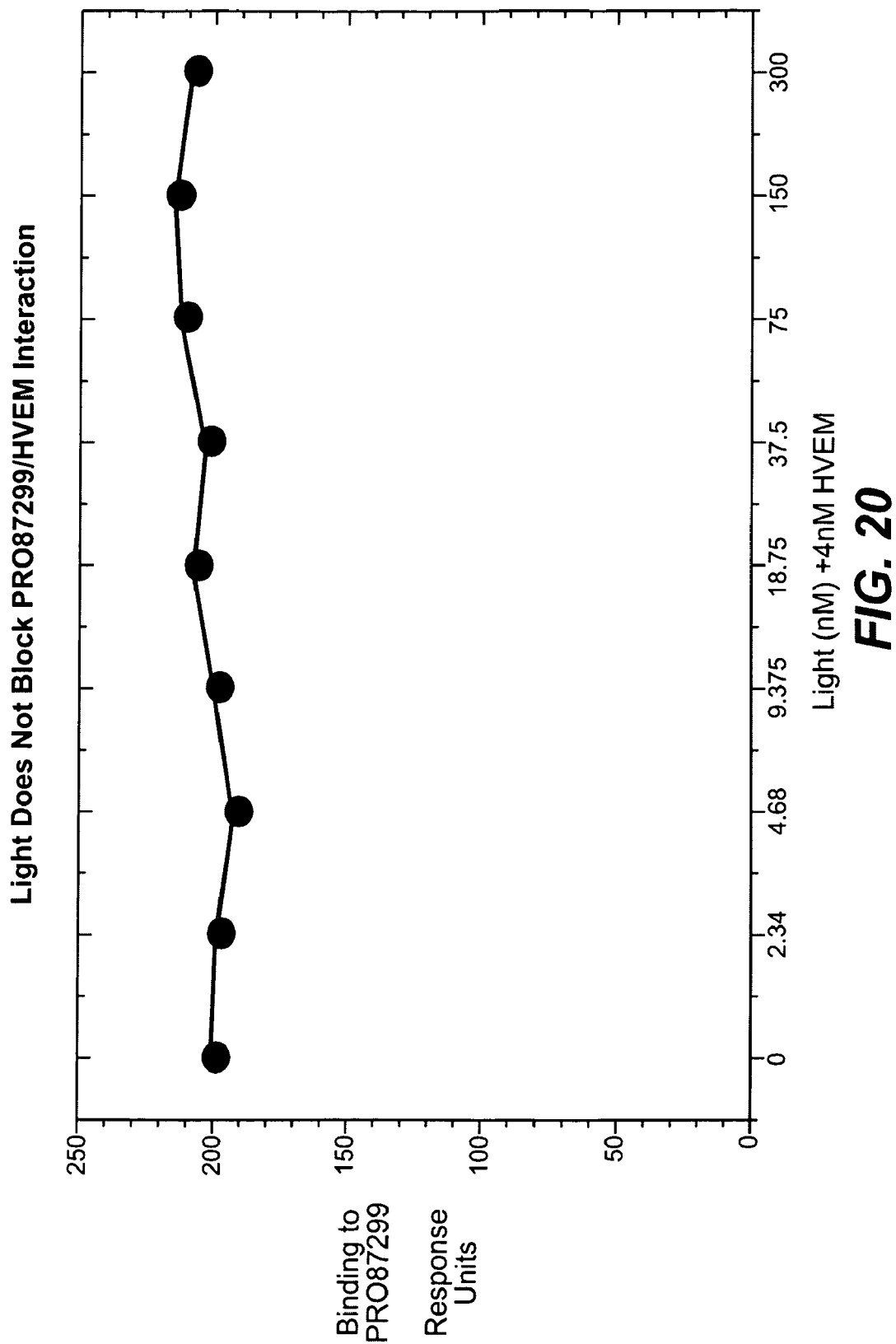

ANTI-PRO87299 ANTIBODIES

RELATED APPLICATIONS

This application is a divisional of U.S. patent application Ser. No. 10/987,663, filed on Nov. 12, 2004, which is a continuation-in-part of U.S. patent application Ser. No. 10/371, 341, filed on Feb. 19, 2003, now U.S. Pat. No. 7,153,950, which claims the benefit of U.S. Provisional Application No. 60/421,236, filed Oct. 25, 2002. The contents of the foregoing applications are incorporated herein by reference in their entirety.

FIELD OF THE INVENTION

The present invention relates to compositions and methods useful for the diagnosis and treatment of immune related diseases.

BACKGROUND OF THE INVENTION

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

Many immune related diseases are known and have been extensively studied. Such diseases include immune-mediated inflammatory diseases, non-immune-mediated inflammatory diseases, infectious diseases, immunodeficiency diseases, neoplasia, etc.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

Immune related diseases could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

CD4+ T cells are known to be important regulators of inflammation. Herein, CD4+ T cells were activated and the profile of genes differentially expressed upon activation was analyzed. As such, the activation specific genes may be potential therapeutic targets. In vivo co-stimulation is necessary for a productive immune proliferative response. The list of costimulatory molecules is quite extensive and it is still unclear just which co-stimulatory molecules play critical roles in different types and stages of inflammation.

The term inflammatory bowel disorder ("IBD") describes a group of chronic inflammatory disorders of unknown causes in which the intestine (bowel) becomes inflamed, often causing recurring cramps or diarrhea. The prevalence of IBD in the US is estimated to be about 200 per 100,000 population. Patients with IBD can be divided into two major groups, those with ulcerative colitis ("UC") and those with Crohn's disease ("CD").

In patients with UC, there is an inflammatory reaction primarily involving the colonic mucosa. The inflammation is typically uniform and continuous with no intervening areas of normal mucosa. Surface mucosal cells as well as crypt epithelium and submucosa are involved in an inflammatory reaction with neutrophil infiltration. Ultimately, this situation typically progresses to epithelial damage with loss of epithelial cells resulting in multiple ulcerations, fibrosis, dysplasia and longitudinal retraction of the colon.

CD differs from UC in that the inflammation extends through all layers of the intestinal wall and involves mesentery as well as lymph nodes. CD may affect any part of the alimentary canal from mouth to anus. The disease is often discontinuous, i.e., severely diseased segments of bowel are separated from apparently disease-free areas. In CD, the bowel wall also thickens which can lead to obstructions. In addition, fistulas and fissures are not uncommon.

Clinically, IBD is characterized by diverse manifestations often resulting in a chronic, unpredictable course. Bloody diarrhea and abdominal pain are often accompanied by fever and weight loss. Anemia is not uncommon, as is severe fatigue. Joint manifestations ranging from arthralgia to acute arthritis as well as abnormalities in liver function are commonly associated with IBD. Patients with IBD also have an increased risk of colon carcinomas compared to the general population. During acute "attacks" of IBD, work and other normal activity are usually impossible, and often a patient is hospitalized.

Although the cause of IBD remains unknown, several factors such as genetic, infectious and immunologic susceptibility have been implicated. IBD is much more common in Caucasians, especially those of Jewish descent. The chronic inflammatory nature of the condition has prompted an intense search for a possible infectious cause. Although agents have been found which stimulate acute inflammation, none has been found to cause the chronic inflammation associated with IBD. The hypothesis that IBD is an autoimmune disease is supported by the previously mentioned extraintestinal manifestation of IBD as joint arthritis, and the known positive response to IBD by treatment with therapeutic agents such as adrenal glucocorticoids, cyclosporine and azathioprine, which are known to suppress immune response. In addition, the GI tract, more than any other organ of the body, is continuously exposed to potential antigenic substances such as proteins from food, bacterial byproducts (LPS), etc.

Further, the risk of colon cancer is highly elevated in patients with severe ulcerative colitis, particularly if the disease has existed for several years. About 20-25% of patients with IBD eventually require surgery for removal of the colon because of massive bleeding, chronic debilitating illness, per-formation of the colon, or risk of cancer. Surgery is also sometimes performed when other forms of medical treatment fail or when the side effects of steroids or other medications threaten the patient's health. As surgery is invasive and drastically life altering, it is not a highly desirable treatment regimen, and is typically the treatment of last resort. In order to better understand this disease and possibly treat it, experiments determined that a gene was upregulated both in CD and UC when compared to normal tissue.

Despite the above identified advances in immune disorder research, there is a great need for additional diagnostic and therapeutic agents capable of detecting the presence of a immune disorders in a mammal and for effectively reducing these disorders. Accordingly, it is an objective of the present invention to identify and characterize a polypeptide that is overexpressed in various immune cells, involved in various immune disorders and to use that polypeptide, and the encoding nucleic acids, to produce compositions of matter useful in the therapeutic treatment and diagnostic detection of immune disorders in mammals.

SUMMARY OF THE INVENTION

A. Embodiments

The present invention concerns compositions and methods useful for the diagnosis and treatment of immune related disease in mammals, including humans. The present invention is based on the identification of proteins (including agonist and antagonist antibodies) which are a result of stimulation of the immune response in mammals. Immune related diseases can be treated by suppressing or enhancing the immune response. Molecules that enhance the immune response stimulate or potentiate the immune response to an antigen. Molecules which stimulate the immune response can be used therapeutically where enhancement of the immune response would be beneficial. Alternatively, molecules that suppress the immune response attenuate or reduce the immune response to an antigen (e.g., neutralizing antibodies) can be used therapeutically where attenuation of the immune response would be beneficial (e.g., inflammation). Accordingly, the PRO87299 polypeptides, agonists and antagonists thereof are also useful to prepare medicines and medicaments for the treatment of immune-related and inflammatory diseases. In a specific aspect, such medicines and medicaments comprise a therapeutically effective amount of a PRO87299 polypeptide, agonist or antagonist thereof with a pharmaceutically acceptable carrier. Preferably, the admixture is sterile.

In a further embodiment, the invention concerns a method of identifying agonists or antagonists to a PRO87299 polypeptide which comprises contacting the PRO87299 polypeptide with a candidate molecule and monitoring a biological activity mediated by said PRO87299 polypeptide. Preferably, the PRO87299 polypeptide is a native sequence PRO87299 polypeptide. In a specific aspect, the PRO87299 agonist or antagonist is an anti-PRO87299 antibody.

In another embodiment, the invention concerns a composition of matter comprising a PRO87299 polypeptide or an agonist or antagonist antibody which binds the polypeptide in admixture with a carrier or excipient. In one aspect, the composition comprises a therapeutically effective amount of the polypeptide or antibody. In another aspect, when the composition comprises an immune stimulating molecule, the composition is useful for: (a) increasing infiltration of inflammatory cells into a tissue of a mammal in need thereof, (b) stimulating or enhancing an immune response in a mammal in need thereof, (c) increasing the proliferation of immune cells in a mammal in need thereof in response to an antigen, (d) stimulating the activity of immune cells or (e) increasing the vascular permeability. In a further aspect, when the composition comprises an immune inhibiting molecule, the composition is useful for: (a) decreasing infiltration of inflammatory cells into a tissue of a mammal in need thereof, (b) inhibiting or reducing an immune response in a mammal in need thereof, (c) decreasing the activity of immune cells or (d) decreasing the proliferation of immune cells in a mammal in need thereof in response to an antigen. In another aspect, the composition comprises a further active ingredient, which may, for example, be a further antibody or a cytotoxic or chemotherapeutic agent. Preferably, the composition is sterile.

In another embodiment, the invention concerns a method of treating an immune related disorder in a mammal in need thereof, comprising administering to the mammal an effective amount of a PRO87299 polypeptide, an agonist thereof, or an antagonist thereto. In a preferred aspect, the immune related disorder is selected from the group consisting of: systemic lupus erythematosis, rheumatoid arthritis, osteoarthritis, juvenile chronic arthritis, spondyloarthropathies, systemic sclerosis, idiopathic inflammatory myopathies, Sjögren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious, autoimmune chronic active hepatitis, primary biliary cirrhosis, granulomatous hepatitis, and sclerosing cholangitis, inflammatory bowel disease, gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease.

In another embodiment, the invention provides an antibody which specifically binds to any of the above or below described polypeptides. Optionally, the antibody is a monoclonal antibody, humanized antibody, antibody fragment or single-chain antibody. In one aspect, the present invention concerns an isolated antibody which binds a PRO87299 polypeptide. In another aspect, the antibody mimics the activity of a PRO87299 polypeptide (an agonist antibody) or conversely the antibody inhibits or neutralizes the activity of a PRO87299 polypeptide (an antagonist antibody). In another aspect, the antibody is a monoclonal antibody, which preferably has nonhuman complementarity determining region (CDR) residues and human framework region (FR) residues. The antibody may be labeled and may be immobilized on a solid support. In a further aspect, the antibody is an antibody fragment, a monoclonal antibody, a single-chain antibody, or an anti-idiotypic antibody.

In yet another embodiment, the present invention provides a composition comprising an anti-PRO87299 antibody in admixture with a pharmaceutically acceptable carrier. In one aspect, the composition comprises a therapeutically effective amount of the antibody. Preferably, the composition is sterile. The composition may be administered in the form of a liquid pharmaceutical formulation, which may be preserved to achieve extended storage stability. Alternatively, the antibody is a monoclonal antibody, an antibody fragment, a humanized antibody, or a single-chain antibody.

In a further embodiment, the invention concerns an article of manufacture, comprising:

(a) a composition of matter comprising a PRO87299 polypeptide or agonist or antagonist thereof;

(b) a container containing said composition; and (c) a label affixed to said container, or a package insert included in said container referring to the use of said PRO87299 polypeptide or agonist or antagonist thereof in the treatment of an immune related disease. The composition may comprise a therapeutically effective amount of the PRO87299 polypeptide or the agonist or antagonist thereof.

In yet another embodiment, the present invention concerns a method of diagnosing an immune related disease in a mammal, comprising detecting the level of expression of a gene encoding a PRO87299 polypeptide (a) in a test sample of tissue cells obtained from the mammal, and (b) in a control sample of known normal tissue cells of the same cell type, wherein a higher or lower expression level in the test sample as compared to the control sample indicates the presence of immune related disease in the mammal from which the test tissue cells were obtained.

In another embodiment, the present invention concerns a method of diagnosing an immune disease in a mammal, comprising (a) contacting an anti-PRO87299 antibody with a test sample of tissue cells obtained from the mammal, and (b) detecting the formation of a complex between the antibody and a PRO87299 polypeptide, in the test sample; wherein the formation of said complex is indicative of the presence or absence of said disease. The detection may be qualitative or quantitative, and may be performed in comparison with monitoring the complex formation in a control sample of known normal tissue cells of the same cell type. A larger quantity of complexes formed in the test sample indicates the presence or absence of an immune disease in the mammal from which the test tissue cells were obtained. The antibody preferably carries a detectable label. Complex formation can be monitored, for example, by light microscopy, flow cytometry, fluorimetry, or other techniques known in the art. The test sample is usually obtained from an individual suspected of having a deficiency or abnormality of the immune system.

In another embodiment, the invention provides a method for determining the presence of a PRO87299 polypeptide in a sample comprising exposing a test sample of cells suspected of containing the PRO87299 polypeptide to an anti-PRO87299 antibody and determining the binding of said antibody to said cell sample. In a specific aspect, the sample comprises a cell suspected of containing the PRO87299 polypeptide and the antibody binds to the cell. The antibody is preferably detectably labeled and/or bound to a solid support.

In another embodiment, the present invention concerns an immune-related disease diagnostic kit, comprising an anti-PRO87299 antibody and a carrier in suitable packaging. The kit preferably contains instructions for using the antibody to detect the presence of the PRO87299 polypeptide. Preferably the carrier is pharmaceutically acceptable.

In another embodiment, the present invention concerns a diagnostic kit, containing an anti-PRO87299 antibody in suitable packaging. The kit preferably contains instructions for using the antibody to detect the PRO87299 polypeptide.

In another embodiment, the invention provides a method of diagnosing an immune-related disease in a mammal which comprises detecting the presence or absence or a PRO87299 polypeptide in a test sample of tissue cells obtained from said mammal, wherein the presence or absence of the PRO87299 polypeptide in said test sample is indicative of the presence of an immune-related disease in said mammal.

In another embodiment, the present invention concerns a method for identifying an agonist of a PRO87299 polypeptide comprising:

(a) contacting cells and a test compound to be screened under conditions suitable for the induction of a cellular response normally induced by a PRO87299 polypeptide; and (b) determining the induction of said cellular response to determine if the test compound is an effective agonist, wherein the induction of said cellular response is indicative of said test compound being an effective agonist.

In another embodiment, the invention concerns a method for identifying a compound capable of inhibiting the activity of a PRO87299 polypeptide comprising contacting a candidate compound with a PRO87299 polypeptide under conditions and for a time sufficient to allow these two components to interact and determining whether the activity of the PRO87299 polypeptide is inhibited. In a specific aspect, either the candidate compound or the PRO87299 polypeptide is immobilized on a solid support. In another aspect, the non-immobilized component carries a detectable label. In a preferred aspect, this method comprises the steps of:

(a) contacting cells and a test compound to be screened in the presence of a PRO87299 polypeptide under conditions suitable for the induction of a cellular response normally induced by a PRO87299 polypeptide; and (b) determining the induction of said cellular response to determine if the test compound is an effective antagonist.

In another embodiment, the invention provides a method for identifying a compound that inhibits the expression of a PRO87299 polypeptide in cells that normally express the polypeptide, wherein the method comprises contacting the cells with a test compound and determining whether the expression of the PRO87299 polypeptide is inhibited. In a preferred aspect, this method comprises the steps of:

(a) contacting cells and a test compound to be screened under conditions suitable for allowing expression of the PRO87299 polypeptide; and (b) determining the inhibition of expression of said polypeptide.

In yet another embodiment, the present invention concerns a method for treating an immune-related disorder in a mammal that suffers therefrom comprising administering to the mammal a nucleic acid molecule that codes for either (a) a PRO87299 polypeptide, (b) an agonist of a PRO87299 polypeptide or (c) an antagonist of a PRO87299 polypeptide, wherein said agonist or antagonist may be an anti-PRO87299 antibody. In a preferred embodiment, the mammal is human. In another preferred embodiment, the nucleic acid is administered via ex vivo gene therapy. In a further preferred embodiment, the nucleic acid is comprised within a vector, more preferably an adenoviral, adeno-associated viral, lentiviral or retroviral vector.

In yet another aspect, the invention provides a recombinant viral particle comprising a viral vector consisting essentially of a promoter, nucleic acid encoding (a) a PRO87299 polypeptide, (b) an agonist polypeptide of a PRO87299 polypeptide, or (c) an antagonist polypeptide of a PRO87299 polypeptide, and a signal sequence for cellular secretion of the polypeptide, wherein the viral vector is in association with viral structural proteins. Preferably, the signal sequence is from a mammal, such as from a native PRO87299 polypeptide.

In a still further embodiment, the invention concerns an ex vivo producer cell comprising a nucleic acid construct that expresses retroviral structural proteins and also comprises a retroviral vector consisting essentially of a promoter, nucleic acid encoding (a) a PRO87299 polypeptide, (b) an agonist polypeptide of a PRO87299 polypeptide or (c) an antagonist polypeptide of a PRO87299 polypeptide, and a signal sequence for cellular secretion of the polypeptide, wherein said producer cell packages the retroviral vector in association with the structural proteins to produce recombinant retroviral particles.

In a still further embodiment, the invention provides a method of increasing the activity of immune cells in a mammal comprising administering to said mammal (a) a PRO87299 polypeptide, (b) an agonist of a PRO87299 polypeptide, or (c) an antagonist of a PRO87299 polypeptide, wherein the activity of immune cells in the mammal is increased.

In a still further embodiment, the invention provides a method of increasing the proliferation of immune cells in a mammal comprising administering to said mammal (a) a PRO87299 polypeptide, (b) an agonist of a PRO87299 polypeptide, or (c) an antagonist of a PRO87299 polypeptide, wherein the proliferation of immune cells in the mammal is increased.

In a still further embodiment, the invention provides a method of decreasing the proliferation of immune cells in a mammal comprising administering to said mammal (a) a PRO87299 polypeptide, (b) an agonist of a PRO87299 polypeptide, or (c) an antagonist of a PRO87299 polypeptide, wherein the proliferation of immune cells in the mammal is decreased.

B. Additional Embodiments

In other embodiments of the present invention, the invention provides vectors comprising DNA encoding any of the herein described polypeptides. Host cell comprising any such vector are also provided. By way of example, the host cells may be CHO cells, *E. coli*, or yeast. A process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In another embodiment, the invention provides an antibody which specifically binds to any of the above or below described polypeptides. Optionally, the antibody is a monoclonal antibody, humanized antibody, antibody fragment or single-chain antibody.

In yet other embodiments, the invention provides oligonucleotide probes useful for isolating genomic and cDNA nucleotide sequences or as antisense probes, wherein those probes may be derived from any of the above or below described nucleotide sequences.

In other embodiments, the invention provides an isolated nucleic acid molecule comprising a nucleotide sequence that encodes a PRO87299 polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding a PRO87299 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length PRO87299 polypeptide cDNA as disclosed herein, the coding sequence of a PRO87299 polypeptide lacking the signal peptide as disclosed herein, the coding sequence of an extracellular domain of a transmembrane PRO87299 polypeptide, with or without the signal peptide, as disclosed herein or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to a DNA molecule that encodes the same mature polypeptide as shown in FIG. 2 (SEQ ID NO:2).

Another aspect the invention provides an isolated nucleic acid molecule comprising a nucleotide sequence encoding a PRO87299 polypeptide which is either transmembrane domain-deleted or transmembrane domain-inactivated, or is complementary to such encoding nucleotide sequence, wherein the transmembrane domain(s) of such polypeptide are disclosed herein. Therefore, soluble extracellular domains of the herein described PRO87299 polypeptides are contemplated.

Another embodiment is directed to fragments of a PRO87299 polypeptide coding sequence, or the complement thereof, that may find use as, for example, hybridization probes, for encoding fragments of a PRO87299 polypeptide that may optionally encode a polypeptide comprising a binding site for an anti-PRO87299 antibody or as antisense oligonucleotide probes. Such nucleic acid fragments are usually at least about 20 nucleotides in length, alternatively at least about 30 nucleotides in length, alternatively at least about 40 nucleotides in length, alternatively at least about 50 nucleotides in length, alternatively at least about 60 nucleotides in length, alternatively at least about 70 nucleotides in length, alternatively at least about 80 nucleotides in length, alternatively at least about 90 nucleotides in length, alternatively at least about 100 nucleotides in length, alternatively at least about 110 nucleotides in length, alternatively at least about 120 nucleotides in length, alternatively at least about 130 nucleotides in length, alternatively at least about 140 nucleotides in length, alternatively at least about 150 nucleotides in length, alternatively at least about 160 nucleotides in length, alternatively at least about 170 nucleotides in length, alternatively at least about 180 nucleotides in length, alternatively at least about 190 nucleotides in length, alternatively at least about 200 nucleotides in length, alternatively at least about 250 nucleotides in length, alternatively at least about 300 nucleotides in length, alternatively at least about 350 nucleotides in length, alternatively at least about 400 nucleotides in length, alternatively at least about 450 nucleotides in length, alternatively at least about 500 nucleotides in length, alternatively at least about 600 nucleotides in length, alternatively at least about 700 nucleotides in length, alternatively at least about 800 nucleotides in length, alternatively at least about 900 nucleotides in length and alternatively at least about 1000 nucleotides in length, wherein in this context the term "about" means the referenced nucleotide sequence length plus or minus 10% of that referenced length. It is noted that novel fragments of a PRO87299 polypeptide-encoding nucleotide sequence may be determined in a routine manner by aligning the PRO87299 polypeptide-encoding nucleotide sequence with other known nucleotide sequences using any of a number of well known sequence alignment programs and determining which PRO87299 polypeptide-encoding nucleotide sequence fragment(s) are novel. All of such PRO87299 polypeptide-encoding nucleotide sequences are contemplated herein. Also contemplated are the PRO87299 polypeptide fragments encoded by these nucleotide molecule fragments, preferably those PRO87299 polypeptide fragments that comprise a binding site for an anti-PRO87299 antibody.

In another embodiment, the invention provides isolated PRO87299 polypeptide encoded by any of the isolated nucleic acid sequences herein above identified.

In a certain aspect, the invention concerns an isolated PRO87299 polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a PRO87299 polypeptide having a full-length amino acid sequence as disclosed herein, an amino acid sequence lacking the signal peptide as disclosed herein, an extracellular domain of a transmembrane protein, with or without the signal peptide, as disclosed herein or any other specifically defined fragment of the full-length amino acid sequence as disclosed herein.

In a further aspect, the invention concerns an isolated PRO87299 polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence shown in FIG. 2 (SEQ ID NO:2).

In a specific aspect, the invention provides an isolated PRO87299 polypeptide without the N-terminal signal sequence and/or the initiating methionine and is encoded by a nucleotide sequence that encodes such an amino acid sequence as herein before described. Processes for producing the same are also herein described, wherein those processes comprise culturing a host cell comprising a vector which comprises the appropriate encoding nucleic acid molecule under conditions suitable for expression of the PRO87299 polypeptide and recovering the PRO87299 polypeptide from the cell culture.

Another aspect the invention provides an isolated PRO87299 polypeptide which is either transmembrane domain-deleted or transmembrane domain-inactivated. Processes for producing the same are also herein described, wherein those processes comprise culturing a host cell comprising a vector which comprises the appropriate encoding nucleic acid molecule under conditions suitable for expression of the PRO87299 polypeptide and recovering the PRO87299 polypeptide from the cell culture.

In yet another embodiment, the invention concerns agonists and antagonists of a native PRO87299 polypeptide as defined herein. In a particular embodiment, the agonist or antagonist is an anti-PRO87299 antibody or a small molecule.

In a further embodiment, the invention concerns a method of identifying agonists or antagonists to a PRO87299 polypeptide which comprise contacting the PRO87299 polypeptide with a candidate molecule and monitoring a biological activity mediated by said PRO87299 polypeptide. Preferably, the PRO87299 polypeptide is a native PRO87299 polypeptide.

In a still further embodiment, the invention concerns a composition of matter comprising a PRO87299 polypeptide, or an agonist or antagonist of a PRO87299 polypeptide as herein described, or an anti-PRO87299 antibody, in combination with a carrier. Optionally, the carrier is a pharmaceutically acceptable carrier.

Another embodiment of the present invention is directed to the use of a PRO87299 polypeptide, or an agonist or antagonist thereof as herein before described, or an anti-PRO87299 antibody, for the preparation of a medicament useful in the treatment of a condition which is responsive to the PRO87299 polypeptide, an agonist or antagonist thereof or an anti-PRO87299 antibody.

BRIEF DESCRIPTION OF THE DRAWINGS

FIG. 1 shows a nucleotide sequence (SEQ ID NO:1) of a native sequence PRO87299 cDNA, wherein SEQ ID NO:1 is a clone designated herein as "DNA332467".

FIG. 2 shows the amino acid sequence (SEQ ID NO:2) derived from the coding sequence of SEQ ID NO:1 shown in FIG. 1.

FIG. 3 shows a nucleotide sequence (SEQ ID NO:3) of a native sequence HVEM cDNA (HVEM), wherein SEQ ID NO:3 is a clone designated herein as "HVEM."

FIG. 4 shows the amino acid sequence (SEQ ID NO:4) derived from the coding sequence of SEQ ID NO:3 shown in FIG. 3.

FIG. 5 shows a nucleotide sequence (SEQ ID NO:5) of a native sequence LIGHT, wherein SEQ ID NO:5 is a clone designated herein as "LIGHT."

FIG. 6 shows the amino acid sequence (SEQ ID NO:6) derived from the coding sequence of SEQ ID NO:5 shown in FIG. 5.

FIG. 7 shows a nucleotide sequence (SEQ ID NO:7) of a variant sequence PRO87299, wherein SEQ ID NO:7 is a clone designated herein as "PRO87299.short."

FIG. 8 shows the amino acid sequence (SEQ ID NO:8) derived from the coding sequence of SEQ ID NO:7 shown in FIG. 7.

FIG. 9 shows a nucleotide sequence (SEQ ID NO:9) of a variant sequence PRO87299, wherein SEQ ID NO:9 is a clone designated herein as "PRO87299.AFTNIP."

FIG. 10 shows the amino acid sequence (SEQ ID NO:10) derived from the coding sequence of SEQ ID NO:9 shown in FIG. 9.

FIG. 11 shows nucleic acid variants of PRO87299 cDNA.

FIG. 12 shows the polypeptide translation of PRO87299 variants.

FIG. 20 shows that PRO87299 is not blocked by LIGHT interacting with HVEM.

DETAILED DESCRIPTION OF THE PREFERRED EMBODIMENTS

I. Definitions

Figure 13:
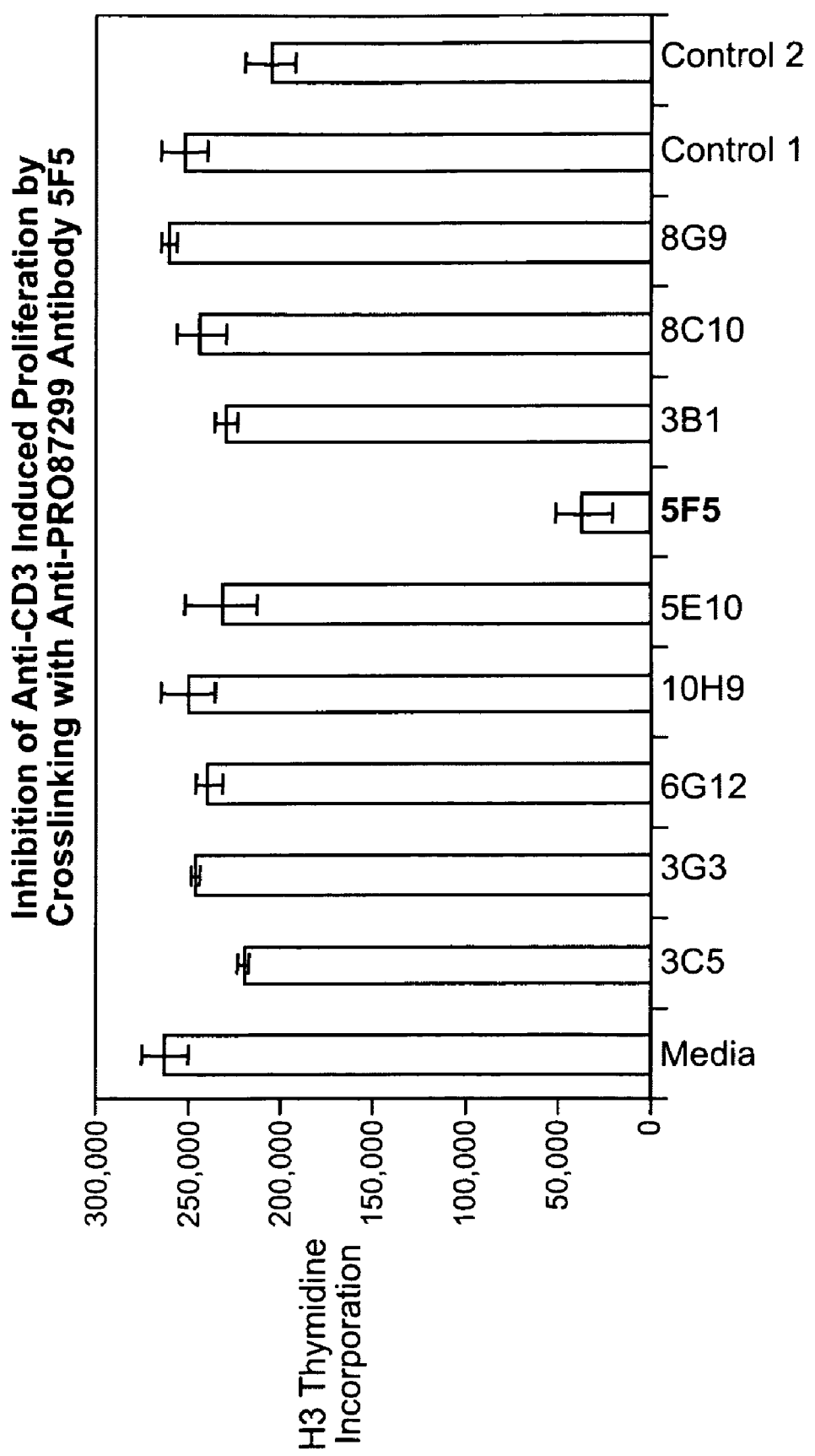
FIG. 13 shows inhibition of CD4+ T cell proliferation by agonist antibodies.

The PRO87299 polypeptides described herein may be isolated from a variety of sources, such as from human tissue types or from another source, or prepared by recombinant or synthetic methods. All disclosures in this specification which refer to the "PRO87299 polypeptide" refer to each of the polypeptides individually as well as jointly. For example, descriptions of the preparation of, purification of, derivation of, formation of antibodies to or against, administration of, compositions containing, treatment of a disease with, etc., pertain to each polypeptide of the invention individually. The term "PRO87299 polypeptide" also includes variants of the PRO87299 polypeptides disclosed herein.

A "native sequence PRO87299 polypeptide" comprises a polypeptide having the same amino acid sequence as the corresponding PRO87299 polypeptide derived from nature. Such native sequence PRO87299 polypeptides can be isolated from nature or can be produced by recombinant or synthetic means. The term "native sequence PRO87299 polypeptide" specifically encompasses naturally-occurring truncated or secreted forms of the specific PRO87299 polypeptide (e.g., an extracellular domain sequence), naturally-occurring variant forms (e.g., alternatively spliced forms) and naturally-occurring allelic variants of the polypeptide. In various embodiments of the invention, the native sequence PRO87299 polypeptides disclosed herein are mature or full-length native sequence polypeptides comprising the full-length amino acids sequences shown in the accompanying figures. Start and stop codons are shown in bold font and underlined in the figures. However, while the PRO87299 polypeptide disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the PRO87299 polypeptides.

The PRO87299 polypeptide "extracellular domain" or "ECD" refers to a form of the PRO87299 polypeptide which is essentially free of the transmembrane and cytoplasmic domains. Ordinarily, a PRO87299 polypeptide ECD will have less than 1% of such transmembrane and/or cytoplasmic domains and preferably, will have less than 0.5% of such domains. It will be understood that any transmembrane domains identified for the PRO87299 polypeptides of the present invention are identified pursuant to criteria routinely employed in the art for identifying that type of hydrophobic domain. The exact boundaries of a transmembrane domain may vary but most likely by no more than about 5 amino acids at either end of the domain as initially identified herein. Optionally, therefore, an extracellular domain of a PRO87299 polypeptide may contain from about 5 or fewer amino acids on either side of the transmembrane domain/extracellular domain boundary as identified in the Examples or specification and such polypeptides, with or without the associated signal peptide, and nucleic acid encoding them, are contemplated by the present invention.

"PRO87299 polypeptide variant" means an active PRO87299 polypeptide as defined above or below having at least about 80% amino acid sequence identity with a full-length native sequence PRO87299 polypeptide sequence as disclosed herein, a PRO87299 polypeptide sequence lacking the signal peptide as disclosed herein, an extracellular domain of a PRO87299 polypeptide, with or without the signal peptide, as disclosed herein or any other fragment of a full-length PRO87299 polypeptide sequence as disclosed herein. Such PRO87299 polypeptide variants include, for instance, PRO87299 polypeptides wherein one or more amino acid residues are added, or deleted, at the N- or C-terminus of the full-length native amino acid sequence. Ordinarily, a PRO87299 polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence PRO87299 polypeptide sequence as disclosed herein, a PRO87299 polypeptide sequence lacking the signal peptide as disclosed herein, an extracellular domain of a PRO87299 polypeptide, with or without the signal peptide, as disclosed herein or any other specifically defined fragment of a full-length PRO87299 polypeptide sequence as disclosed herein. Ordinarily, PRO87299 variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the PRO87299 polypeptide sequences identified herein is defined as the percentage of amino acid residues in a candidate sequence that are identical with the amino acid residues in the specific PRO87299 polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "PRO87299", wherein "PRO87299" represents the amino acid sequence of a hypothetical PRO87299 polypeptide of interest, "Comparison Protein" represents the amino acid sequence of a polypeptide against which the "PRO87299" polypeptide of interest is being compared, and "X", "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the PRO87299 polypeptide of interest having a sequence derived from the native PRO87299 polypeptide and the comparison amino acid sequence of interest (i.e., the sequence against which the PRO87299 polypeptide of interest is being compared which may be a PRO87299 variant polypeptide) as determined by WU-BLAST-2 by (b) the total number of amino acid residues of the PRO87299 polypeptide of interest. For example, in the statement "a polypeptide comprising an the amino acid sequence A which has or having at least 80% amino acid sequence identity to the amino acid sequence B", the amino acid sequence A is the comparison amino acid sequence of interest and the amino acid sequence B is the amino acid sequence of the PRO87299 polypeptide of interest.

Percent amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multipass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"PRO87299 variant polynucleotide" or "PRO87299 variant nucleic acid sequence" means a nucleic acid molecule which encodes an active PRO87299 polypeptide as defined below and which has at least about 80% nucleic acid sequence identity with a nucleotide acid sequence encoding a full-length native sequence PRO87299 polypeptide sequence as disclosed herein, a full-length native sequence PRO87299 polypeptide sequence lacking the signal peptide as disclosed herein, an extracellular domain of a PRO87299 polypeptide, with or without the signal peptide, as disclosed herein or any other fragment of a full-length PRO87299 polypeptide sequence as disclosed herein. Ordinarily, a PRO87299 variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence PRO87299 polypeptide sequence as disclosed herein, a full-length native sequence PRO87299 polypeptide sequence lacking the signal peptide as disclosed herein, an extracellular domain of a PRO87299 polypeptide, with or without the signal sequence, as disclosed herein or any other fragment of a full-length PRO87299 polypeptide sequence as disclosed herein. Variants do not encompass the native nucleotide sequence.

Ordinarily, PRO87299 variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to PRO87299-encoding nucleic acid sequences identified herein is defined as the percentage of nucleotides in a candidate sequence that are identical with the nucleotides in the PRO87299 nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNAS-TAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "PRO87299-DNA", wherein "PRO87299-DNA" represents a hypothetical PRO87299-encoding nucleic acid sequence of interest, "Comparison DNA" represents the nucleotide sequence of a nucleic acid molecule against which the "PRO87299-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., Methods in Enzymology 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % nucleic acid sequence identity value is determined by dividing (a) the number of matching identical nucleotides between the nucleic acid sequence of the PRO87299 polypeptide-encoding nucleic acid molecule of interest having a sequence derived from the native sequence PRO87299 polypeptide-encoding nucleic acid and the comparison nucleic acid molecule of interest (i.e., the sequence against which the PRO87299 polypeptide-encoding nucleic acid molecule of interest is being compared which may be a variant PRO87299 polynucleotide) as determined by WU-BLAST-2 by (b) the total number of nucleotides of the PRO87299 polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the PRO87299 polypeptide-encoding nucleic acid molecule of interest.

Percent nucleic acid sequence identity may also be determined using the sequence comparison program NCBI-BLAST2 (Altschul et al., Nucleic Acids Res. 25:3389-3402 (1997)). The NCBI-BLAST2 sequence comparison program may be obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, PRO87299 variant polynucleotides are nucleic acid molecules that encode an active PRO87299 polypeptide and which are capable of hybridizing, preferably under stringent hybridization and wash conditions, to nucleotide sequences encoding a full-length PRO87299 polypeptide as disclosed herein. PRO87299 variant polypeptides may be those that are encoded by a PRO87299 variant polynucleotide.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the PRO87299 polypeptide natural environment will not be present. Ordinarily, however, isolated polypeptide will be prepared by at least one purification step.

An "isolated" PRO87299 polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "antibody" is used in the broadest sense and specifically covers, for example, single anti-PRO87299 monoclonal antibodies (including agonist, antagonist, and neutralizing antibodies), anti-PRO87299 antibody compositions with polyepitopic specificity, single chain anti-PRO87299 antibodies, and fragments of anti-PRO87299 antibodies (see below). The term "monoclonal antibody" as used herein refers to an antibody obtained from a population of substantially homogeneous antibodies, i.e., the individual antibodies comprising the population are identical except for possible naturally-occurring mutations that may be present in minor amounts.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/ 0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising a PRO87299 polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Active" or "activity" for the purposes herein refers to form(s) of a PRO87299 polypeptide which retain a biological and/or an immunological activity of native or naturally-occurring PRO87299, wherein "biological" activity refers to a biological function (either inhibitory or stimulatory) caused by a native or naturally-occurring PRO87299 other than the ability to induce the production of an antibody against an antigenic epitope possessed by a native or naturally-occurring PRO87299 and an "immunological" activity refers to the ability to induce the production of an antibody against an antigenic epitope possessed by a native or naturally-occurring PRO87299.

The term "antagonist" is used in the broadest sense, and includes any molecule that partially or fully blocks, inhibits, or neutralizes a biological activity of a native PRO87299 polypeptide disclosed herein. In a similar manner, the term "agonist" is used in the broadest sense and includes any molecule that mimics a biological activity of a native PRO87299 polypeptide disclosed herein. Suitable agonist or antagonist molecules specifically include agonist or antagonist antibodies or antibody fragments, fragments or amino acid sequence variants of native PRO87299 polypeptides, peptides, antisense oligonucleotides, small organic molecules, etc. Methods for identifying agonists or antagonists of a PRO87299 polypeptide may comprise contacting a PRO87299 polypeptide with a candidate agonist or antagonist molecule and measuring a detectable change in one or more biological activities normally associated with the PRO87299 polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An antibody that "specifically binds to" or is "specific for" a particular polypeptide or an epitope on a particular polypeptide is one that binds to that particular polypeptide or epitope on a particular polypeptide without substantially binding to any other polypeptide or polypeptide epitope.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as a PRO87299 polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, etc.

The term "T cell mediated disease" means a disease in which T cells directly or indirectly mediate or otherwise contribute to a morbidity in a mammal. The T cell mediated disease may be associated with cell mediated effects, lymphokine mediated effects, etc., and even effects associated with B cells if the B cells are stimulated, for example, by the lymphokines secreted by T cells.

Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases including viral diseases such as AIDS (HIV infection), hepatitis A, B, C, D, and E, herpes, etc., bacterial infections, fungal infections, protozoal infections and parasitic infections.

The term "effective amount" is a concentration or amount of a PRO87299 polypeptide and/or agonist/antagonist which results in achieving a particular stated purpose. An "effective amount" of a PRO87299 polypeptide or agonist or antagonist thereof may be determined empirically. Furthermore, a "therapeutically effective amount" is a concentration or amount of a PRO87299 polypeptide and/or agonist/antagonist which is effective for achieving a stated therapeutic effect. This amount may also be determined empirically.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells. Cytotoxins may be covalently attached to an antibody to target the toxin to a particular cell of interest which expresses the antigen. Useful cytotoxins are their linker include, without limitation, the following:

Linkers:

MC=maleimidocaproyl

Val Cit=valine-citrulline, dipeptide site in protease cleavable linker.

Citrulline=2-amino-5-ureido pentanoic acid

PAB=p-aminobenzylcarbamoyl ("self immolative" portion of linker)

Me=N-methyl-valine citrulline where the linker peptide bond has been modified to prevent its cleavage by cathepsin B MC(PEG)$_6$-OH=maleimidocaproyl-polyethylene glycol, attached to antibody cysteines.

SPP=N-Succinimidyl 4-(2-pyridylthio)pentanoate

SMCC=N-Succinimidyl 4-(N-maleimidomethyl)cyclohexane-1 carboxylate

Cytotoxic Drugs:

MMAE=mono-methyl auristatin E (MW 718)

MMAF=variant of auristatin E (MMAE) with a phenylalanine at the C-terminus of the drug (MW 731.5)

MMAF-DMAEA=MMAF with DMAEA (dimethylaminoethylamine) in an amide linkage to the C-terminal phenylalanine (MW 801.5)

MMAF-TEG=MMAF with tetraethylene glycol esterified to the phenylalanine

MMAF-NtBu=N-t-butyl, attached as an amide to C-terminus of MMAF

AEVB=auristatin E valeryl benzylhydrazone, acid labile linker through the C-terminus of AE (MW 732)

AFP=Auristatin F phenylene diamine; (the phenylalanine variant linked to the antibody through the C-terminus via a phenylene diamine spacer) (MW 732).

A "growth inhibitory agent" when used herein refers to a compound or composition which inhibits growth of a cell, either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhône-Poulenc Rorer, Antony, France), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, caminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors such as tamoxifen and onapristone.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

As used herein, the term "inflammatory cells" designates cells that enhance the inflammatory response such as mononuclear cells, eosinophils, macrophages, and polymorphonuclear neutrophils (PMN).

Table 1

```
/*
 *
 * C-C increased from 12 to 15
 * Z is average of EQ
 * B is average of ND
 * match with stop is _M; stop-stop = 0; J (joker) match = 0
 */
define   _M      -8          /* value of a match with a stop */ int       _day[26][26] = {
/*        A  B  C  D  E  F  G  H  I  J  K  L  M  N  O  P  Q  R  S  T  U  V  W  X  Y  Z */
/* A */   { 2, 0,-2, 0, 0,-4, 1,-1,-1, 0,-1,-2,-1, 0,_M, 1, 0,-2, 1, 1, 0, 0,-6, 0,-3, 0},
/* B */   { 0, 3,-4, 3, 2,-5, 0, 1,-2, 0, 0,-3,-2, 2,_M,-1, 1, 0, 0, 0, 0,-2,-5, 0,-3, 1},
/* C */   {-2,-4,15,-5,-5,-4,-3,-3,-2, 0,-5,-6,-5,-4,_M,-3,-5,-4, 0,-2, 0,-2,-8, 0, 0,-5},
/* D */   { 0, 3,-5, 4, 3,-6, 1, 1,-2, 0, 0,-4,-3, 2,_M,-1, 2,-1, 0, 0, 0,-2,-7, 0,-4, 2},
/* E */   { 0, 2,-5, 3, 4,-5, 0, 1,-2, 0, 0,-3,-2, 1,_M,-1, 2,-1, 0, 0, 0,-2,-7, 0,-4, 3},
/* F */   {-4,-5,-4,-6,-5, 9,-5,-2, 1, 0,-5, 2, 0,-4,_M,-5,-5,-4,-3,-3, 0,-1, 0, 0, 7,-5},
/* G */   { 1, 0,-3, 1, 0,-5, 5,-2,-3, 0,-2,-4,-3, 0,_M,-1,-1,-3, 1, 0, 0,-1,-7, 0,-5, 0},
/* H */   {-1, 1,-3, 1, 1,-2,-2, 6,-2, 0, 0,-2,-2, 2,_M, 0, 3, 2,-1,-1, 0,-2,-3, 0, 0, 2},
/* I */   {-1,-2,-2,-2,-2, 1,-3,-2, 5, 0,-2, 2, 2,-2,_M,-2,-2,-2,-1, 0, 0, 4,-5, 0,-1,-2},
/* J */   { 0, 0, 0, 0, 0, 0, 0, 0, 0, 0, 0, 0, 0, 0,_M, 0, 0, 0, 0, 0, 0, 0, 0, 0, 0, 0},
/* K */   {-1, 0,-5, 0, 0,-5,-2, 0,-2, 0, 5,-3, 0, 1,_M,-1, 1, 3, 0, 0, 0,-2,-3, 0,-4, 0},
/* L */   {-2,-3,-6,-4,-3, 2,-4,-2, 2, 0,-3, 6, 4,-3,_M,-3,-2,-3,-3,-1, 0, 2,-2, 0,-1,-2},
/* M */   {-1,-2,-5,-3,-2, 0,-3,-2, 2, 0, 0, 4, 6,-2,_M,-2,-1, 0,-2,-1, 0, 2,-4, 0,-2,-1},
/* N */   { 0, 2,-4, 2, 1,-4, 0, 2,-2, 0, 1,-3,-2, 2,_M,-1, 1, 0, 1, 0, 0,-2,-4, 0,-2, 1},
/* O */   {_M,_M,_M,_M,_M,_M,_M,_M,_M,_M,_M,_M,_M,_M,
0,_M,_M,_M,_M,_M,_M,_M,_M,_M,_M,_M},
/* P */   { 1,-1,-3,-1,-1,-5,-1, 0,-2, 0,-1,-3,-2,-1,_M, 6, 0, 0, 1, 0, 0,-1,-6, 0,-5, 0},
/* Q */   { 0, 1,-5, 2, 2,-5,-1, 3,-2, 0, 1,-2,-1, 1,_M, 0, 4, 1,-1,-1, 0,-2,-5, 0,-4, 3},
/* R */   {-2, 0,-4,-1,-1,-4,-3, 2,-2, 0, 3,-3, 0, 0,_M, 0, 1, 6, 0,-1, 0,-2, 2, 0,-4, 0},
/* S */   { 1, 0, 0, 0, 0,-3, 1,-1,-1, 0, 0,-3,-2, 1,_M, 1,-1, 0, 2, 1, 0,-1,-2, 0,-3, 0},
/* T */   { 1, 0,-2, 0, 0,-3, 0,-1, 0, 0, 0,-1,-1, 0,_M, 0,-1,-1, 1, 3, 0, 0,-5, 0,-3, 0},
/* U */   { 0, 0, 0, 0, 0, 0, 0, 0, 0, 0, 0, 0, 0, 0,_M, 0, 0, 0, 0, 0, 0, 0, 0, 0, 0, 0},
/* V */   { 0,-2,-2,-2,-2,-1,-1,-2, 4, 0,-2, 2, 2,-2,_M,-1,-2,-2,-1, 0, 0, 4,-6, 0,-2,-2},
/* W */   {-6,-5,-8,-7,-7, 0,-7,-3,-5, 0,-3,-2,-4,-4,_M,-6,-5, 2,-2,-5, 0,-6,17, 0, 0,-6},
/* X */   { 0, 0, 0, 0, 0, 0, 0, 0, 0, 0, 0, 0, 0, 0,_M, 0, 0, 0, 0, 0, 0, 0, 0, 0, 0, 0},
/* Y */   {-3,-3, 0,-4,-4, 7,-5, 0,-1, 0,-4,-1,-2,-2,_M,-5,-4,-4,-3,-3, 0,-2, 0, 0,10,-4},
/* Z */   { 0, 1,-5, 2, 3,-5, 0, 2,-2, 0, 0,-2,-1, 1,_M, 0, 3, 0, 0, 0, 0,-2,-6, 0,-4, 4}
};
```

Table 1 (cont')

```
/*
*/
#include <stdio.h>
include <ctype.h> define  MAXJMP   16     /* max jumps in a diag */
define  MAXGAP   24     /* don't continue to penalize gaps larger than this */
#define  JMPS     1024   /* max jmps in an path */
define  MX       4      /* save if there's at least MX-1 bases since last jmp */ define  DMAT     3      /* value of matching bases */
define  DMIS     0      /* penalty for mismatched bases */
#define  DINS0    8      /* penalty for a gap */
#define  DINS1    1      /* penalty per base */
#define  PINS0    8      /* penalty for a gap */
define  PINS1    4      /* penalty per residue */ struct jmp {
        short           n[MAXJMP];      /* size of jmp (neg for dely) */
        unsigned short  x[MAXJMP];      /* base no. of jmp in seq x */
};                                      /* limits seq to 2^16 -1 */ struct diag {
        int             score;          /* score at last jmp */
        long            offset;         /* offset of prev block */
        short           ijmp;           /* current jmp index */
        struct jmp      jp;             /* list of jmps */
};

struct path {
        int             spc;            /* number of leading spaces */
        short           n[JMPS];        /* size of jmp (gap) */
        int             x[JMPS];        /* loc of jmp (last elem before gap) */
};

char            *ofile;                 /* output file name */
char            *namex[2];              /* seq names: getseqs() */
char            *prog;                  /* prog name for err msgs */
char            *seqx[2];               /* seqs: getseqs() */
int             dmax;                   /* best diag: nw() */
int             dmax0;                  /* final diag */
int             dna;                    /* set if dna: main() */
int             endgaps;                /* set if penalizing end gaps */
int             gapx, gapy;             /* total gaps in seqs */
int             len0, len1;             /* seq lens */
int             ngapx, ngapy;           /* total size of gaps */
int             smax;                   /* max score: nw() */
int             *xbm;                   /* bitmap for matching */
long            offset;                 /* current offset in jmp file */
struct  diag    *dx;                    /* holds diagonals */
struct  path    pp[2];                  /* holds path for seqs */ char            *calloc(), *malloc(), *index(), *strcpy();
char            *getseq(), *g_calloc();
```

Table 1 (cont')

```
/* Needleman-Wunsch alignment program
 *
 * usage: progs file1 file2
 *   where file1 and file2 are two dna or two protein sequences.
 *   The sequences can be in upper- or lower-case an may contain ambiguity
 *   Any lines beginning with ';', '>' or '<' are ignored
 *   Max file length is 65535 (limited by unsigned short x in the jmp struct)
 *   A sequence with 1/3 or more of its elements ACGTU is assumed to be DNA
 *   Output is in the file "align.out"
 *
 * The program may create a tmp file in /tmp to hold info about traceback.
 * Original version developed under BSD 4.3 on a vax 8650
 */
include "nw.h"
#include "day.h"

static    _dbval[26] = {
          1,14,2,13,0,0,4,11,0,0,12,0,3,15,0,0,0,5,6,8,8,7,9,0,10,0
};

static    _pbval[26] = {
          1, 2|(1<<('D'-'A'))|(1<<('N'-'A')), 4, 8, 16, 32, 64,
          128, 256, 0xFFFFFFFF, 1<<10, 1<<11, 1<<12, 1<<13, 1<<14,
          1<<15, 1<<16, 1<<17, 1<<18, 1<<19, 1<<20, 1<<21, 1<<22,
          1<<23, 1<<24, 1<<25|(1<<('E'-'A'))|(1<<('Q'-'A'))
};

main(ac, av)
          main
          int       ac;
          char      *av[ ];
{
          prog = av[0];
          if (ac != 3) {
                    fprintf(stderr,"usage: %s file1 file2\n", prog);
                    fprintf(stderr,"where file1 and file2 are two dna or two protein sequences.\n");
                    fprintf(stderr,"The sequences can be in upper- or lower-case\n");
                    fprintf(stderr,"Any lines beginning with ';' or '<' are ignored\n");
                    fprintf(stderr,"Output is in the file \"align.out\"\n");
                    exit(1);
          }
          namex[0] = av[1];
          namex[1] = av[2];
          seqx[0] = getseq(namex[0], &len0);
          seqx[1] = getseq(namex[1], &len1);
          xbm = (dna)? _dbval : _pbval;

endgaps = 0;              /* 1 to penalize endgaps */
          ofile = "align.out";      /* output file */ nw();                     /* fill in the matrix, get the possible jmps */
          readjmps();               /* get the actual jmps */
          print();                  /* print stats, alignment */ cleanup(0);               /* unlink any tmp files */
}
```

Table 1 (cont')

```
/* do the alignment, return best score: main()
 * dna: values in Fitch and Smith, PNAS, 80, 1382-1386, 1983
 * pro: PAM 250 values
 * When scores are equal, we prefer mismatches to any gap, prefer
 * a new gap to extending an ongoing gap, and prefer a gap in seqx
 * to a gap in seq y.
 */
nw()
        nw
{
        char            *px, *py;           /* seqs and ptrs */
        int             *ndely, *dely;      /* keep track of dely */
        int             ndelx, delx;        /* keep track of delx */
        int             *tmp;               /* for swapping row0, row1 */
        int             mis;                /* score for each type */
        int             ins0, ins1;         /* insertion penalties */
        register        id;                 /* diagonal index */
        register        ij;                 /* jmp index */
        register        *col0, *col1;       /* score for curr, last row */
        register        xx, yy;             /* index into seqs */ dx = (struct diag *)g_calloc("to get diags", len0+len1+1, sizeof(struct diag));

ndely = (int *)g_calloc("to get ndely", len1+1, sizeof(int));
        dely  = (int *)g_calloc("to get dely",  len1+1, sizeof(int));
        col0  = (int *)g_calloc("to get col0",  len1+1, sizeof(int));
        col1  = (int *)g_calloc("to get col1",  len1+1, sizeof(int));
        ins0 = (dna)? DINS0 : PINS0;
        ins1 = (dna)? DINS1 : PINS1;

smax = -10000;
        if (endgaps) {
                for (col0[0] = dely[0] = -ins0, yy = 1; yy <= len1; yy++) {
                        col0[yy] = dely[yy] = col0[yy-1] - ins1;
                        ndely[yy] = yy;
                }
                col0[0] = 0;            /* Waterman Bull Math Biol 84 */
        }
        else
                for (yy = 1; yy <= len1; yy++)
                        dely[yy] = -ins0;

/* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = -(ins0+ins1);
                        else
                                col1[0] = delx = col0[0] - ins1;
                        ndelx = xx;
                }
                else {
                        col1[0] = 0;
                        delx = -ins0;
                        ndelx = 0;
                }
```

Table 1 (cont')

...nw

```
for (py = seqx[1], yy = 1; yy <= len1; py++, yy++) {
        mis = col0[yy-1];
        if (dna)
                mis += (xbm[*px-'A']&xbm[*py-'A'])? DMAT : DMIS;
        else
                mis += _day[*px-'A'][*py-'A'];

/* update penalty for del in x seq;
         * favor new del over ongong del
         * ignore MAXGAP if weighting endgaps
         */
        if (endgaps || ndely[yy] < MAXGAP) {
                if (col0[yy] - ins0 >= dely[yy]) {
                        dely[yy] = col0[yy] - (ins0+ins1);
                        ndely[yy] = 1;
                } else {
                        dely[yy] -= ins1;
                        ndely[yy]++;
                }
        } else {
                if (col0[yy] - (ins0+ins1) >= dely[yy]) {
                        dely[yy] = col0[yy] - (ins0+ins1);
                        ndely[yy] = 1;
                } else
                        ndely[yy]++;
        }

/* update penalty for del in y seq;
         * favor new del over ongong del
         */
        if (endgaps || ndelx < MAXGAP) {
                if (col1[yy-1] - ins0 >= delx) {
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }

/* pick the maximum score; we're favoring
         * mis over any del and delx over dely
         */
```

Table 1 (cont')

...nw

```
            id = xx - yy + len1 - 1;
            if (mis > = delx && mis > = dely[yy])
                    col1[yy] = mis;
            else if (delx > = dely[yy]) {
                    col1[yy] = delx;
                    ij = dx[id].ijmp;
                    if (dx[id].jp.n[0] && (!dna || (ndelx > = MAXJMP
                            && xx > dx[id].jp.x[ij]+MX) || mis > dx[id].score+DINS0)) {
                            dx[id].ijmp++;
                            if (++ij > = MAXJMP) {
                                    writejmps(id);
                                    ij = dx[id].ijmp = 0;
                                    dx[id].offset = offset;
                                    offset += sizeof(struct jmp) + sizeof(offset);
                            }
                    }
                    dx[id].jp.n[ij] = ndelx;
                    dx[id].jp.x[ij] = xx;
                    dx[id].score = delx;
            }
            else {
                    col1[yy] = dely[yy];
                    ij = dx[id].ijmp;
    if (dx[id].jp.n[0] && (!dna || (ndely[yy] > = MAXJMP
            && xx > dx[id].jp.x[ij]+MX) || mis > dx[id].score+DINS0)) {
                            dx[id].ijmp++;
                            if (++ij > = MAXJMP) {
                                    writejmps(id);
                                    ij = dx[id].ijmp = 0;
                                    dx[id].offset = offset;
                                    offset += sizeof(struct jmp) + sizeof(offset);
                            }
                    }
                    dx[id].jp.n[ij] = -ndely[yy];
                    dx[id].jp.x[ij] = xx;
                    dx[id].score = dely[yy];
            }
            if (xx == len0 && yy < len1) {
                    /* last col
                    */
                    if (endgaps)
                            col1[yy] -= ins0+ins1*(len1-yy);
                    if (col1[yy] > smax) {
                            smax = col1[yy];
                            dmax = id;
                    }
            }
    }
    if (endgaps && xx < len0)
            col1[yy-1] -= ins0+ins1*(len0-xx);
    if (col1[yy-1] > smax) {
            smax = col1[yy-1];
            dmax = id;
    }
    tmp = col0; col0 = col1; col1 = tmp;
}
(void) free((char *)ndely);
(void) free((char *)dely);
(void) free((char *)col0);
(void) free((char *)col1);                                  }
```

Table 1 (cont')

```
/*
 *
 * print() -- only routine visible outside this module
 *
 * static:
 * getmat() -- trace back best path, count matches: print()
 * pr_align() -- print alignment of described in array p[ ]: print()
 * dumpblock() -- dump a block of lines with numbers, stars: pr_align()
 * nums() -- put out a number line: dumpblock()
 * putline() -- put out a line (name, [num], seq, [num]): dumpblock()
 * stars() - -put a line of stars: dumpblock()
 * stripname() -- strip any path and prefix from a seqname
 */ include "nw.h"

define SPC      3
#define P_LINE   256   /* maximum output line */
define P_SPC    3     /* space between name or num and seq */ extern   _day[26][26];
int      olen;         /* set output line length */
FILE     *fx;          /* output file */ print()
``` print

```
{
        int     lx, ly, firstgap, lastgap;      /* overlap */ if ((fx = fopen(ofile, "w")) = = 0) {
                fprintf(stderr,"%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) {          /* leading gap in x */
                pp[0].spc = firstgap = len1 - dmax - 1;
                ly -= pp[0].spc;
        }
        else if (dmax > len1 - 1) {     /* leading gap in y */
                pp[1].spc = firstgap = dmax - (len1 - 1);
                lx -= pp[1].spc;
        }
        if (dmax0 < len0 - 1) {         /* trailing gap in x */
                lastgap = len0 - dmax0 -1;
                lx -= lastgap;
        }
        else if (dmax0 > len0 - 1) {    /* trailing gap in y */
                lastgap = dmax0 - (len0 - 1);
                ly -= lastgap;
        }
        getmat(lx, ly, firstgap, lastgap);
        pr_align();
}
```

Table 1 (cont')

```
/*
 * trace back the best path, count matches
 */
static
getmat(lx, ly, firstgap, lastgap)                                                    getmat
        int        lx, ly;                    /* "core" (minus endgaps) */
        int        firstgap, lastgap;         /* leading trailing overlap */
{
        int            nm, i0, i1, siz0, siz1;
        char           outx[32];
        double         pct;
        register       n0, n1;
        register char  *p0, *p1;

/* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;

nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }

/* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, " <%d match%s in an overlap of %d: %.2f percent similarity\n",
                nm, (nm == 1)? "" : "es", lx, pct);
```

Table 1 (cont')

```
        fprintf(fx, " <gaps in first sequence: %d", gapx);
```
...getmat
```
        if (gapx) {
                (void) sprintf(outx, " (%d %s%s)",
                        ngapx, (dna)? "base":"residue", (ngapx == 1)? "":"s");
                fprintf(fx,"%s", outx);
        } fprintf(fx, ", gaps in second sequence: %d", gapy);
        if (gapy) {
                (void) sprintf(outx, " (%d %s%s)",
                        ngapy, (dna)? "base":"residue", (ngapy == 1)? "":"s");
                fprintf(fx,"%s", outx);
        }
        if (dna)
                fprintf(fx,
                "\n<score: %d (match = %d, mismatch = %d, gap penalty = %d + %d per base)\n",
                smax, DMAT, DMIS, DINS0, DINS1);
        else
                fprintf(fx,
                "\n<score: %d (Dayhoff PAM 250 matrix, gap penalty = %d + %d per residue)\n",
                smax, PINS0, PINS1);
        if (endgaps)
                fprintf(fx,
                " <endgaps penalized. left endgap: %d %s%s, right endgap: %d %s%s\n",
                firstgap, (dna)? "base" : "residue", (firstgap == 1)? "" : "s",
                lastgap, (dna)? "base" : "residue", (lastgap == 1)? "" : "s");
        else
                fprintf(fx, " <endgaps not penalized\n");
}
static          nm;                /* matches in core -- for checking */
static          lmax;              /* lengths of stripped file names */
static          ij[2];             /* jmp index for a path */
static          nc[2];             /* number at start of current line */
static          ni[2];             /* current elem number -- for gapping */
static          siz[2];
static char     *ps[2];            /* ptr to current element */
static char     *po[2];            /* ptr to next output char slot */
static char     out[2][P_LINE];    /* output line */
static char     star[P_LINE];      /* set by stars() */

/*
 * print alignment of described in struct path pp[ ]
 */
static
pr_align()
```
pr_align
```
{
        int             nn;        /* char count */
        int             more;
        register        i;

for (i = 0, lmax = 0; i < 2; i++) {
                nn = stripname(namex[i]);
                if (nn > lmax)
                        lmax = nn;

nc[i] = 1;
                ni[i] = 1;
                siz[i] = ij[i] = 0;
                ps[i] = seqx[i];
                po[i] = out[i];                                  }
```

Table 1 (cont')

```
            for (nn = nm = 0, more = 1; more; ) {
...pr_align
                for (i = more = 0; i < 2; i++) {
                    /*
                     * do we have more of this sequence?
                     */
                    if (!*ps[i])
                            continue;

more++;

if (pp[i].spc) {       /* leading space */
                            *po[i]++ = ' ';
                            pp[i].spc--;
                    }
                    else if (siz[i]) {     /* in a gap */
                            *po[i]++ = '-';
                            siz[i]--;
                    }
                    else {                 /* we're putting a seq element
                                            */
                            *po[i] = *ps[i];
                            if (islower(*ps[i]))
                                    *ps[i] = toupper(*ps[i]);
                            po[i]++;
                            ps[i]++;

/*
                             * are we at next gap for this seq?
                             */
                            if (ni[i] == pp[i].x[ij[i]]) {
                                    /*
                                     * we need to merge all gaps
                                     * at this location
                                     */
                                    siz[i] = pp[i].n[ij[i]++];
                                    while (ni[i] == pp[i].x[ij[i]])
                                            siz[i] += pp[i].n[ij[i]++];
                            }
                            ni[i]++;
                    }
                }
                if (++nn == olen || !more && nn) {
                    dumpblock();
                    for (i = 0; i < 2; i++)
                            po[i] = out[i];
                    nn = 0;
                }
            }
}
/*
 * dump a block of lines, including numbers, stars: pr_align()
 */
static
dumpblock()
            dumpblock
{
            register i;
            for (i = 0; i < 2; i++)
                    *po[i]-- = '\0';
```

```
                (void) putc('\n', fx);
                for (i = 0; i < 2; i++) {
                        if (*out[i] && (*out[i] != ' ' || *(po[i]) != ' ')) {
                                if (i == 0)
                                        nums(i);
                                if (i == 0 && *out[1])
                                        stars();
                                putline(i);
                                if (i == 0 && *out[1])
                                        fprintf(fx, star);
                                if (i == 1)
                                        nums(i);
                        }
                }
}
/*
 * put out a number line: dumpblock()
 */
static
nums(ix)                                                                                                                    ...dumpblock
        int     ix;     /* index in out[ ] holding seq line */
{
        char            nline[P_LINE];
        register        i, j;
        register char   *pn, *px, *py;

for (pn = nline, i = 0; i < lmax+P_SPC; i++, pn++)
                *pn = ' ';
        for (i = nc[ix], py = out[ix]; *py; py++, pn++) {
                if (*py == ' ' || *py == '-')
                        *pn = ' ';
                else {
                        if (i%10 == 0 || (i == 1 && nc[ix] != 1)) {
                                j = (i < 0)? -i : i;
                                for (px = pn; j; j /= 10, px--)
                                        *px = j%10 + '0';
                                if (i < 0)
                                        *px = '-';
                        }
                        else
                                *pn = ' ';
                        i++;
                }
        }
        *pn = '\0';
        nc[ix] = i;
        for (pn = nline; *pn; pn++)
                (void) putc(*pn, fx);
        (void) putc('\n', fx);
}
/*
 * put out a line (name, [num], seq, [num]): dumpblock()
 */
static
putline(ix)                                                                                                                 putline
        int     ix;                     {
```

Table 1 (cont')

...putline

```
        int             i;
        register char   *px;

for (px = namex[ix], i = 0; *px && *px != ':'; px++, i++)
                (void) putc(*px, fx);
        for (; i < lmax+P_SPC; i++)
                (void) putc(' ', fx);

/* these count from 1:
         * ni[ ] is current element (from 1)
         * nc[ ] is number at start of current line
         */
        for (px = out[ix]; *px; px++)
                (void) putc(*px&0x7F, fx);
        (void) putc('\n', fx);
}

/*
 * put a line of stars (seqs always in out[0], out[1]): dumpblock()
 */
static
stars()
``` stars

```
{
        int             i;
        register char   *p0, *p1, cx, *px;

if (!*out[0] || (*out[0] == ' ' && *(po[0]) == ' ') ||
            !*out[1] || (*out[1] == ' ' && *(po[1]) == ' '))
                return;
        px = star;
        for (i = lmax+P_SPC; i; i--)
                *px++ = ' ';

for (p0 = out[0], p1 = out[1]; *p0 && *p1; p0++, p1++) {
                if (isalpha(*p0) && isalpha(*p1)) { if (xbm[*p0-'A']&xbm[*p1-'A']) {
                                cx = '*';
                                nm++;
                        }
                        else if (!dna && _day[*p0-'A'][*p1-'A'] > 0)
                                cx = '.';
                        else
                                cx = ' ';
                }
                else
                        cx = ' ';
                *px++ = cx;
        }
        *px++ = '\n';
        *px = '\0';
}
```

Table 1 (cont')

```
/*
 * strip path or prefix from pn, return len: pr_align()
 */
static
stripname(pn)
          stripname
          char      *pn;      /* file name (may be path) */
{
          register char     *px, *py;

py = 0;
          for (px = pn; *px; px++)
                    if (*px == '/')
                              py = px + 1;
          if (py)
                    (void) strcpy(pn, py);
          return(strlen(pn));

}
```

Table 1 (cont')

```
/*
 * cleanup() -- cleanup any tmp file
 * getseq() -- read in seq, set dna, len, maxlen
 * g_calloc() -- calloc() with error checkin
 * readjmps() -- get the good jmps, from tmp file if necessary
 * writejmps() -- write a filled array of jmps to a tmp file: nw()
 */
include "nw.h"
include <sys/file.h> char      *jname = "/tmp/homgXXXXXX";       /* tmp file for jmps */
FILE      *fj;

int       cleanup();                         /* cleanup tmp file */
long      lseek();

/*
 * remove any tmp file if we blow
 */
cleanup(i)                                                                            cleanup
          int       i;
{
          if (fj)
                    (void) unlink(jname);
          exit(i);
}

/*
 * read, return ptr to seq, set dna, len, maxlen
 * skip lines starting with ';', '<', or '>'
 * seq in upper or lower case
 */
char      *
getseq(file, len)                                                                     getseq
          char      *file;    /* file name */
          int       *len;     /* seq len */
{
          char      line[1024], *pseq;
          register char   *px, *py;
          int       natgc, tlen;
          FILE      *fp;

if ((fp = fopen(file,"r")) == 0) {
                    fprintf(stderr,"%s: can't read %s\n", prog, file);
                    exit(1);
          }
          tlen = natgc = 0;
          while (fgets(line, 1024, fp)) {
                    if (*line == ';' || *line == '<' || *line == '>')
                              continue;
                    for (px = line; *px != '\n'; px++)
                              if (isupper(*px) || islower(*px))
                                        tlen++;
          }
          if ((pseq = malloc((unsigned)(tlen+6))) == 0) {
                    fprintf(stderr,"%s: malloc() failed to get %d bytes for %s\n", prog, tlen+6, file);
                    exit(1);
          }
          pseq[0] = pseq[1] = pseq[2] = pseq[3] = '\0';
```

Table 1 (cont')

...getseq

```
        py = pseq + 4;
        *len = tlen;
        rewind(fp);

while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
                                natgc++;
                }
        }
        *py++ = '\0';
        *py = '\0';
        (void) fclose(fp);
        dna = natgc > (tlen/3);
        return(pseq+4);
} char    *
g_calloc(msg, nx, sz)
```
g_calloc
```
        char    *msg;           /* program, calling routine */
        int     nx, sz;         /* number and size of elements */
{
        char    *px, *calloc();

if ((px = calloc((unsigned)nx, (unsigned)sz)) == 0) {
                if (*msg) {
                        fprintf(stderr, "%s: g_calloc() failed %s (n=%d, sz=%d)\n", prog, msg, nx, sz);
                        exit(1);
                }
        }
        return(px);
}

/*
* get final jmps from dx[ ] or tmp file, set pp[ ], reset dmax: main()
*/
readjmps()
```
readjmps
```
{
        int             fd = -1;
        int             siz, i0, i1;
        register i, j, xx;

if (fj) {
                (void) fclose(fj);
                if ((fd = open(jname, O_RDONLY, 0)) < 0) {
                        fprintf(stderr, "%s: can't open() %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
```

Table 1 (cont')

...readjmps

```
                    if (j < 0 && dx[dmax].offset && fj) {
                            (void) lseek(fd, dx[dmax].offset, 0);
                            (void) read(fd, (char *)&dx[dmax].jp, sizeof(struct jmp));
                            (void) read(fd, (char *)&dx[dmax].offset, sizeof(dx[dmax].offset));
                            dx[dmax].ijmp = MAXJMP-1;
                    }
                    else
                            break;
            }
            if (i > = JMPS) {
                    fprintf(stderr, "%s: too many gaps in alignment\n", prog);
                    cleanup(1);
            }
            if (j > = 0) {
                    siz = dx[dmax].jp.n[j];
                    xx  = dx[dmax].jp.x[j];
                    dmax += siz;
                    if (siz < 0) {                /* gap in second seq */
                            pp[1].n[i1] = -siz;
                            xx += siz;
                            /* id = xx - yy + len1 - 1
                             */
                            pp[1].x[i1] = xx - dmax + len1 - 1;
                            gapy++;
                            ngapy -= siz;
/* ignore MAXGAP when doing endgaps */
                            siz = (-siz < MAXGAP || endgaps)? -siz : MAXGAP;
                            i1++;
                    }
                    else if (siz > 0) {    /* gap in first seq */
                            pp[0].n[i0] = siz;
                            pp[0].x[i0] = xx;
                            gapx++;
                            ngapx += siz;
/* ignore MAXGAP when doing endgaps */
                            siz = (siz < MAXGAP || endgaps)? siz : MAXGAP;
                            i0++;
                    }
            }
            else
                    break;
    }

/* reverse the order of jmps
     */
    for (j = 0, i0--; j < i0; j++, i0--) {
            i = pp[0].n[j]; pp[0].n[j] = pp[0].n[i0]; pp[0].n[i0] = i;
            i = pp[0].x[j]; pp[0].x[j] = pp[0].x[i0]; pp[0].x[i0] = i;
    }
    for (j = 0, i1--; j < i1; j++, i1--) {
            i = pp[1].n[j]; pp[1].n[j] = pp[1].n[i1]; pp[1].n[i1] = i;
            i = pp[1].x[j]; pp[1].x[j] = pp[1].x[i1]; pp[1].x[i1] = i;
    }
    if (fd > = 0)
            (void) close(fd);
    if (fj) {
            (void) unlink(jname);
            fj = 0;
            offset = 0;
    }
}                                       }
```

Table 1 (cont')

```
/*
 * write a filled jmp struct offset of the prev one (if any): nw()
 */
writejmps(ix)
        writejmps
        int     ix;
{
        char    *mktemp();

if (!fj) {
                if (mktemp(jname) < 0) {
                        fprintf(stderr, "%s: can't mktemp() %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
}
```

TABLE 2

| | | |
|---|---|---|
| PRO87299 | XXXXXXXXXXXXXXX | (Length = 15 amino acids) |
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the PRO87299 polypeptide) =5 divided by 15 = 33.3%

TABLE 3

| | | |
|---|---|---|
| PRO87299 | XXXXXXXXXX | (Length = 10 amino acids) |
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the PRO87299 polypeptide) =5 divided by 10 = 50%

TABLE 4

| | | |
|---|---|---|
| PRO87299-DNA | NNNNNNNNNNNNNN | (Length = 14 nucleotides) |
| Comparison DNA | NNNNNNLLLLLLLLLL | (Length = 16 nucleotides) |

% nucleic acid sequence identity = (the number of identically matching nucleotides between the two nucleic acid sequences as determined by ALIGN-2) divided by (the total number of nucleotides of the PRO87299-DNA nucleic acid sequence) =6 divided by 14 = 42.9%

TABLE 5

| | | |
|---|---|---|
| PRO87299-DNA | NNNNNNNNNNNN | (Length = 12 nucleotides) |
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the PRO87299-DNA nucleic acid sequence) =4 divided by 12 = 33.3%

II. Compositions and Methods of the Invention

A. Full-Length PRO87299 Polypeptides

The present invention provides newly identified and isolated nucleotide sequences encoding polypeptides referred to in the present application as PRO87299 polypeptides. In particular, cDNAs encoding various PRO87299 polypeptides have been identified and isolated, as disclosed in further detail in the Examples below.

The actual nucleotide sequences of those clones can readily be determined by the skilled artisan by sequencing of the deposited clone using routine methods in the art. The predicted amino acid sequence can be determined from the nucleotide sequence using routine skill. For the PRO87299 polypeptides and encoding nucleic acids described herein, Applicants have identified what is believed to be the reading frame best identifiable with the sequence information available at the time.

B. PRO87299 Polypeptide Variants

In addition to the full-length native sequence PRO87299 polypeptides described herein, it is contemplated that PRO87299 variants can be prepared. PRO87299 variants can be prepared by introducing appropriate nucleotide changes into the PRO87299 DNA, and/or by synthesis of the desired PRO87299 polypeptide. Those skilled in the art will appreciate that amino acid changes may alter post-translational processes of the PRO87299, such as changing the number or position of glycosylation sites or altering the membrane anchoring characteristics.

Variations in the native full-length sequence PRO87299 or in various domains of the PRO87299 described herein, can be made, for example, using any of the techniques and guidelines for conservative and non-conservative mutations set forth, for instance, in U.S. Pat. No. 5,364,934. Variations may be a substitution, deletion or insertion of one or more codons encoding the PRO87299 that results in a change in the amino acid sequence of the PRO87299 as compared with the native sequence PRO87299. Optionally, the variation is by substitution of at least one amino acid with any other amino acid in one or more of the domains of the PRO87299. Guidance in determining which amino acid residue may be inserted, substituted or deleted without adversely affecting the desired activity may be found by comparing the sequence of the PRO87299 with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

PRO87299 polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the PRO87299 polypeptide. PRO87299 fragments may be prepared by any of a number of conventional techniques. Desired peptide fragments may be chemically synthesized. An alternative approach involves generating PRO87299 fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, PRO87299 polypeptide fragments share at least one biological and/or immunological activity with the native PRO87299 polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |

TABLE 6-continued

| Original Residue | Exemplary Substitutions | Preferred Substitutions |
| --- | --- | --- |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in function or immunological identity of the PRO87299 polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.,* 13:4331 (1986); Zoller et al., *Nucl. Acids Res.,* 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)] or other known techniques can be performed on the cloned DNA to produce the PRO87299 variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244: 1081-1085 (1989)]. Alanine is also typically preferred because it is the most common amino acid. Further, it is frequently found in both buried and exposed positions [Creighton, *The Proteins,* (W.H. Freeman & Co., N.Y.); Chothia, *J. Mol. Biol.,* 150:1 (1976)]. If alanine substitution does not yield adequate amounts of variant, an isoteric amino acid can be used.

C. Modifications of PRO87299

Covalent modifications of PRO87299 are included within the scope of this invention. One type of covalent modification includes reacting targeted amino acid residues of a PRO87299 polypeptide with an organic derivatizing agent that is capable of reacting with selected side chains or the N- or C-terminal residues of the PRO87299. Derivatization with bifunctional agents is useful, for instance, for crosslinking PRO87299 to a water-insoluble support matrix or surface for use in the method for purifying anti-PRO87299 antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, *Proteins: Structure and Molecular Properties,* W.H. Freeman & Co., San Francisco, pp. 79-86 (1983)], acetylation of the N-terminal amine, and amidation of any C-terminal carboxyl group.

Another type of covalent modification of the PRO87299 polypeptide included within the scope of this invention comprises altering the native glycosylation pattern of the polypeptide. "Altering the native glycosylation pattern" is intended for purposes herein to mean deleting one or more carbohydrate moieties found in native sequence PRO87299 (either by removing the underlying glycosylation site or by deleting the glycosylation by chemical and/or enzymatic means), and/or adding one or more glycosylation sites that are not present in the native sequence PRO87299. In addition, the phrase includes qualitative changes in the glycosylation of the native proteins, involving a change in the nature and proportions of the various carbohydrate moieties present.

Addition of glycosylation sites to the PRO87299 polypeptide may be accomplished by altering the amino acid sequence. The alteration may be made, for example, by the addition of, or substitution by, one or more serine or threonine residues to the native sequence PRO87299 (for O-linked glycosylation sites). The PRO87299 amino acid sequence may optionally be altered through changes at the DNA level, particularly by mutating the DNA encoding the PRO87299 polypeptide at preselected bases such that codons are generated that will translate into the desired amino acids.

Another means of increasing the number of carbohydrate moieties on the PRO87299 polypeptide is by chemical or enzymatic coupling of glycosides to the polypeptide. Such methods are described in the art, e.g., in WO 87/05330 published 11 Sep. 1987, and in Aplin and Wriston, *CRC Crit. Rev. Biochem.,* pp. 259-306 (1981).

Removal of carbohydrate moieties present on the PRO87299 polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.,* 259:52 (1987) and by Edge et al., *Anal.*

*Biochem.*, 118:131 (1981). Enzymatic cleavage of carbohydrate moieties on polypeptides can be achieved by the use of a variety of endo- and exo-glycosidases as described by Thotakura et al., *Meth. Enzymol.*, 138:350 (1987).

Another type of covalent modification of PRO87299 comprises linking the PRO87299 polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The PRO87299 of the present invention may also be modified in a way to form a chimeric molecule comprising PRO87299 fused to another, heterologous polypeptide or amino acid sequence.

In one embodiment, such a chimeric molecule comprises a fusion of the PRO87299 with a tag polypeptide which provides an epitope to which an anti-tag antibody can selectively bind. The epitope tag is generally placed at the amino- or carboxyl-terminus of the PRO87299. The presence of such epitope-tagged forms of the PRO87299 can be detected using an antibody against the tag polypeptide. Also, provision of the epitope tag enables the PRO87299 to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an alpha-tubulin epitope peptide [Skinner et al., *J. Biol. Chem.*, 266: 15163-15166 (1991)]; and the T7 gene 10 protein peptide tag [Lutz-Freyermuth et al., *Proc. Natl. Acad. Sci. USA*, 87:6393-6397 (1990)].

In an alternative embodiment, the chimeric molecule may comprise a fusion of the PRO87299 with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of a PRO87299 polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

D. Preparation of PRO87299

The description below relates primarily to production of PRO87299 by culturing cells transformed or transfected with a vector containing PRO87299 nucleic acid. It is, of course, contemplated that alternative methods, which are well known in the art, may be employed to prepare PRO87299. For instance, the PRO87299 sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the PRO87299 may be chemically synthesized separately and combined using chemical or enzymatic methods to produce the full-length PRO87299.

1. Isolation of DNA Encoding PRO87299

DNA encoding PRO87299 may be obtained from a cDNA library prepared from tissue believed to possess the PRO87299 mRNA and to express it at a detectable level. Accordingly, human PRO87299 DNA can be conveniently obtained from a cDNA library prepared from human tissue, such as described in the Examples. The PRO87299-encoding gene may also be obtained from a genomic library or by known synthetic procedures (e.g., automated nucleic acid synthesis).

Libraries can be screened with probes (such as antibodies to the PRO87299 or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding PRO87299 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for PRO87299 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, CaCl$_2$, CaPO$_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene*, 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. These examples are illustrative rather than limiting. Strain W3110 is one particularly preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for PRO87299-encoding vectors. *Saccharomyces cerevisiae* is a commonly used lower eukaryotic host microorganism. Others include *Schizosaccharomyces pombe* (Beach and Nurse, *Nature*, 290: 140 [1981]; EP 139,383 published 2 May 1985); *Kluyveromyces* hosts (U.S. Pat. No. 4,943,529; Fleer et al., *Bio/Technology*, 9:968-975 (1991)) such as, e.g., *K. lactis* (MW98-8C, CBS683, CBS4574; Louvencourt et al., *J. Bacteriol.*, 154(2):737-742 [1983], *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 (1990)), *K. thermotolerans*, and *K. marxianus; yarrowia* (EP 402,226); *Pichia pastoris* (EP 183,070; Sreekrishna et al., *J. Basic Microbiol.*, 28:265-278 [1988]); *Candida; Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora*, *Penicillium*, *Tolypocladium* (WO 91/00357 published 10 Jan. 1991), and *Aspergillus* hosts such as *A. nidulans* (Ballance et al., *Biochem. Biophys. Res. Commun.*, 112: 284-289 [1983]; Tilburn et al., *Gene*, 26:205-221 [1983]; Yelton et al., *Proc. Natl. Acad. Sci. USA*, 81: 1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula*, *Candida*, *Kloeckera*, *Pichia*, *Saccharomyces*, *Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated PRO87299 are derived from multicellular organisms. Examples of invertebrate cells include insect cells such as *Drosophila* S2 and *Spodoptera* Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding PRO87299 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The PRO87299 may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the PRO87299-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010,182), or acid phosphatase leader, the C. albicans glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the PRO87299-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the PRO87299-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,776], and hybrid promoters such as the tac promoter [deBoer et al., *Proc. Natl. Acad. Sci. USA,* 80:21-25 (1983)]. Promoters for use in bacterial systems also will contain a Shine-Dalgarno (S.D.) sequence operably linked to the DNA encoding PRO87299.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

PRO87299 transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the PRO87299 by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the PRO87299 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding PRO87299.

Still other methods, vectors, and host cells suitable for adaptation to the synthesis of PRO87299 in recombinant vertebrate cell culture are described in Gething et al., *Nature,* 293:620-625 (1981); Mantei et al., *Nature,* 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201-5205 (1980)], dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence PRO87299 polypeptide or against a synthetic peptide based on the DNA sequences provided herein or against exogenous sequence fused to PRO87299 DNA and encoding a specific antibody epitope.

5. Purification of Polypeptide

Forms of PRO87299 may be recovered from culture medium or from host cell lysates. If membrane-bound, it can be released from the membrane using a suitable detergent solution (e.g. Triton-X 100) or by enzymatic cleavage. Cells employed in expression of PRO87299 can be disrupted by various physical or chemical means, such as freeze-thaw cycling, sonication, mechanical disruption, or cell lysing agents.

It may be desired to purify PRO87299 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the PRO87299. Various methods of protein purification may be employed and such methods are known in the art and described for example in Deutscher, *Methods in Enzymology,* 182 (1990); Scopes, *Protein Purification: Principles and Practice,* Springer-Verlag, New York (1982). The purification step(s) selected will depend, for example, on the nature of the production process used and the particular PRO87299 produced.

E. Tissue Distribution

The location of tissues expressing the PRO87299 can be identified by determining mRNA expression in various human tissues. The location of such genes provides information about which tissues are most likely to be affected by the stimulating and inhibiting activities of the PRO87299 polypeptides. The location of a gene in a specific tissue also provides sample tissue for the activity blocking assays discussed below.

As noted before, gene expression in various tissues may be measured by conventional Southern blotting, Northern blotting to quantitate the transcription of mRNA (Thomas, *Proc. Natl. Acad. Sci. USA,* 77:5201-5205 [1980]), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence of a PRO87299 polypeptide or against a synthetic peptide based on the DNA sequences encoding the PRO87299 polypeptide or against an exogenous sequence fused to a DNA encoding a PRO87299 polypeptide and encoding a specific antibody epitope. General techniques for generating antibodies, and special protocols for Northern blotting and in situ hybridization are provided below.

F. Antibody Binding Studies

The activity of the PRO87299 polypeptides can be further verified by antibody binding studies, in which the ability of anti-PRO87299 antibodies to inhibit the effect of the PRO87299 polypeptides, respectively, on tissue cells is tested. Exemplary antibodies include polyclonal, monoclonal, humanized, bispecific, and heteroconjugate antibodies, the preparation of which will be described hereinbelow.

Antibody binding studies may be carried out in any known assay method, such as competitive binding assays, direct and indirect sandwich assays, and immunoprecipitation assays. Zola, *Monoclonal Antibodies: A Manual of Techniques,* pp. 147-158 (CRC Press, Inc., 1987).

Competitive binding assays rely on the ability of a labeled standard to compete with the test sample analyte for binding with a limited amount of antibody. The amount of target protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tissue sample may be fresh or frozen or may be embedded in paraffin and fixed with a preservative such as formalin, for example.

G. Cell-Based Assays

Cell-based assays and animal models for immune related diseases can be used to further understand the relationship between the genes and polypeptides identified herein and the development and pathogenesis of immune related disease.

In a different approach, cells of a cell type known to be involved in a particular immune related disease are transfected with the cDNAs described herein, and the ability of these cDNAs to stimulate or inhibit immune function is analyzed. Suitable cells can be transfected with the desired gene, and monitored for immune function activity. Such transfected cell lines can then be used to test the ability of poly- or monoclonal antibodies or antibody compositions to inhibit or stimulate immune function, for example to modulate T-cell proliferation or inflammatory cell infiltration. Cells transfected with the coding sequences of the genes identified herein can further be used to identify drug candidates for the treatment of immune related diseases.

In addition, primary cultures derived from transgenic animals (as described below) can be used in the cell-based assays herein, although stable cell lines are preferred. Techniques to derive continuous cell lines from transgenic animals are well known in the art (see, e.g., Small et al., *Mol. Cell. Biol.* 5: 642-648 [1985]).

One suitable cell based assay is the mixed lymphocyte reaction (MLR). *Current Protocols in Immunology*, unit 3.12; edited by J E Coligan, A M Kruisbeek, D H Marglies, E M Shevach, W Strober, National Institutes of Health, Published by John Wiley & Sons, Inc. In this assay, the ability of a test compound to stimulate or inhibit the proliferation of activated T cells is assayed. A suspension of responder T cells is cultured with allogeneic stimulator cells and the proliferation of T cells is measured by uptake of tritiated thymidine. This assay is a general measure of T cell reactivity. Since the majority of T cells respond to and produce IL-2 upon activation, differences in responsiveness in this assay in part reflect differences in IL-2 production by the responding cells. The MLR results can be verified by a standard lymphokine (IL-2) detection assay. *Current Protocols in Immunology, above*, 3.15, 6.3.

A proliferative T cell response in an MLR assay may be due to direct mitogenic properties of an assayed molecule or to external antigen induced activation. T cell activation requires an antigen specific signal mediated through the T-cell receptor (TCR) and a costimulatory signal mediated through a second ligand binding interaction, for example, the B7 (CD80, CD86)/CD28 binding interaction. CD28 crosslinking increases lymphokine secretion by activated T cells. T cell activation has both negative and positive controls through the binding of ligands which have a negative or positive effect. CD28 and CTLA-4 are related glycoproteins in the Ig superfamily which bind to B7. CD28 binding to B7 has a positive costimulation effect of T cell activation; conversely, CTLA-4 binding to B7 has a T cell deactivating effect. Chambers, C. A. and Allison, J. P., *Curr. Opin. Immunol.* (1997) 9:396. Schwartz, R. H., *Cell* (1992) 71:1065; Linsey, P. S, and Ledbetter, J. A., *Annu. Rev. Immunol.* (1993) 11:191; June, C. H. et al, *Immunol. Today* (1994) 15:321; Jenkins, M. K., *Immunity* (1994) 1:405. In a costimulation assay, the PRO87299 polypeptides are assayed for T cell costimulatory or inhibitory activity.

Direct use of a stimulating compound as in the invention has been validated in experiments with 4-1BB glycoprotein, a member of the tumor necrosis factor receptor family, which binds to a ligand (4-1BBL) expressed on primed T cells and signals T cell activation and growth. Alderson, M. E. et al., *J. Immunol.* (1994) 24:2219.

The use of an agonist stimulating compound has also been validated experimentally. Activation of 4-1BB by treatment with an agonist anti-4-1BB antibody enhances eradication of tumors. Hellstrom, I. and Hellstrom, K. E., *Crit. Rev. Immunol.* (1998) 18:1. Immunoadjuvant therapy for treatment of tumors, described in more detail below, is another example of the use of the stimulating compounds of the invention.

Alternatively, an immune stimulating or enhancing effect can also be achieved by administration of a PRO87299 which has vascular permeability enhancing properties. Enhanced vascular permeability would be beneficial to disorders which can be attenuated by local infiltration of immune cells (e.g., monocytes, eosinophils, PMNs) and inflammation.

On the other hand, PRO87299 polypeptides, as well as other compounds of the invention, which are direct inhibitors of T cell proliferation/activation, lymphokine secretion, and/or vascular permeability can be directly used to suppress the immune response. These compounds are useful to reduce the degree of the immune response and to treat immune related diseases characterized by a hyperactive, superoptimal, or autoimmune response. This use of the compounds of the invention has been validated by the experiments described above in which CTLA-4 binding to receptor B7 deactivates T cells. The direct inhibitory compounds of the invention function in an analogous manner. The use of compound which suppress vascular permeability would be expected to reduce inflammation. Such uses would be beneficial in treating conditions associated with excessive inflammation.

Alternatively, compounds, e.g., antibodies, which bind to stimulating PRO87299 polypeptides and block the stimulating effect of these molecules produce a net inhibitory effect and can be used to suppress the T cell mediated immune response by inhibiting T cell proliferation/activation and/or lymphokine secretion. Blocking the stimulating effect of the polypeptides suppresses the immune response of the mammal. This use has been validated in experiments using an anti-IL2 antibody. In these experiments, the antibody binds to IL2 and blocks binding of IL2 to its receptor thereby achieving a T cell inhibitory effect.

H. Animal Models

The results of the cell based in vitro assays can be further verified using in vivo animal models and assays for T-cell function. A variety of well known animal models can be used to further understand the role of the genes identified herein in the development and pathogenesis of immune related disease, and to test the efficacy of candidate therapeutic agents, including antibodies, and other antagonists of the native polypeptides, including small molecule antagonists. The in vivo nature of such models makes them predictive of responses in human patients. Animal models of immune related diseases include both non-recombinant and recombinant (transgenic) animals. Non-recombinant animal models include, for example, rodent, e.g., murine models. Such models can be generated by introducing cells into syngeneic mice using standard techniques, e.g., subcutaneous injection, tail vein injection, spleen implantation, intraperitoneal implantation, implantation under the renal capsule, etc.

Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T cell reactivity against MHC antigens and minor transplant antigens. A suitable procedure is described in detail in Current Protocols in Immunology, above, unit 4.3.

An animal model for skin allograft rejection is a means of testing the ability of T cells to mediate in vivo tissue destruction and a measure of their role in transplant rejection. The most common and accepted models use murine tail-skin grafts. Repeated experiments have shown that skin allograft rejection is mediated by T cells, helper T cells and killer-effector T cells, and not antibodies. Auchincloss, H. Jr. and Sachs, D. H., *Fundamental Immunology*, 2nd ed., W. E. Paul ed., Raven Press, NY, 1989, 889-992. A suitable procedure is described in detail in *Current Protocols in Immunology*, above, unit 4.4. Other transplant rejection models which can be used to test the compounds of the invention are the allogeneic heart transplant models described by Tanabe, M. et al, *Transplantation* (1994) 58:23 and Tinubu, S. A. et al, *J. Immunol.* (1994) 4330-4338.

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in *Current Protocols in Immunology*, above, unit 4.5.

EAE is a T cell mediated autoimmune disease characterized by T cell and mononuclear cell inflammation and subsequent demyelination of axons in the central nervous system. EAE is generally considered to be a relevant animal model for MS in humans. Bolton, C., *Multiple Sclerosis* (1995) 1:143. Both acute and relapsing-remitting models have been developed. The compounds of the invention can be tested for T cell stimulatory or inhibitory activity against immune mediated demyelinating disease using the protocol described in *Current Protocols in Immunology*, above, units 15.1 and 15.2. See also the models for myelin disease in which oligodendrocytes or Schwann cells are grafted into the central nervous system as described in Duncan, I. D. et al, *Molec. Med. Today* (1997) 554-561.

Contact hypersensitivity is a simple delayed type hypersensitivity in vivo assay of cell mediated immune function. In this procedure, cutaneous exposure to exogenous haptens which gives rise to a delayed type hypersensitivity reaction which is measured and quantitated. Contact sensitivity involves an initial sensitizing phase followed by an elicitation phase. The elicitation phase occurs when the T lymphocytes encounter an antigen to which they have had previous contact. Swelling and inflammation occur, making this an excellent model of human allergic contact dermatitis. A suitable procedure is described in detail in *Current Protocols in Immunology*, Eds. J. E. Cologan, A. M. Kruisbeek, D. H. Margulies, E. M. Shevach and W. Strober, John Wiley & Sons, Inc., 1994, unit 4.2. See also Grabbe, S, and Schwarz, T, *Immun. Today* 19 (1): 37-44 (1998).

An animal model for arthritis is collagen-induced arthritis. This model shares clinical, histological and immunological characteristics of human autoimmune rheumatoid arthritis and is an acceptable model for human autoimmune arthritis. Mouse and rat models are characterized by synovitis, erosion of cartilage and subchondral bone. The compounds of the invention can be tested for activity against autoimmune arthritis using the protocols described in *Current Protocols in Immunology*, above, units 15.5. See also the model using a monoclonal antibody to CD18 and VLA-4 integrins described in Issekutz, A. C. et al., *Immunology* (1996) 88:569.

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test the compounds of the invention for activity and effectiveness in the treatment of asthma are described by Wolyniec, W. W. et al, *Am. J. Respir. Cell Mol. Biol.* (1998) 18:777 and the references cited therein.

Additionally, the compounds of the invention can be tested on animal models for psoriasis like diseases. Evidence suggests a T cell pathogenesis for psoriasis. The compounds of the invention can be tested in the scid/scid mouse model described by Schon, M. P. et al, *Nat. Med.* (1997) 3:183, in which the mice demonstrate histopathologic skin lesions resembling psoriasis. Another suitable model is the human skin/scid mouse chimera prepared as described by Nickoloff, B. J. et al, *Am. J. Path*. (1995) 146:580.

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g., baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA* 82, 6148-615 [1985]); gene targeting in embryonic stem cells (Thompson et al., *Cell* 56, 313-321 [1989]); electroporation of embryos (Lo, *Mol. Cel. Biol.* 3, 1803-1814 [1983]); sperm-mediated gene transfer (Lavitrano et al., *Cell* 57, 717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA* 89, 6232-636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry.

The animals may be further examined for signs of immune disease pathology, for example by histological examination to determine infiltration of immune cells into specific tissues. Blocking experiments can also be performed in which the transgenic animals are treated with the compounds of the invention to determine the extent of the T cell proliferation stimulation or inhibition of the compounds. In these experiments, blocking antibodies which bind to the PRO87299 polypeptide, prepared as described above, are administered to the animal and the effect on immune function is determined.

Alternatively, "knock out" animals can be constructed which have a defective or altered gene encoding a polypeptide identified herein, as a result of homologous recombination between the endogenous gene encoding the polypeptide and altered genomic DNA encoding the same polypeptide introduced into an embryonic cell of the animal. For example, cDNA encoding a particular polypeptide can be used to clone genomic DNA encoding that polypeptide in accordance with established techniques. A portion of the genomic DNA encoding a particular polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell*, 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the polypeptide.

I. ImmunoAdjuvant Therapy

In one embodiment, the immunostimulating compounds of the invention can be used in immunoadjuvant therapy for the treatment of tumors (cancer). It is now well established that T cells recognize human tumor specific antigens. One group of tumor antigens, encoded by the MAGE, BAGE and GAGE families of genes, are silent in all adult normal tissues, but are expressed in significant amounts in tumors, such as melanomas, lung tumors, head and neck tumors, and bladder carcinomas. DeSmet, C. et al., (1996) *Proc. Natl. Acad. Sci. USA*, 93:7149. It has been shown that costimulation of T cells induces tumor regression and an antitumor response both in vitro and in vivo. Melero, I. et al., *Nature Medicine* (1997) 3:682; Kwon, E. D. et al., *Proc. Natl. Acad. Sci. USA* (1997) 94: 8099; Lynch, D. H. et al, *Nature Medicine* (1997) 3:625; Finn, O. J. and Lotze, M. T., *J. Immunol.* (1998) 21:114. The stimulatory compounds of the invention can be administered as adjuvants, alone or together with a growth regulating agent, cytotoxic agent or chemotherapeutic agent, to stimulate T cell proliferation/activation and an antitumor response to tumor antigens. The growth regulating, cytotoxic, or chemotherapeutic agent may be administered in conventional amounts using known administration regimes. Immunostimulating activity by the compounds of the invention allows reduced amounts of the growth regulating, cytotoxic, or chemotherapeutic agents thereby potentially lowering the toxicity to the patient.

J. Screening Assays for Drug Candidates

Screening assays for drug candidates are designed to identify compounds that bind to or complex with the polypeptides encoded by the genes identified herein or a biologically active fragment thereof, or otherwise interfere with the interaction of the encoded polypeptides with other cellular proteins. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art. All assays are common in that they call for contacting the drug candidate with a polypeptide encoded by a nucleic acid identified herein under conditions and for a time sufficient to allow these two components to interact.

In binding assays, the interaction is binding and the complex formed can be isolated or detected in the reaction mixture. In a particular embodiment, the polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the polypeptide and drying. Alternatively, an immobilized antibody, e.g., a monoclonal antibody, specific for the polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labelled antibody specifically binding the immobilized complex.

If the candidate compound interacts with but does not bind to a particular protein encoded by a gene identified herein, its interaction with that protein can be assayed by methods well known for detecting protein-protein interactions. Such assays include traditional approaches, such as, cross-linking, co-immunoprecipitation, and co-purification through gradients or chromatographic columns. In addition, protein-protein interactions can be monitored by using a yeast-based genetic system described by Fields and co-workers [Fields and Song, *Nature* (London) 340, 245-246 (1989); Chien et al., *Proc. Natl. Acad. Sci. USA* 88, 9578-9582 (1991)] as disclosed by Chevray and Nathans, *Proc. Natl. Acad. Sci. USA* 89, 5789-5793 (1991). Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

In order to find compounds that interfere with the interaction of a gene identified herein and other intra- or extracellular components can be tested, a reaction mixture is usually prepared containing the product of the gene and the intra- or extracellular component under conditions and for a time allowing for the interaction and binding of the two products. To test the ability of a test compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described above. The formation of a complex in the control reaction(s) but not in the reaction mixture containing the test compound indicates that the test compound interferes with the interaction of the test compound and its reaction partner.

K. Compositions and Methods for the Treatment of Immune Related Diseases

The compositions useful in the treatment of immune related diseases include, without limitation, proteins, antibodies, small organic molecules, peptides, phosphopeptides, antisense and ribozyme molecules, triple helix molecules, etc. that inhibit or stimulate immune function, for example, T cell proliferation/activation, lymphokine release, or immune cell infiltration.

For example, antisense RNA and RNA molecules act to directly block the translation of mRNA by hybridizing to targeted mRNA and preventing protein translation. When antisense DNA is used, oligodeoxyribonucleotides derived from the translation initiation site, e.g., between about −10 and +10 positions of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology* 4, 469-471 (1994), and PCT publication No. WO 97/33551 (published Sep. 18, 1997).

Nucleic acid molecules in triple helix formation used to inhibit transcription should be single-stranded and composed of deoxynucleotides. The base composition of these oligonucleotides is designed such that it promotes triple helix formation via Hoogsteen base pairing rules, which generally require sizeable stretches of purines or pyrimidines on one strand of a duplex. For further details see, e.g., PCT publication No. WO 97/33551, supra.

These molecules can be identified by any or any combination of the screening assays discussed above and/or by any other screening techniques well known for those skilled in the art.

L. Anti-PRO87299 Antibodies

The present invention further provides anti-PRO87299 antibodies. Exemplary antibodies include polyclonal, monoclonal, humanized, bispecific, and heteroconjugate antibodies.

1. Polyclonal Antibodies

The anti-PRO87299 antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the PRO87299 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

2. Monoclonal Antibodies

The anti-PRO87299 antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the PRO87299 polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59-103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications*, Marcel Dekker, Inc., New York, (1987) pp. 51-63].

The culture medium in which the hybridoma cells are cultured can then be assayed for the presence of monoclonal antibodies directed against PRO87299. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

3. Human and Humanized Antibodies

The anti-PRO87299 antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., Nature, 321:522-525 (1986); Riechmann et al., Nature, 332:323-327 (1988); Verhoeyen et al., Science, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, J. Mol. Biol., 227:381 (1991); Marks et al., J. Mol. Biol., 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368, 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

The antibodies may also be affinity matured using known selection and/or mutagenesis methods as described above. Preferred affinity matured antibodies have an affinity which is five times, more preferably 10 times, even more preferably 20 or 30 times greater than the starting antibody (generally murine, humanized or human) from which the matured antibody is prepared.

4. Bispecific Antibodies

Bispecific antibodies are monoclonal, preferably human or humanized, antibodies that have binding specificities for at least two different antigens. In the present case, one of the binding specificities is for the PRO87299, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, Nature, 305:537-539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., *EMBO J.,* 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology,* 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')$_2$ bispecific antibodies). Techniques for generating bispecific antibodies from antibody fragments have been described in the literature. For example, bispecific antibodies can be prepared can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175:217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various technique for making and isolating bispecific antibody fragments directly from recombinant cell culture have also been described. For example, bispecific antibodies have been produced using leucine zippers. Kostelny et al., *J. Immunol.* 148(5): 1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., *J. Immunol.* 152:5368 (1994).

Antibodies with more than two valencies are contemplated. For example, trispecific antibodies can be prepared. Tutt et al., *J. Immunol.* 147:60 (1991).

Exemplary bispecific antibodies may bind to two different epitopes on a given PRO87299 polypeptide herein. Alternatively, an anti-PRO87299 polypeptide arm may be combined with an arm which binds to a triggering molecule on a leukocyte such as a T-cell receptor molecule (e.g. CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular PRO87299 polypeptide. Bispecific antibodies may also be used to localize cytotoxic agents to cells which express a particular PRO87299 polypeptide. These antibodies possess a PRO87299-binding arm and an arm which binds a cytotoxic agent or a radionuclide chelator, such as EOTUBE, DPTA, DOTA, or TETA. Another bispecific antibody of interest binds the PRO87299 polypeptide and further binds tissue factor (TF).

5. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

6. Effector Function Engineering

It may be desirable to modify the antibody of the invention with respect to effector function, so as to enhance, e.g., the effectiveness of the antibody in treating cancer. For example, cysteine residue(s) may be introduced into the Fc region, thereby allowing interchain disulfide bond formation in this region. The homodimeric antibody thus generated may have improved internalization capability and/or increased complement-mediated cell killing and antibody-dependent cellular cytotoxicity (ADCC). Caron et al., *J. Exp Med.,* 176: 1191-1195 (1992) and Shopes, *J. Immunol.,* 148: 2918-2922

(1992). Homodimeric antibodies with enhanced anti-tumor activity may also be prepared using heterobifunctional cross-linkers as described in Wolff et al. *Cancer Research*, 53: 2560-2565 (1993). Alternatively, an antibody can be engineered that has dual Fc regions and may thereby have enhanced complement lysis and ADCC capabilities. See Stevenson et al., *Anti-Cancer Drug Design*, 3: 219-230 (1989).

7. Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science*, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

8. Immunoliposomes

The antibodies disclosed herein may also be formulated as immunoliposomes. Liposomes containing the antibody are prepared by methods known in the art, such as described in Epstein et al., *Proc. Natl. Acad. Sci. USA*, 82: 3688 (1985); Hwang et al., *Proc. Natl. Acad. Sci. USA*, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.*, 257: 286-288 (1982) via a disulfide-interchange reaction. A chemotherapeutic agent (such as Doxorubicin) is optionally contained within the liposome. See Gabizon et al., *J. National Cancer Inst.*, 81(19): 1484 (1989).

M. Pharmaceutical Compositions

The active PRO87299 molecules of the invention (e.g., PRO87299 polypeptides, anti-PRO87299 antibodies, and/or variants of each) as well as other molecules identified by the screening assays disclosed above, can be administered for the treatment of immune related diseases, in the form of pharmaceutical compositions.

Therapeutic formulations of the active PRO87299 molecule, preferably a polypeptide or antibody of the invention, are prepared for storage by mixing the active molecule having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Compounds identified by the screening assays disclosed herein can be formulated in an analogous manner, using standard techniques well known in the art.

Lipofections or liposomes can also be used to deliver the PRO87299 molecule into cells. Where antibody fragments are used, the smallest inhibitory fragment which specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g., Marasco et al., *Proc. Natl. Acad. Sci. USA* 90, 7889-7893 [1993]).

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active PRO87299 molecules may also be entrapped in microcapsules prepared, for example, by coacervation techniques or by interfacial polymerization, for example, hydroxymethylcellulose or gelatin-microcapsules and poly- (methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations or the PRO87299 molecules may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

N. Methods of Treatment

It is contemplated that the polypeptides, antibodies and other active compounds of the present invention may be used to treat various immune related diseases and conditions, such as T cell mediated diseases, including those characterized by infiltration of inflammatory cells into a tissue, stimulation of T-cell proliferation, inhibition of T-cell proliferation, increased or decreased vascular permeability or the inhibition thereof.

Exemplary conditions or disorders to be treated with the polypeptides, antibodies and other compounds of the invention, include, but are not limited to systemic lupus erythematosis, rheumatoid arthritis, juvenile chronic arthritis, osteoarthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease.

In systemic lupus erythematosus, the central mediator of disease is the production of auto-reactive antibodies to self proteins/tissues and the subsequent generation of immune-mediated inflammation. Antibodies either directly or indirectly mediate tissue injury. Though T lymphocytes have not been shown to be directly involved in tissue damage, T lymphocytes are required for the development of auto-reactive antibodies. The genesis of the disease is thus T lymphocyte dependent. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid if infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stage have necrotic centers surrounded by a mixed inflammatory cell infiltrate. Other manifestations which can occur in RA include: pericarditis, pleuritis, coronary arteritis, intestitial pneumonitis with pulmonary fibrosis, keratoconjunctivitis sicca, and rhematoid nodules.

Juvenile chronic arthritis is a chronic idiopathic inflammatory disease which begins often at less than 16 years of age. Its phenotype has some similarities to RA; some patients which are rhematoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing sponylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of antinuclear antibodies in many patients. ICAM-1 is often upregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjögren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including bilary cirrhosis, peripheral or sensory neuropathy, and palpable purpura.

Systemic vasculitis are diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet β cells; this destruction is mediated by auto-antibodies and auto-reactive T cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including Multiple Sclerosis; idiopathic demyelinating polyneuropathy or Guillain-Barré syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple Sclerosis is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+ T lymphocytes are the predominant cell type at lesions. The mechanism of oligodendrocyte cell death and subsequent demyelination is not known but is likely T lymphocyte driven.

Inflammatory and Fibrotic Lung Disease, including Eosinophilic Pneumonias; Idiopathic Pulmonary Fibrosis, and Hypersensitivity Pneumonitis may involve a disregulated immune-inflammatory response. Inhibition of that response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils.

Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Transplantation associated diseases, including Graft rejection and Graft-Versus-Host-Disease (GVHD) are T lymphocyte-dependent; inhibition of T lymphocyte function is ameliorative. Other diseases in which intervention of the immune and/or inflammatory response have benefit are infectious disease including but not limited to viral infection (including but not limited to AIDS, hepatitis A, B, C, D, E and herpes) bacterial infection, fungal infections, and protozoal and parasitic infections (molecules (or derivatives/agonists) which stimulate the MLR can be utilized therapeutically to enhance the immune response to infectious agents), diseases of immunodeficiency (molecules/derivatives/agonists) which stimulate the MLR can be utilized therapeutically to enhance the immune response for conditions of inherited, acquired, infectious induced (as in HIV infection), or iatrogenic (i.e., as from chemotherapy) immunodeficiency, and neoplasia.

It has been demonstrated that some human cancer patients develop an antibody and/or T lymphocyte response to antigens on neoplastic cells. It has also been shown in animal models of neoplasia that enhancement of the immune response can result in rejection or regression of that particular neoplasm. Molecules that enhance the T lymphocyte response in the MLR have utility in vivo in enhancing the immune response against neoplasia. Molecules which enhance the T lymphocyte proliferative response in the MLR (or small molecule agonists or antibodies that affected the same receptor in an agonistic fashion) can be used therapeutically to treat cancer. Molecules that inhibit the lymphocyte response in the MLR also function in vivo during neoplasia to suppress the immune response to a neoplasm; such molecules can either be expressed by the neoplastic cells themselves or their expression can be induced by the neoplasm in other cells. Antagonism of such inhibitory molecules (either with antibody, small molecule antagonists or other means) enhances immune-mediated tumor rejection.

Additionally, inhibition of molecules with proinflammatory properties may have therapeutic benefit in reperfusion injury; stroke; myocardial infarction; atherosclerosis; acute lung injury; hemorrhagic shock; burn; sepsis/septic shock; acute tubular necrosis; endometriosis; degenerative joint disease and pancreatis.

The compounds of the present invention, e.g., polypeptides or antibodies, are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation (intranasal, intrapulmonary) routes. Intravenous or inhaled administration of polypeptides and antibodies is preferred.

In immunoadjuvant therapy, other therapeutic regimens, such administration of an anti-cancer agent, may be combined with the administration of the proteins, antibodies or compounds of the instant invention. For example, the patient to be treated with a the immunoadjuvant of the invention may also receive an anti-cancer agent (chemotherapeutic agent) or radiation therapy. Preparation and dosing schedules for such chemotherapeutic agents may be used according to manufacturers' instructions or as determined empirically by the skilled practitioner. Preparation and dosing schedules for such chemotherapy are also described in *Chemotherapy Service* Ed., M. C. Perry, Williams & Wilkins, Baltimore, Md. (1992). The chemotherapeutic agent may precede, or follow administration of the immunoadjuvant or may be given simultaneously therewith. Additionally, an anti-estrogen compound such as tamoxifen or an anti-progesterone such as onapristone (see, EP 616812) may be given in dosages known for such molecules.

It may be desirable to also administer antibodies against other immune disease associated or tumor associated antigens, such as antibodies which bind to CD20, CD11a, CD18, ErbB2, EGFR, ErbB3, ErbB4, or vascular endothelial factor (VEGF). Alternatively, or in addition, two or more antibodies binding the same or two or more different antigens disclosed herein may be coadministered to the patient.

Sometimes, it may be beneficial to also administer one or more cytokines to the patient. In one embodiment, the PRO87299 polypeptides are coadministered with a growth inhibitory agent. For example, the growth inhibitory agent may be administered first, followed by a PRO87299 polypeptide. However, simultaneous administration or administration first is also contemplated. Suitable dosages for the growth inhibitory agent are those presently used and may be lowered due to the combined action (synergy) of the growth inhibitory agent and the PRO87299 polypeptide.

For the treatment or reduction in the severity of immune related disease, the appropriate dosage of an a compound of the invention will depend on the type of disease to be treated, as defined above, the severity and course of the disease, whether the agent is administered for preventive or therapeutic purposes, previous therapy, the patient's clinical history and response to the compound, and the discretion of the attending physician. The compound is suitably administered to the patient at one time or over a series of treatments.

For example, depending on the type and severity of the disease, about 1 μg/kg to 15 mg/kg (e.g., 0.1-20 mg/kg) of polypeptide or antibody is an initial candidate dosage for administration to the patient, whether, for example, by one or more separate administrations, or by continuous infusion. A typical daily dosage might range from about 1 μg/kg to 100 mg/kg or more, depending on the factors mentioned above.

For repeated administrations over several days or longer, depending on the condition, the treatment is sustained until a desired suppression of disease symptoms occurs. However, other dosage regimens may be useful. The progress of this therapy is easily monitored by conventional techniques and assays.

O. Articles of Manufacture

In another embodiment of the invention, an article of manufacture containing materials (e.g., comprising a PRO87299 molecule) useful for the diagnosis or treatment of the disorders described above is provided. The article of manufacture comprises a container and an instruction. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is usually a polypeptide or an antibody of the invention. An instruction or label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

P. Diagnosis and Prognosis of Immune Related Disease

Cell surface proteins, such as proteins which are overexpressed in certain immune related diseases, are excellent targets for drug candidates or disease treatment. The same proteins along with secreted proteins encoded by the genes amplified in immune related disease states find additional use in the diagnosis and prognosis of these diseases. For example, antibodies directed against the protein products of genes amplified in multiple sclerosis, rheumatoid arthritis, or another immune related disease, can be used as diagnostics or prognostics.

For example, antibodies, including antibody fragments, can be used to qualitatively or quantitatively detect the expression of proteins encoded by amplified or overexpressed genes ("marker gene products"). The antibody preferably is equipped with a detectable, e.g., fluorescent label, and binding can be monitored by light microscopy, flow cytometry, fluorimetry, or other techniques known in the art. These techniques are particularly suitable, if the overexpressed gene encodes a cell surface protein Such binding assays are performed essentially as described above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Cloning of PRO87299

An expressed sequence tag (EST) DNA database (Merck/Washington University) was searched and an EST was identified which contained domains of interest, specifically Immunoglobulin (Ig) domain(s) and Immuno Tyrosine Inhibition Motif(s) (ITIM). The search was performed using the computer program BLAST or BLAST2 [Altschul et al., *Methods in Enzymology,* 266:460-480 (1996)] using as a comparison the domains of interest to a 6 frame translation of the sequences. Those comparisons resulting in a BLAST score of 70 (or in some cases, 90) or greater that did not encode known proteins were clustered and if necessary, assembled into consensus DNA sequences with the program "phrap" (Phil Green, University of Washington, Seattle, Wash.).

Based on the sequence as described above, oligonucleotides were synthesized: 1) to identify by PCR a cDNA library that contained the sequence of interest, and 2) for use as probes to isolate a clone of the full-length coding sequence for PRO87299. Forward and reverse PCR primers generally range from 20 to 30 nucleotides and are often designed to give a PCR product of about 100-1000 bp in length. The probe sequences are typically 40-55 bp in length. In some cases, additional oligonucleotides are synthesized when the consensus sequence is greater than about 1-1.5 kbp. In order to screen several libraries for a full-length clone, DNA from the libraries was screened by PCR amplification, as per Ausubel et al., *Current Protocols in Molecular Biology,* supra, with the PCR primer pair. A positive library was then used to isolate clones encoding the gene of interest using the probe oligonucleotide and one of the primer pairs.

The oligonucleotide probes employed were as follows:

Forward primer: hBTig.EcoRI.F2 5' TTGAATTCATGAAGACATTGCCTGCCATGC 3' (SEQ ID NO: 11)

Reverse primer: hBTig.BamHI.R2 5' TTGGATCCTTAACTCCTCACACATATGGATGCATATTC 3' (SEQ ID NO: 12)

A human blood cDNA library was used in cloning. The cDNA library used to isolate the cDNA clones were constructed by standard methods using commercially available reagents such as those from Invitrogen, San Diego, Calif. The cDNA was primed with oligo dT containing a NotI site, linked with blunt to SalI hemikinased adaptors, cleaved with NotI, sized appropriately by gel electrophoresis, and cloned in a defined orientation into a suitable cloning vector (such as pRKB or pRKD; pRK5B is a precursor of pRK5D that does not contain the SfiI site; see, Holmes et al., *Science*, 253: 1278-1280 (1991)) in the unique XhoI and NotI sites.

The entire nucleotide sequence of the clone, designated herein as DNA332467, is shown in FIG. 1 (SEQ ID NO: 1). The DNA332467 clone contains a single open reading frame with an apparent translational initiation site at nucleotide positions 24-26 and a stop signal at nucleotide positions 891-893 (FIG. 1, SEQ ID NO:1). The predicted polypeptide precursor is 289 amino acids long, has a calculated molecular weight of approximately 32781 daltons and an estimated pI of approximately 6.27. Analysis of the full-length PRO87299 sequence shown in FIG. 2 (SEQ ID NO:2) evidences the presence of a variety of important polypeptide domains as shown in FIG. 2, wherein the locations given for those polypeptide domains are approximate as described.

An analysis of the current protein database, using the ALIGN-2 sequence alignment analysis of the full-length sequence shown in FIG. 2 (SEQ ID NO:2), evidenced sequence identity between the PRO87299 amino acid sequence and no known protein sequences.

Example 2

Cloning of PRO87299 Variants

PRO87299 was screened for sequence variants on B-cell RNA from 16 different donors. RT-PCR was performed on this RNA to produce the full length PRO87299. The PCR products were cloned into vectors that allowed for high throughput sequencing and analyzed by double-pass sequencing. Several PRO87299 variants showed minimal variation (FIGS. 11A-11I). However, a truncated version was found which has exon 3 deleted which deletes the transmembrane domain (FIG. 7, SEQ ID NO:7). The truncated version is deleted from nucleic acids 403-547 of the native protein, resulting in a variant PRO87299 polypeptide (FIG. 8, SEQ ID NO:8) that is only 241 amino acids in length, while the native PRO87299 is 289 amino acids in length. A lack of transmembrane domain may mean that this PRO87299 variant is a secreted form.

An additional PRO87299 variant was discovered, which comprises an 18 nucleotide base pair insertion at the 5' end of exon 3 (FIG. 9, SEQ ID NO:9). This 18 base pair insertion encodes for an additional 6 amino acids (AFTNIP), and is inserted into the PRO87299 encoding nucleic acid in frame, resulting in a variant PRO87299 polypeptide (FIG. 10, SEQ ID NO: 10) that is 295 amino acids in length. Both the short form and the AFTNIP form are shown along with other variants in FIGS. 12A-12C.

The IgG domain found at amino acids 51-117 of all PRO87299 polypeptide may be important to the function of the PRO87299 polypeptide.

Example 3

Microarray Analysis of Stimulated T-Cells

Nucleic acid microarrays, often containing thousands of gene sequences, are useful for identifying differentially expressed genes in diseased tissues as compared to their normal counterparts. Using nucleic acid microarrays, test and control mRNA samples from test and control tissue samples are reverse transcribed and labeled to generate cDNA probes. The cDNA probes are then hybridized to an array of nucleic acids immobilized on a solid support. The array is configured such that the sequence and position of each member of the array is known. For example, a selection of genes known to be expressed in certain disease states may be arrayed on a solid support. Hybridization of a labeled probe with a particular array member indicates that the sample from which the probe was derived expresses that gene. If the hybridization signal of a probe from a test (in this instance, activated CD4+ T cells) sample is greater than hybridization signal of a probe from a control (in this instance, non-stimulated CD4+ T cells) sample, the gene or genes overexpressed in the test tissue are identified. The implication of this result is that an overexpressed protein in a test tissue is useful not only as a diagnostic marker for the presence of the disease condition, but also as a therapeutic target for treatment of the disease condition.

The methodology of hybridization of nucleic acids and microarray technology is well known in the art. In one example, the specific preparation of nucleic acids for hybridization and probes, slides, and hybridization conditions are all detailed in PCT Patent Application Serial No. PCT/US01/10482, filed on Mar. 30, 2001 and which is herein incorporated by reference.

In this experiment, CD4+ T cells were purified from a single donor using the RossetteSep™ protocol from (Stem Cell Technologies, Vancouver BC) which contains anti-CD8, anti-CD16, anti-CD19, anti-CD36 and anti-CD56 antibodies used to produce a population of isolated CD4+ T cells. Isolated CD4+ T cells were activated with an anti-CD3 antibody (used at a concentration that does not stimulate proliferation) together with either ICAM-1 or anti-CD28 antibody. At 24 or 72 hours cells were harvested, RNA extracted and analysis run on Affimax™ (Affymetrix Inc. Santa Clara, Calif.) microarrays. Non-stimulated (resting) cells were harvested immediately after purification, and subjected to the same analysis. Genes were compared whose expression was upregulated at either of the two timepoints in activated vs. resting cells.

The result of these experiments, is that PRO87299 polypeptides of the present invention are significantly overexpressed in isolated CD4+ T cells activated by anti-CD3/ICAM-1 and anti-CD3/anti-CD28 as compared to isolated resting CD4+ T cells. As described above, these data demonstrate that the PRO87299 polypeptides of the present invention are useful not only as diagnostic markers for the presence of one or more immune disorders, but also serve as therapeutic targets for the treatment of those immune disorders.

Example 4

PRO87299 Lymphoma

Lymphoma is the 6th most common malignancy in the United States. There were an estimated 43,000 new cases of lymphoma in the United States in 1990. Non-Hodgkin's lymphoma accounts for the majority of cases, with Hodgkin's lymphoma cases a distant second. The incidence of Non-Hodgkin's lymphoma progressively increases with age. But in Hodgkin's disease, there is a high incidence in patients ages 20-30, a plateau between 30-55 and another rise after age 55. Males are higher at risk for both Hodgkin's disease and non-Hodgkin's lymphoma than females. The major clinical manifestation of malignant lymphoma is swelling of the lymph node and symptoms include fever, malaise, and weight loss. Common primary sites of lymphoma include supraclavicular, axillary, mediastinal, periaortic, cervical, and inguinal lymph nodes. Lymphoma also has the potential to metastasize to other organs.

Hodgkin's disease was first described by Thomas Hodgkin in 1832. Hodgkin's disease is an unrestricted proliferation of a lymphoid cell which becomes larger, with abundant pale cytoplasm and two or more oval lobulated nuclei containing large nucleoli. Cells of this appearance are known as Reed-Sternberg cells. Reed-Sternberg cells are important for the diagnosis of Hodgkin's disease, but their presence alone is not sufficient for diagnosis. Hodgkin's disease is distinct from non-Hodgkin lymphoma by cell type, lymph node histology, and by the symptomatology, such as fever. Hodgkin's disease generally presents as enlargement of a single group of peripheral lymph nodes, and may involve contiguous nodes, but is infrequently extranodal. The cause of Hodgkin's disease is unknown, but prior Epstein Barr Virus infection and bcl-2 translocations are associated with the development of Hodgkin disease.

The non-Hodgkin's lymphomas are neoplasms of the immune system arising in lymph nodes, but are differentiated from Hodgkin's disease by factors such as the cell type and the symptomatology exhibited by the patient. Most non-Hodgkin's lymphomas are of B cell phenotype and are positive for the markers CD19 and CD20. A smaller number are T cell lymphomas and are positive for the markers CD2 and CD3.

A proprietary database containing gene expression information (GeneExpress®, Gene Logic Inc., Gaithersburg, Md.) was analyzed in an attempt to identify if PRO87299 polypeptide (and its encoding nucleic acids) is significantly upregulated in lymphoma as compared to normal lymph tissues. Specifically, analysis of the GeneExpress® database was conducted using either software available through Gene Logic Inc., Gaithersburg, Md., for use with the GeneExpress® database or with proprietary software written and developed at Genentech, Inc. for use with the GeneExpress® database. The rating of positive hits in the analysis is based upon several criteria including, for example, tissue specificity, tumor specificity and expression level in normal essential and/or normal proliferating tissues. The result is that PRO87299 does evidence high expression in lymphoma as compared to other tumors and normal tissues.

Example 5

PRO87299 in Inflammatory Bowel Disease

In this experiment, a microarray assay was used to find genes that are overexpressed in IBD as compared to normal bowel tissue. Biopsies from patients with IBD were obtained. For each IBD patient, samples were taken from disease (either UC or Crohn's) tissue and from healthy bowel, so that expression patterns could be better compared. All samples were stored at −70° C. until ready for RNA isolation. The biopsies were homogenized in 600 µl of RLT buffer (+BME) and RNA was isolated using Qiagen™ Rneasy Mini columns (Qiagen™) with on-column DNase treatment following the manufacturer's guidelines. Following RNA isolation, RNA was quantitated using RiboGreen™ (Molecular Probes) following the manufacturer's guidelines and checked on agarose gels for integrity. Appropriate amounts of RNA were labeled for microarray analysis and samples were run on proprietary Genentech microarray and Affymetrics™ microarrays. Genes were compared whose expression was upregulated in IBD tissue vs normal bowel, matching biopsies from normal bowel and IBD tissue from the same patient. The results of this experiment showed that PRO87299 has been identified as being significantly overexpressed in Crohn's Disease samples as compared to normal bowel tissue.

Example 6

Expression of PRO87299 in NK Cells

Natural killer (NK) cells are an important effector cell of the innate immune system. They are specialized to effect killing against host cells that have either been infected by viruses, parasites or that have become cancerous. Phenotypically, NK cells are large granular lymphocytes that constitute ~2% of the circulating lymphocyte population. They are commonly identified by cell surface expression of CD56 and CD16. They mature in the bone marrow from a CD34+ precursor cell that they share with T cells. The mature NK cell, shares expression of CD8, cytolytic machinery, and some KIRs, with T cells, but remains distinct from T cells by the lack of CD3 and the T cell receptors. Like cytotoxic T cells, they contain granules filled with pore forming protein, cytotoxins, serine esterases and proteoglycans that mediate lysis of target cells. Both cytotoxic T cells and NK cells kill on contact by binding to their targets and delivering their lethal burst of chemicals that produces holes in the target cell's membrane. Unlike cytotoxic T cells, NK cells do not need to recognize a specific antigen before initiating lysis. Rather, NK cell activation can be mediated by growth factors and cytokines (in particular, IL-2, IL-12 and IL-15 have been shown to mediate proliferative and cytotoxic activities or by a delicate balance between two classes of NK cell receptors, one that activates the cells, and another that inhibits. Killer Ig-like receptors (KIRs) are NK cell receptors that transmit an inhibitory signal if they encounter class I MHC molecules on a cell surface. This is important for killing of both cancerous cells and virally infected cells. Because viruses often suppress class I MHC expression in cells they infect, the virus-infected cell becomes susceptible to killing by NK cells. Likewise, cancer cells have reduced or no class I MHC expression and they, too, become susceptible to killing by NK cells. Natural cytotoxicity receptors (NCRs) constitute a family of activating receptors on NK cells. In some effector-target systems, the surface density of NCRs correlates with the cytolytic activity of the NK cells, while in other systems killing requires cooperation between NCR, another activating receptor NKG2D and its adaptor polypeptide DAP10. Additionally, the strength of the signals can be influenced by engagement of coreceptors such as 2B4 and NTB-A. The ligands for NCRs and NKG2D, hemoglutanins and MICA, MICB respectively are not expressed by most normal cells, but are induced in most tumor cell lines. Expression of the ligands by tumor cells triggers a dramatic immune response resulting in tumor cell rejection. Activation of NK cells with IL-15 or IL-12 have been shown to induce both cytotoxic and proliferative effects. Junctional adhesion molecule 2 (JAM2) has been shown to bind to NK cells and has been hypothesized to play a role in lymphocyte extravasation to sites of inflammation.

Therefore, a DNA microarray experiment comparing differential expression of genes from these three modes of activation versus resting NK cells has the potential to reveal novel genes or novel gene associations with NK cell activity. Therapeutic antibodies, peptides or small molecules could be developed to target specific genes revealed by these microarrays for the treatment of immune mediated inflammatory diseases and malignancies. Peripheral blood NK cells were isolated from leukopacks by negative selection using the NK cell isolation kit with the MACS™ magnetic cell sorting system (Miltenyi Biotec). Cell purity was confirmed by staining with PE anti-CD56 for FACS analysis. Purity of cell preps ranged from 89% to 96%. Cell culture: Set up in-vitro cultures in 6 well plates 5 ml cultures/well.

Media: RPMI 1640, 10% heat inactivated FBS, 100 units/mL of Penicillin, 100 mg/mL of streptomycin, 2 mM L-glutamine, and 5.5×10−5 Beta-mercaptoethanol. Experimental treatments: Time 0 hrs, Untreated CD56(+) cells. Time 16 hrs. Untreated, IL2 (10 nM), IL15(10 nM), JAM-IT (10 nM) stimulated. Activation of NK cells was monitored by FACS for cell surface expression of CD56 and CD69. In this series of experiments it was determined that PRO87299 is expressed in CD56+ NK cells, when compared with normal resting NK cells.

Example 7

Use of PRO87299 as a Hybridization Probe

The following method describes use of a nucleotide sequence encoding PRO87299 as a hybridization probe.

DNA comprising the coding sequence of full-length or mature PRO87299 as disclosed herein is employed as a probe to screen for homologous DNAs (such as those encoding naturally-occurring variants of PRO87299) in human tissue cDNA libraries or human tissue genomic libraries.

Hybridization and washing of filters containing either library DNAs is performed under the following high stringency conditions. Hybridization of radiolabeled PRO87299-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence PRO87299 can then be identified using standard techniques known in the art.

Example 8

Expression of PRO87299 in *E. coli*

This example illustrates preparation of an unglycosylated form of PRO87299 by recombinant expression in *E. coli*.

The DNA sequence encoding PRO87299 is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the PRO87299 coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized PRO87299 protein can then be purified using a metal chelating column under conditions that allow tight binding of the protein.

PRO87299 may be expressed in *E. coli* in a poly-His tagged form, using the following procedure. The DNA encoding PRO87299 is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g (NH$_4$)$_2$SO$_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM MgSO$_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02 M, respectively, and the solution is stirred overnight at 4° C. This step results in a denatured protein with all cysteine residues blocked by sulfitolization. The solution is centrifuged at 40,000 rpm in a Beckman Ultracentifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80%. Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded PRO87299 polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

The PRO87299 polypeptides disclosed herein were successfully expressed as described above.

Example 9

Expression of PRO87299 in Mammalian Cells

This example illustrates preparation of a potentially glycosylated form of PRO87299 by recombinant expression in mammalian cells.

The vector, pRK5 (see EP 307,247, published Mar. 15, 1989), is employed as the expression vector. Optionally, the PRO87299 DNA is ligated into pRK5 with selected restriction enzymes to allow insertion of the PRO87299 DNA using ligation methods such as described in Sambrook et al., supra. The resulting vector is called pRK5-PRO87299.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-PRO87299 DNA is mixed with about 1 μg DNA encoding the VA RNA gene [Thimmappaya et al., Cell, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of PRO87299 polypeptide. The cultures containing transfected cells may undergo further incubation (in serum free medium) and the medium is tested in selected bioassays.

In an alternative technique, PRO87299 may be introduced into 293 cells transiently using the dextran sulfate method described by Somparyrac et al., Proc. Natl. Acad. Sci., 12:7575 (1981). 293 cells are grown to maximal density in a spinner flask and 700 μg pRK5-PRO87299 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 μg/ml bovine insulin and 0.1 μg/ml bovine transferrin. After about four days, the conditioned media is centrifuged and filtered to remove cells and debris. The sample containing expressed PRO87299 can then be concentrated and purified by any selected method, such as dialysis and/or column chromatography.

In another embodiment, PRO87299 can be expressed in CHO cells. The pRK5-PRO87299 can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of PRO87299 polypeptide, the culture medium may be replaced with serum free medium. Preferably, the cultures are incubated for about 6 days, and then the conditioned medium is harvested. The medium containing the expressed PRO87299 can then be concentrated and purified by any selected method.

Epitope-tagged PRO87299 may also be expressed in host CHO cells. The PRO87299 may be subcloned out of the pRK5 vector. The subclone insert can undergo PCR to fuse in frame with a selected epitope tag such as a poly-his tag into a Baculovirus expression vector. The poly-his tagged PRO87299 insert can then be subcloned into a SV40 promoter/enhancer containing vector containing a selection marker such as DHFR for selection of stable clones. Finally, the CHO cells can be transfected (as described above) with the SV40 promoter/enhancer containing vector. Labeling may be performed, as described above, to verify expression. The culture medium containing the expressed poly-His tagged PRO87299 can then be concentrated and purified by any selected method, such as by $Ni^{2+}$-chelate affinity chromatography.

PRO87299 may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g. extracellular domains) of the respective proteins are fused to an IgG1 constant region sequence containing the hinge, CH2 and CH2 domains and/or is a poly-His tagged form.

Following PCR amplification, the respective DNAs are subcloned in a CHO expression vector using standard techniques as described in Ausubel et al., Current Protocols of Molecular Biology, Unit 3.16, John Wiley and Sons (1997). CHO expression vectors are constructed to have compatible restriction sites 5' and 3' of the DNA of interest to allow the convenient shuttling of cDNA's. The vector used expression in CHO cells is as described in Lucas et al., Nucl. Acids Res. 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Quiagen), Dosper® or Fugene® (Boehringer Mannheim). The cells are grown as described in Lucas et al., supra. Approximately $3 \times 10^{-7}$ cells are frozen in an ampule for further growth and production as described below.

The ampules containing the plasmid DNA are thawed by placement into water bath and mixed by vortexing. The contents are pipetted into a centrifuge tube containing 10 mL of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3 \times 10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2 \times 10^6$ cells/mL. On day 0, pH is determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 µm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µl of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Many of the PRO87299 polypeptides disclosed herein were successfully expressed as described above.

Example 10

Expression of PRO87299 in Yeast

The following method describes recombinant expression of PRO87299 in yeast.

First, yeast expression vectors are constructed for intracellular production or secretion of PRO87299 from the ADH2/GAPDH promoter. DNA encoding PRO87299 and the promoter is inserted into suitable restriction enzyme sites in the selected plasmid to direct intracellular expression of PRO87299. For secretion, DNA encoding PRO87299 can be cloned into the selected plasmid, together with DNA encoding the ADH2/GAPDH promoter, a native PRO87299 signal peptide or other mammalian signal peptide, or, for example, a yeast alpha-factor or invertase secretory signal/leader sequence, and linker sequences (if needed) for expression of PRO87299.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant PRO87299 can subsequently be isolated and purified by removing the yeast cells from the fermentation medium by centrifugation and then concentrating the medium using selected cartridge filters. The concentrate containing PRO87299 may further be purified using selected column chromatography resins.

Many of the PRO87299 polypeptides disclosed herein were successfully expressed as described above.

Example 11

Expression of PRO87299 in Baculovirus-Infected Insect Cells

The following method describes recombinant expression of PRO87299 in Baculovirus-infected insect cells.

The sequence coding for PRO87299 is fused upstream of an epitope tag contained within a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the sequence encoding PRO87299 or the desired portion of the coding sequence of PRO87299 such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-his tagged PRO87299 can then be purified, for example, by Ni$^{2+}$-chelate affinity chromatography as follows. Extracts are prepared from recombinant virus-infected Sf9 cells as described by Rupert et al., Nature, 362:175-179 (1993). Briefly, Sf9 cells are washed, resuspended in sonication buffer (25 mL Hepes, pH 7.9; 12.5 mM MgCl$_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A Ni$^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline A280 with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching A280 baseline again, the column is developed with a 0 to 500 mM Imidazole gradient in the secondary wash buffer. One mL fractions are collected and analyzed by SDS-PAGE and silver staining or Western blot with Ni$^{2+}$-NTA-conjugated to alkaline phosphatase (Qiagen). Fractions containing the eluted His$_{10}$-tagged PRO87299 are pooled and dialyzed against loading buffer.

Alternatively, purification of the IgG tagged (or Fc tagged) PRO87299 can be performed using known chromatography techniques, including for instance, Protein A or protein G column chromatography.

Many of the PRO87299 polypeptides disclosed herein were successfully expressed as described above.

Example 12

Preparation of Antibodies that Bind PRO87299

Antibodies that specifically bind PRO87299 were generated by immunizing mice with PRO87299-Fc construct. This construct was made by ligating the region which encodes extracellular domain of PRO87299 (amino acids 1-155) into a plasmid containing a human Fc domain, thus making a PRO87299(ECD)-Fc chimera. This protein was produced, purified and injected into the foot pad of mice.

Techniques for producing monoclonal antibodies are known in the art and are described, for instance, in Goding, supra. Mice, such as Balb/c, were immunized with the PRO87299(ECD)-Fc chimera emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice were boosted 10 to 12 days later with additional PRO87299(ECD)-Fc chimera emulsified in the selected adjuvant. Thereafter, for several weeks, the mice may also be boosted with additional immunization injections. Serum samples were periodically obtained from the mice by retro-orbital bleeding for testing in ELISA assays to detect anti-PRO87299 antibodies.

After a suitable antibody titer was detected, the animals "positive" for antibodies were injected with a final intravenous injection of PRO87299(ECD)-Fc chimera. Three to four days later, the mice were sacrificed and the spleen cells are harvested. The spleen cells were then fused (using 35% polyethylene glycol) to a selected murine myeloma cell line such as P3X63AgU.1, available from ATCC, No. CRL 1597. The fusions generate hybridoma cells which were then plated in 96 well tissue culture plates containing HAT (hypoxanthine, aminopterin, and thymidine) medium to inhibit proliferation of non-fused cells, myeloma hybrids, and spleen cell hybrids.

The hybridoma cells were screened in an ELISA for reactivity against PRO87299. Nine antibodies were generated which specifically bound to PRO87299. The positive hybridoma cells were injected intraperitoneally into syngeneic Balb/c mice to produce ascites containing the anti-PRO87299 monoclonal antibodies. Alternatively, the hybridoma cells can be grown in tissue culture flasks or roller bottles. Purification of the monoclonal antibodies produced in the ascites was accomplished using ammonium sulfate precipitation, followed by gel exclusion chromatography. Alternatively, affinity chromatography based upon binding of antibody to protein A or protein G can be employed.

As stated previously, nine (9) antibodies were generated that specifically bound to PRO87299. Of these nine, the antibody designated 5F5.1, was determined to be an agonist antibody. Agonist activity was determined by inhibition of CD4+ T cell proliferation. CD 4+ T cells were isolated from human blood as previously described in Example 2, and cultured with cross-linked plate bound antibodies. 96 well plates were prepared by incubating overnight at 37° C. with goat-anti-mouse IgG at a concentration of 10 µg/ml and washed with PBS to remove excess. Anti-CD3/anti-CD28 antibodies were added to the IgG coated plates with or without the anti-PRO87229 antibody. The combination of anti-CD3 (0.1 µg/ml) and anti-CD28 (0.25 µg/ml) stimulate CD4+ T cell proliferation, and the addition of the anti-PRO87299 antibody reduced proliferation 5 fold as measured by thymidine uptake (FIG. 13). Anti-CD3 antibody alone showed no proliferation, and a control antibody also showed no proliferation. The agonist activity of the 5F5.1 anti-PRO87299 antibody could be abolished by heat inactivation. The 5F5.1 hybridoma line is deposited with the ATCC under the Budapest Treaty (see Example 19).

A second experiment was performed using soluble antibodies. Anti-CD3 (10 µg/ml) and anti-CD28 (5 µg/ml) when added to the cell culture media also showed increase in CD 4+ T cell proliferation. Anti-PRO87299 antibody added into the cell culture media with the two stimulatory antibodies showed inhibition of CD4+ T cell proliferation up to 50%. The range of anti-PRO87299 antibody used was 5-200 µg/ml, and inhibition of CD4+ cell proliferation was dose dependant in this range.

An antibody that specifically binds PRO87299 but does not have an agonistic effect is antibody 5E10. This antibody was shown to recognize PRO87299 on primary B cells and CD4+ T cells. It could also recognize PRO87299 transfected cells using FACS analysis. The 5E10 antibody consistently had no agonistic effect.

Therefore, antibodies that specifically bind PRO87299 have been generated. Anti-PRO87299 antagonist antibodies have utility in stimulating an immune response which would be useful in treating immune deficiencies and warding off infection by pathogens. Anti-PRO87299 agonist antibodies have utility in reducing the proliferation of CD4+ T cells therefore, decreasing the immune response, and would be useful in treating autoimmune diseases, lymphoma and inflammatory bowel disease.

Example 13

Purification of PRO87299 Polypeptides Using Specific Antibodies

Native or recombinant PRO87299 polypeptides may be purified by a variety of standard techniques in the art of protein purification. For example, pro-PRO87299 polypeptide, mature PRO87299 polypeptide, or pre-PRO87299 polypeptide is purified by immunoaffinity chromatography using antibodies specific for the PRO87299 polypeptide of interest. In general, an immunoaffinity column is constructed by covalently coupling the anti-PRO87299 polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of PRO87299 polypeptide by preparing a fraction from cells containing PRO87299 polypeptide in a soluble form. This preparation is derived by solubilization of the whole cell or of a subcellular fraction obtained via differential centrifugation by the addition of detergent or by other methods well known in the art. Alternatively, soluble PRO87299 polypeptide containing a signal sequence may be secreted in useful quantity into the medium in which the cells are grown.

A soluble PRO87299 polypeptide-containing preparation is passed over the immunoaffinity column, and the column is washed under conditions that allow the preferential absorbance of PRO87299 polypeptide (e.g., high ionic strength buffers in the presence of detergent). Then, the column is eluted under conditions that disrupt antibody/PRO87299 polypeptide binding (e.g., a low pH buffer such as approximately pH 2-3, or a high concentration of a chaotrope such as urea or thiocyanate ion), and PRO87299 polypeptide is collected.

Example 14

Drug Screening

This invention is particularly useful for screening compounds by using PRO87299 polypeptides or binding fragment thereof in any of a variety of drug screening techniques. The PRO87299 polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the PRO87299 polypeptide or fragment. Drugs are screened against such transformed cells in competitive binding assays. Such cells, either in viable or fixed form, can be used for standard binding assays. One may measure, for example, the formation of complexes between PRO87299 polypeptide or a fragment and the agent being tested. Alternatively, one can examine the diminution in complex formation between the PRO87299 polypeptide and its target cell or target receptors caused by the agent being tested.

Thus, the present invention provides methods of screening for drugs or any other agents which can affect a PRO87299 polypeptide-associated disease or disorder. These methods comprise contacting such an agent with an PRO87299 polypeptide or fragment thereof and assaying (i) for the presence of a complex between the agent and the PRO87299 polypeptide or fragment, or (ii) for the presence of a complex between the PRO87299 polypeptide or fragment and the cell, by methods well known in the art. In such competitive binding assays, the PRO87299 polypeptide or fragment is typically labeled. After suitable incubation, free PRO87299 polypeptide or fragment is separated from that present in bound form, and the amount of free or uncomplexed label is a measure of the ability of the particular agent to bind to PRO87299 polypeptide or to interfere with the PRO87299 polypeptide/cell complex.

Another technique for drug screening provides high throughput screening for compounds having suitable binding affinity to a polypeptide and is described in detail in WO84/03564, published on Sep. 13, 1984. Briefly stated, large numbers of different small peptide test compounds are synthesized on a solid substrate, such as plastic pins or some other surface. As applied to a PRO87299 polypeptide, the peptide test compounds are reacted with PRO87299 polypeptide and washed. Bound PRO87299 polypeptide is detected by methods well known in the art. Purified PRO87299 polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding PRO87299 polypeptide specifically compete with a test compound for binding to PRO87299 polypeptide or fragments thereof. In this manner, the antibodies can be used to detect the presence of any peptide which shares one or more antigenic determinants with PRO87299 polypeptide.

Example 15

Rational Drug Design

The goal of rational drug design is to produce structural analogs of biologically active polypeptide of interest (i.e., a PRO87299 polypeptide) or of small molecules with which they interact, e.g., agonists, antagonists, or inhibitors. Any of these examples can be used to fashion drugs which are more active or stable forms of the PRO87299 polypeptide or which enhance or interfere with the function of the PRO87299 polypeptide in vivo (c.f., Hodgson, *Bio/Technology*, 9: 19-21 (1991)).

In one approach, the three-dimensional structure of the PRO87299 polypeptide, or of a PRO87299 polypeptide-inhibitor complex, is determined by x-ray crystallography, by computer modeling or, most typically, by a combination of the two approaches. Both the shape and charges of the PRO87299 polypeptide must be ascertained to elucidate the structure and to determine active site(s) of the molecule. Less often, useful information regarding the structure of the PRO87299 polypeptide may be gained by modeling based on the structure of homologous proteins. In both cases, relevant structural information is used to design analogous PRO87299 polypeptide-like molecules or to identify efficient inhibitors. Useful examples of rational drug design may include molecules which have improved activity or stability as shown by Braxton and Wells, *Biochemistry*, 31:7796-7801 (1992) or which act as inhibitors, agonists, or antagonists of native peptides as shown by Athauda et al., *J. Biochem.*, 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the PRO87299 polypeptide may be made available to perform such analytical studies as X-ray crystallography. In addition, knowledge of the PRO87299 polypeptide amino acid sequence provided herein will provide guidance to those employing computer modeling techniques in place of or in addition to x-ray crystallography.

Example 16

PRO87299 Specifically Binds HVEM

Figure 14:
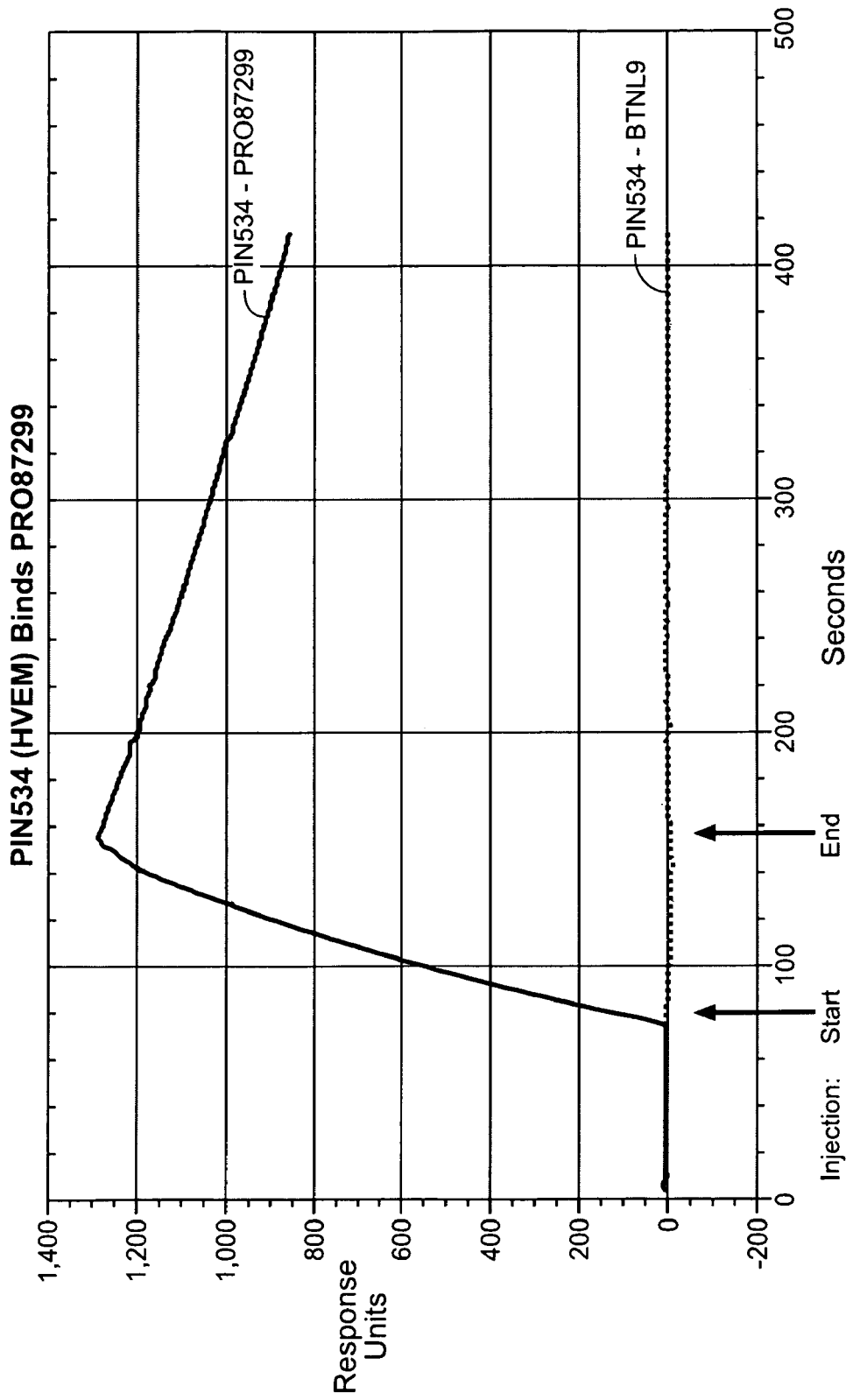
FIG. 14 shows the specific binding of PRO87299 to HVEM

Protein library screening determines that PRO87299 binds specifically to HVEM. The extracellular domain of PRO87299 was fused to human Fc to create PRO87299 (ECD)-Fc. This fusion protein was amine coupled to a Biacore™ (BIAcore, Inc., Piscataway, N.J.) CM5 sensor chip at approximately 9000 response units as described generally in Chen, Y. et al., *J. Mol. Biol* 293:865-881 (1999). Briefly, carboxymethylated dextran biosensor chips (CM5, BIAcore™ Inc.) were activated with N-ethyl-N'-(3-dimethylaminopropyl)-carbodiimide hydrochloride (EDC) and N-hydroxysuccinimide (NHS) according to the supplier's instructions. PRO87299(ECD)-Fc was diluted and injected at a flow rate to achieve approximately 9000 response units (RU) of coupled protein. In a second flow cell on the same chip a control protein, human PRO4346-Fc (Genbank Accession number AK057097), was amine coupled at approximately 18500 response units. An injection of 1M ethanolamine was done to block unreacted groups. Individual proteins from the SPDI protein library, consisting of approximately 2000 proteins were then injected at a concentration of 2 µg/ml and binding was assessed by the change in response units as a function of time. HVEM was found to bind PRO87299 (ECD)-Fc, but not control PRO4346-Fc. As shown in FIG. 14 the association of PRO87299 and HVEM results in a highly significant increase of 1200 response units over control. Association rates ($k_{on}$) and dissociation rates ($k_{off}$) were calculated using a simple one-to-one Langmuir binding model (BIAcore™ Evaluation Software version 3.2) by simultaneous fitting the association and dissociation sensorgram. The equilibrium dissociation constant (Kd) was calculated as the ratio $k_{off}/k_{on}$.

Figure 15:
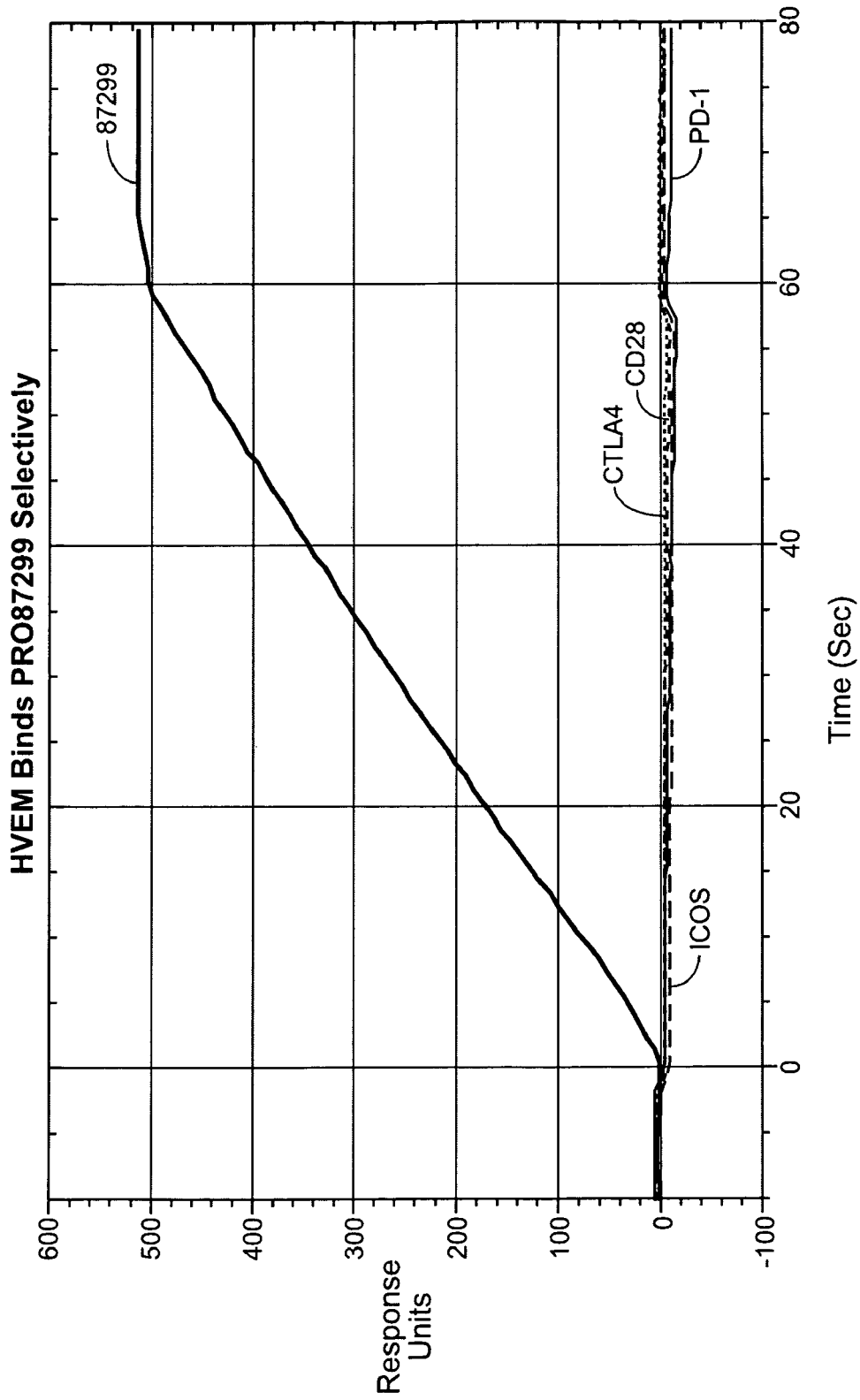
FIG. 15 shows the binding of PRO87299 to HVEM when compared to other family members

PRO87299 binds selectively to HVEM as shown in FIG. 15. In this experiment, PRO87299(ECD)-Fc and CD28 family members hCTLA4-Fc, hPD-1-Fc, hICOS-Fc or hCD28-Fc were amine coupled to a Biacore™ CM5 chip at approximately 8000 response units. Each was then assayed for its ability to bind HVEM. An HVEM-Fc protein was made by ligating the nucleic acids encoding amino acids 1-199 of HVEM to a Fc, resulting in a HVEM-Fc fusion protein. This HVEM-Fc was cloned into an a expression vector which would produce the fusion protein when stably transfected into CHO cells. All Fc-tagged proteins were purified to greater than 90% purity by affinity chromatography using Protein A Sepharose™ (Amersham). The result was 2 µg/ml of HVEM-Fc injected at 5 µl/min bound selectively to PRO87299 and not to the other member of the CD28 family members tested. The activity of each CD28 family member was confirmed positive by testing the binding response to their known ligands (data not shown) (CD28 family members and ligands were purchased from R&D systems).

Figure 16:
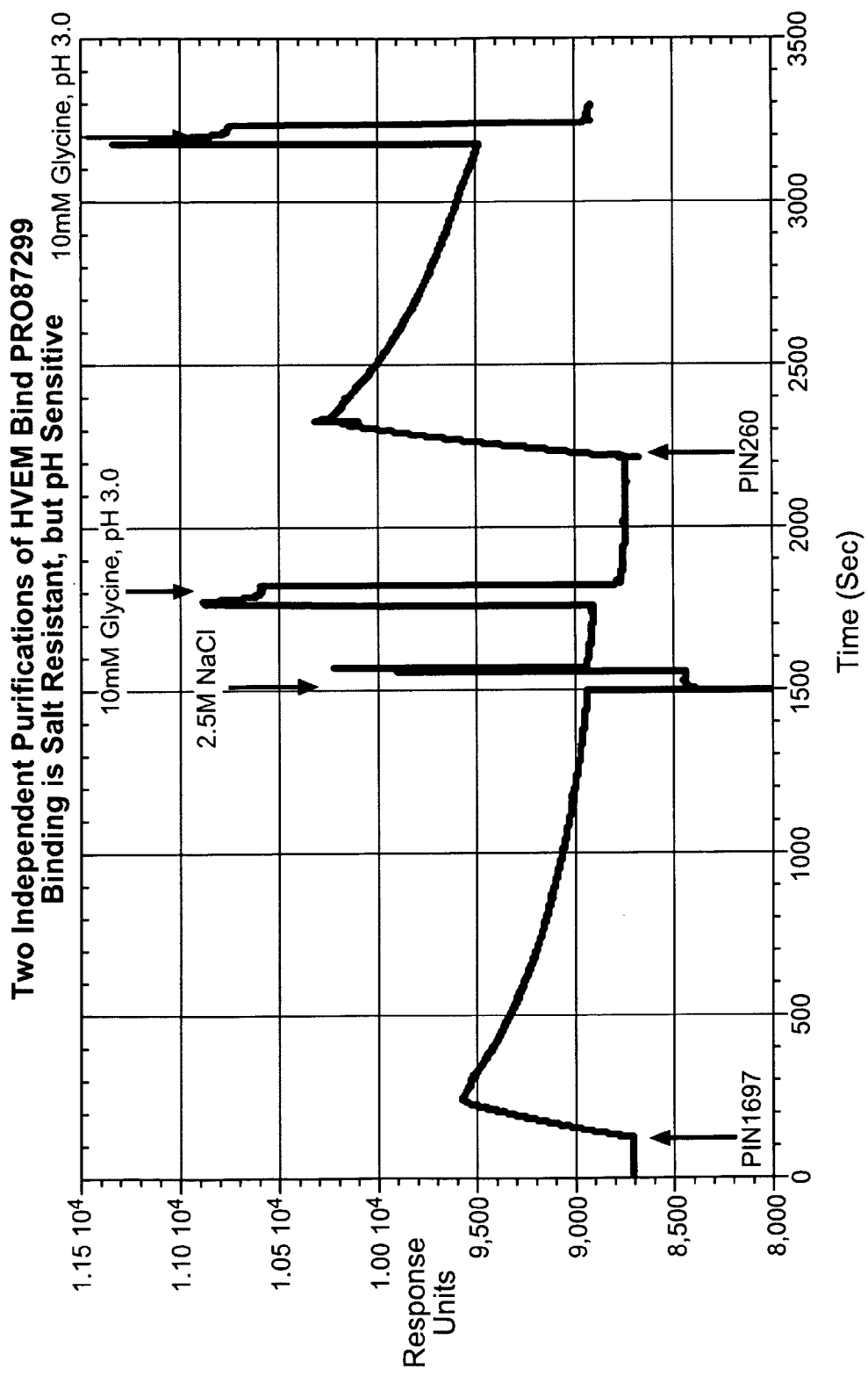
FIG. 16 shows the binding of PRO87299 to HVEM is sensitive to pH.

PRO87299 binding to HVEM is pH dependant but NaCl concentration independent. Using the Biacore™ assay as described above, two independent purifications of HVEM-Fc bind PRO87299 amine coupled to a Biacore™ CM5 chip. As shown in FIG. 16, binding was not disrupted by treatment with 2.5M NaCl; but the PRO87299/HVEM complex could be dissociated with 10 mM glycine at pH 3.0.

Figure 18:
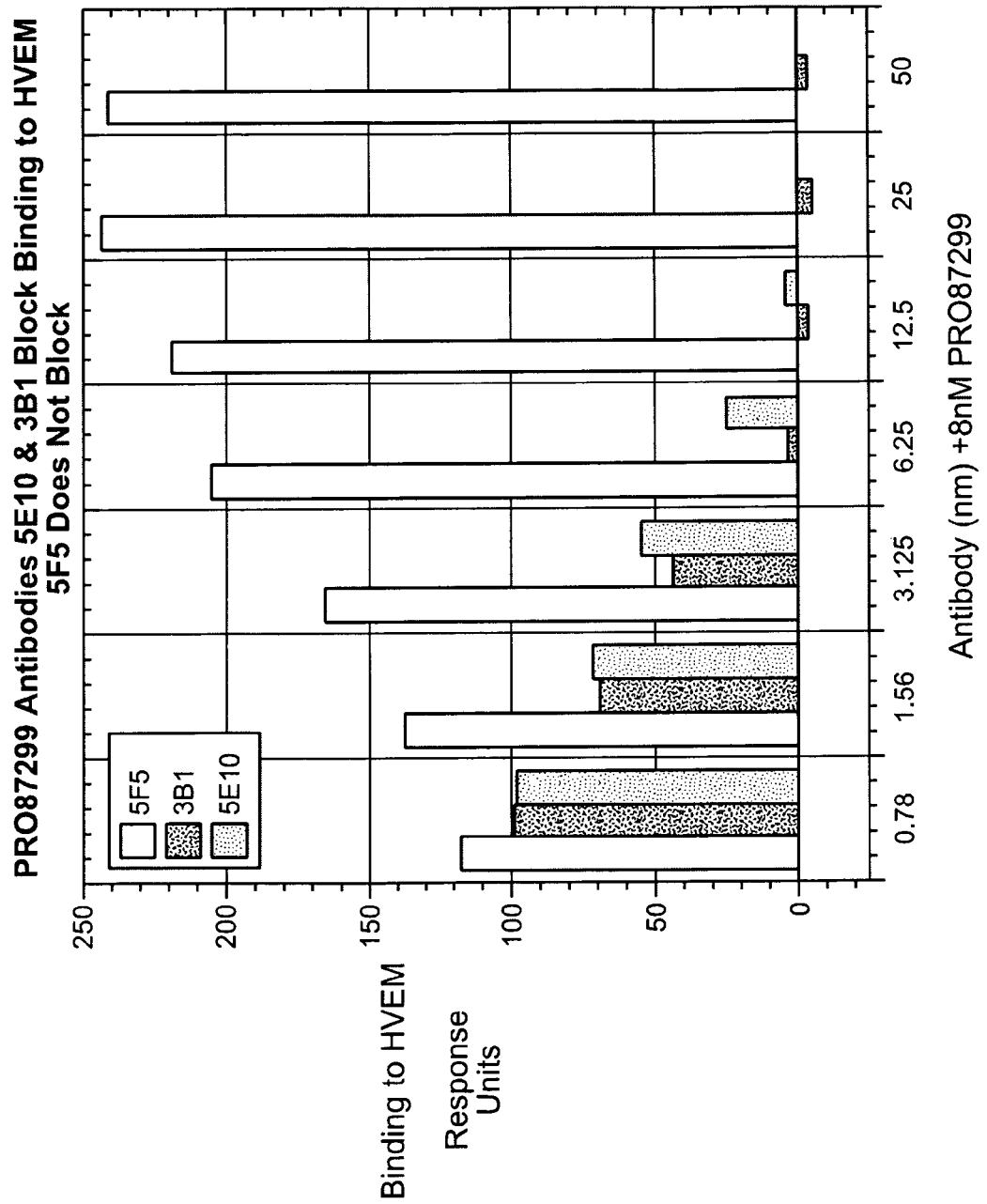
FIG. 18 shows that antibodies to PRO87299 can block the interaction with HVEM.

PRO87299/HVEM interaction can be blocked by antibodies to PRO87299. In this experiment, HVEM-Fc was amine coupled to a Biacore™ CM5 sensor chip at approximately 7500 response units. Injections of PRO87299(ECD)-Fc were performed at two minutes at a 5 µl/min flow rate. Response units (RU) were recorded 105 seconds after injection. PRO87299(ECD)-Fc (8 nM) gave a response of 100 RUs. Each antibody, at increasing concentration, was premixed with PRO87299(ECD)-Fc (8 nM) and incubated for 1 hr. Binding of each sample was then measured in random order and in duplicate, and 10 mM Glycine pH 2.5 was used to regenerate the binding surface after each injection. As shown in FIG. 18, anti-PRO87299 antibodies 5E10 and 3B1.9 block the binding of PRO87299 to HVEM in a concentration dependant manner, while the agonist antibody 5F5.1 has no blocking effect. Injections of antibodies alone showed no binding to the immobilized HVEM (data not shown). Concentrations were calculated based on the apparent reduced molecular weight of PRO87299(ECD)-Fc (55 kDa) and an antibody mass of 150 kDa.

Figures 17A, 17B:
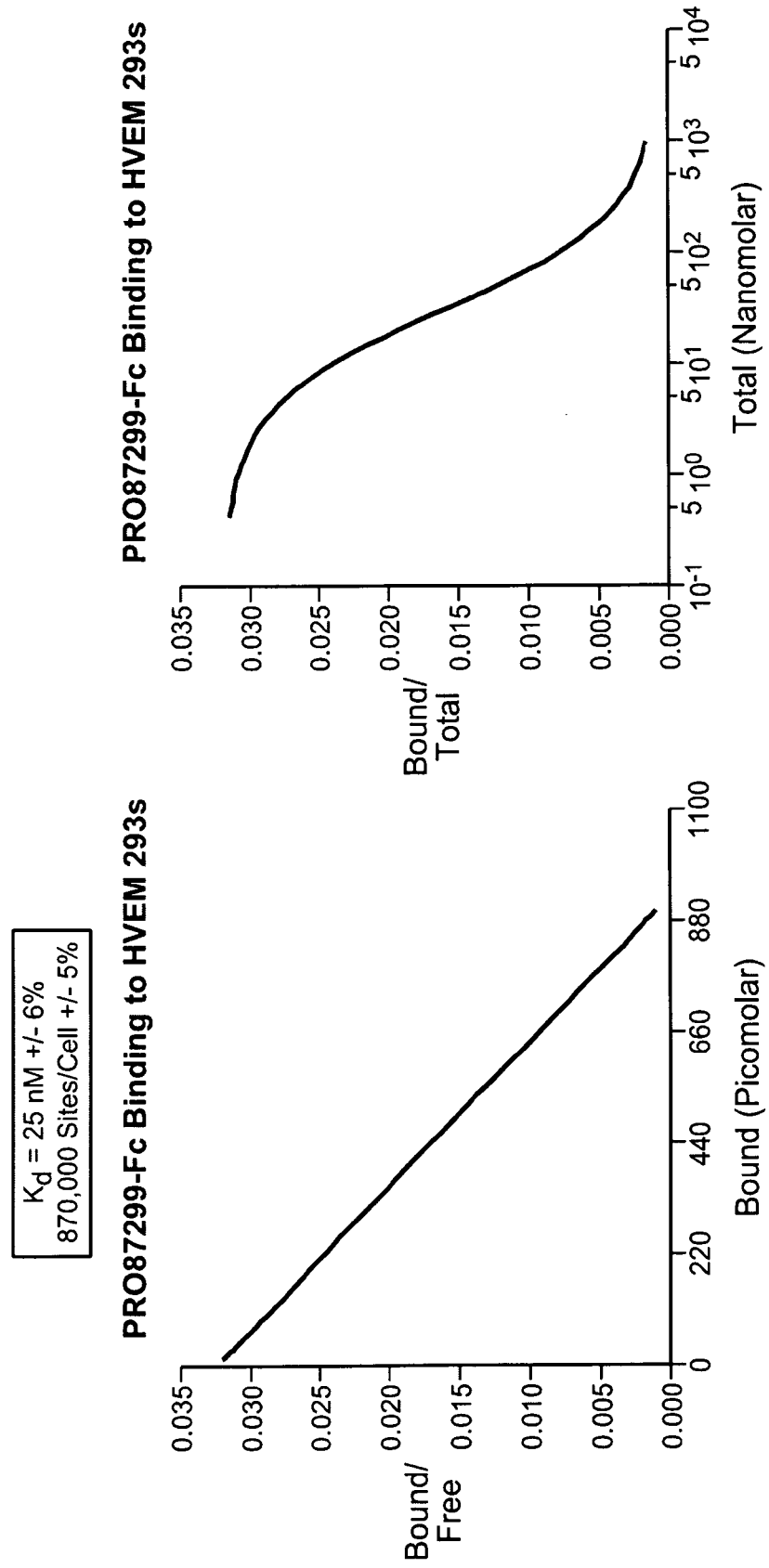
FIG. 17 shows the binding PRO87299 to HVEM on cells transfected with HVEM.

PRO87299 binds to HVEM in a cell based assay. In this experiment human 293 cells (ATCC CCL 1573) are grown to confluence in tissue culture plates in medium such as DMEM supplemented with fetal calf serum and optionally, nutrient components and/or antibiotics. About 10 µg pRK5-HVEM DNA is mixed with about 1 µg DNA encoding the VA RNA gene [Thimmappaya et al., *Cell*, 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days. Alternatively, about 10 µg pRK5-HVEM DNA is mixed with LipofectAMINE™ (Gibco/BRL, Gaithersburg Md.) reagent and transfection performed by following the manufacturer's instructions. After the 293 cells were transfected with HVEM, they were incubated with $I^{125}$ radiolabled PRO87299(ECD)-Fc and binding allowed to occur. The radiolabled PRO87299 was then competed off with unlabed PRO87299(ECD)-Fc and the estimated number of total binding sites and the dissociation constant (Kd) were determined by Scatchard analysis. FIG. 17(A) is a Scatchard plot and FIG. 17(B) is a displacement plot showing PRO87299(ECD)-Fc binding to HVEM transiently transfected cells. This data shows that the Kd of PRO87299 is about 25 nM. Total binding of radiolabled-PRO87299(ECD)-

Fc to mock transfected 293 HEK cells was 2.5% of that to HVEM transfected cells (data not shown). Using this methodology, the affinity of HVEM/LIGHT/PRO87299 interactions were determined. This is shown in Table 7 below.

TABLE 7

| Expressed protein | Ligand | Kd (nM) |
|---|---|---|
| HVEM | I-125-PRO87299-Fc | 25 |
| HVEM | I-125-LIGHT-FLAG | 2.5 |
| PRO87299 | I-125-HVEM-Fc | 5.5 |
| LIGHT | I-125-HVEM-Fc | 7 |
| PRO87299/LIGHT | I-125-HVEM-Fc | 0.5 |

Anti-PRO87299 antibody (3B1.9) dose-dependently competed with PRO87299(ECD)-Fc binding to HVEM as discussed previously in this Example.

Taken together, this data shows that PRO87299 binds specifically to HVEM as determined by assaying via protein-protein interaction, protein-antibody blocking and in vivo analysis.

Example 17

PRO87299 and LIGHT Can Bind HVEM Simultaneously

Figure 19:
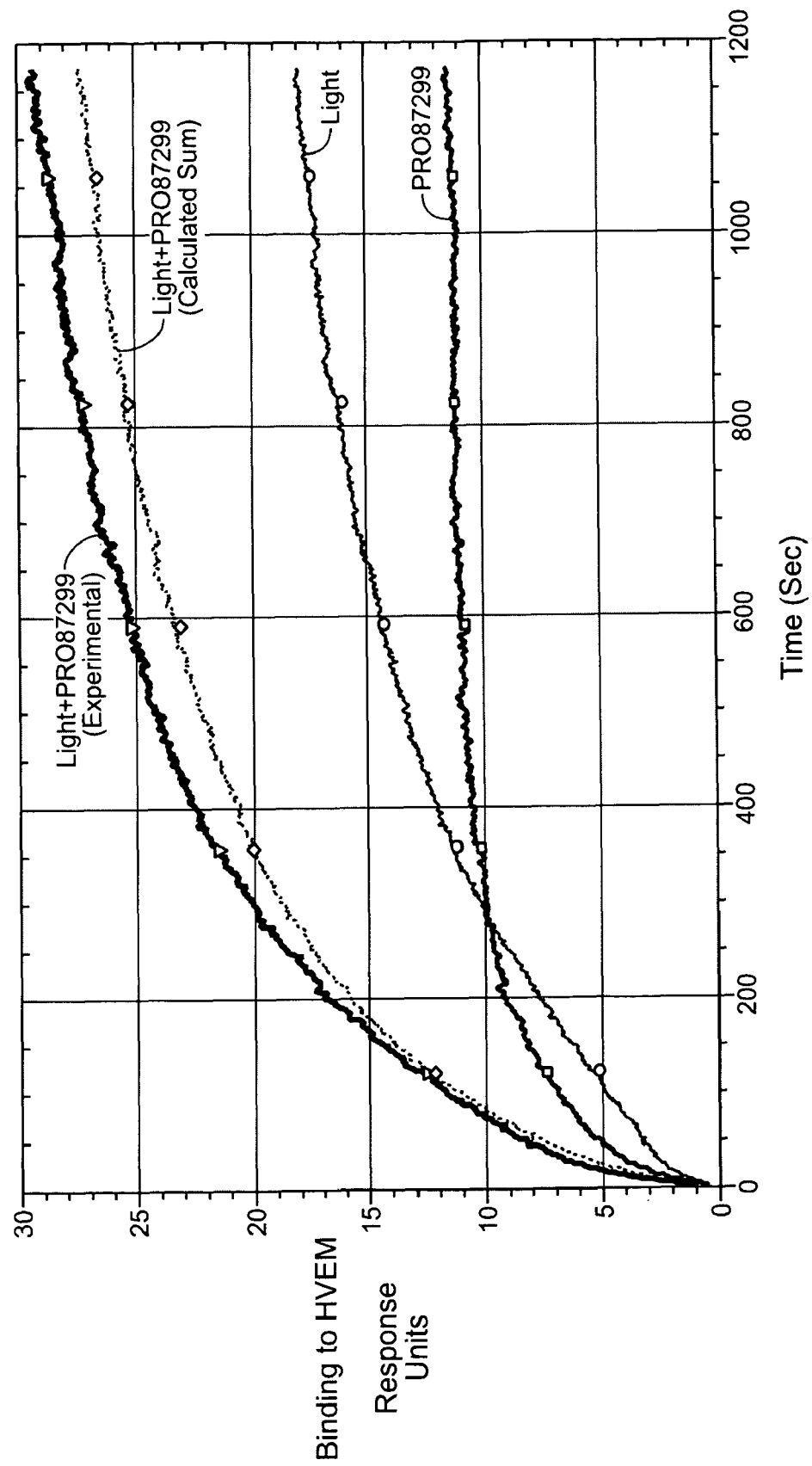
FIG. 19 shows that PRO87299 and LIGHT can bind HVEM simultaneously

Publications have shown that LIGHT (GenBank Accession No: NM_172014, SEQ ID NO:5, SEQ ID NO:6) can bind to HVEM (Marsters, S. A. et al., Curr. Biol. 8 (9), 525-528 (1998). Mauri D. N. et al., Immunity (8), 21-30, (1998)). To confirm that LIGHT and PRO87299 can bind HVEM simultaneously, we performed a co-binding experiment. HVEM-Fc was amine coupled to the Biacore™ CM5 sensor chip at a ~150 response units. The lower amount of immobilized HVEM-Fc was important in order to reach near saturation binding of PRO87299-Fc. FIG. 19 shows that LIGHT (25 nM) and PRO87299-Fc (17 nM) were injected independently at 5 μl/min for 1200 seconds (red and blue curves, respectively). Then a mixture of LIGHT and PRO87299-Fc at the same final concentrations was injected in an identical manner (green curve). The calculated sum of the individually injected LIGHT and PRO87299-Fc sensograms (grey curve) closely matched the experimental data, confirming that LIGHT and PRO87299 are capable of binding HVEM simultaneously. Concentrations were based on the LIGHT monomer molecular weight of 25 kDa and the reduced molecular weight of PRO87299-Fc (55 kDa).

PRO87299 interaction to HVEM is not blocked by LIGHT. PRO87299-Fc was amine coupled to a Biacore™ CM5 sensor chip at ~9800 response units. LIGHT (purchased from Alexis™, Cat. #552-018-C010) was incubated at the increasing concentrations with 4 nM HVEM for 1 hr. As shown in FIG. 20, PRO87299-Fc/HVEM binding is not blocked by increasing concentrations of LIGHT to a final concentration of 300 nM. LIGHT activity was confirmed by binding to immobilized HVEM-Fc on a CM5 sensor chip (data not shown). LIGHT alone did not bind to immobilized PRO87299-Fc (data not shown). All binding sensograms were run in random order and in duplicate. Response units were recorded as the difference between baseline and 15 seconds before the end of a 2 min injection at 5 μl/min. Concentrations are based on molecular weights of 25 kDa for LIGHT monomer and 55 kDa for monomer HVEM. This data shows that LIGHT does not block HVEM binding to PRO87299.

Figure 21A:
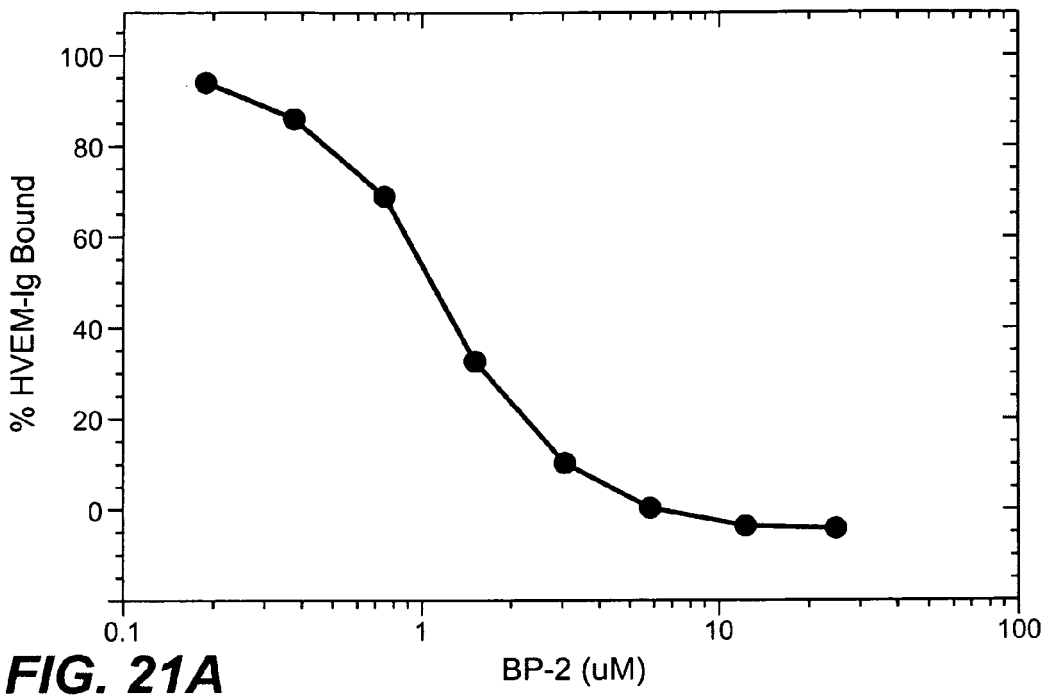
FIG. 21 shows BP-2 peptide and gD blocking PRO87299/HVEM interaction
Figure 21B:
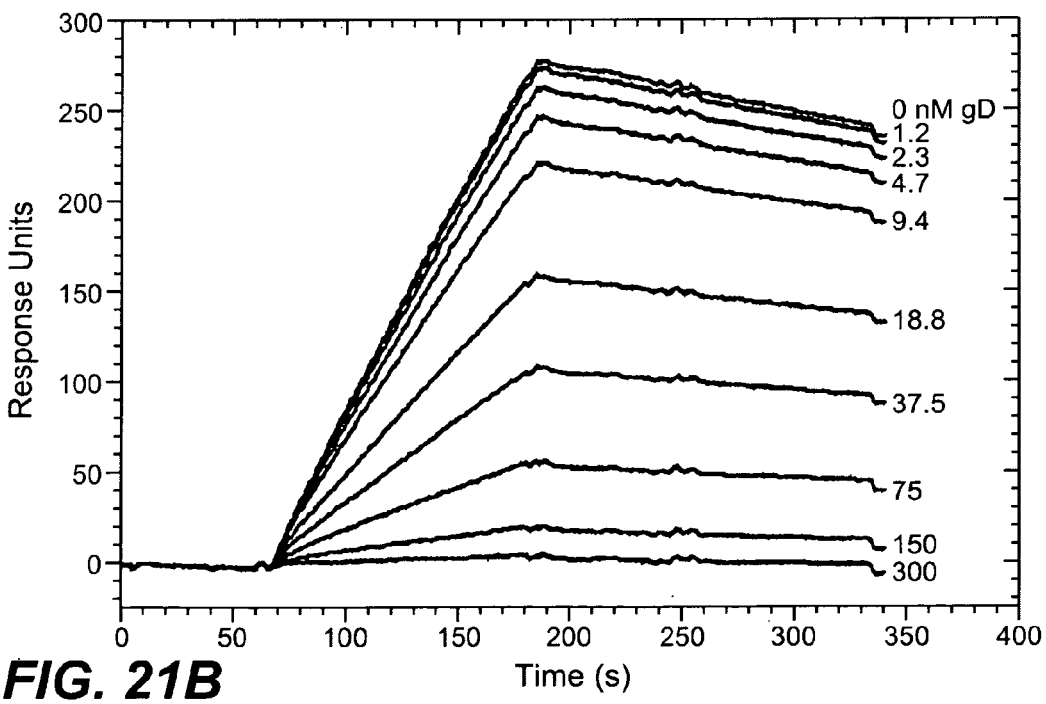
Figure 21D:
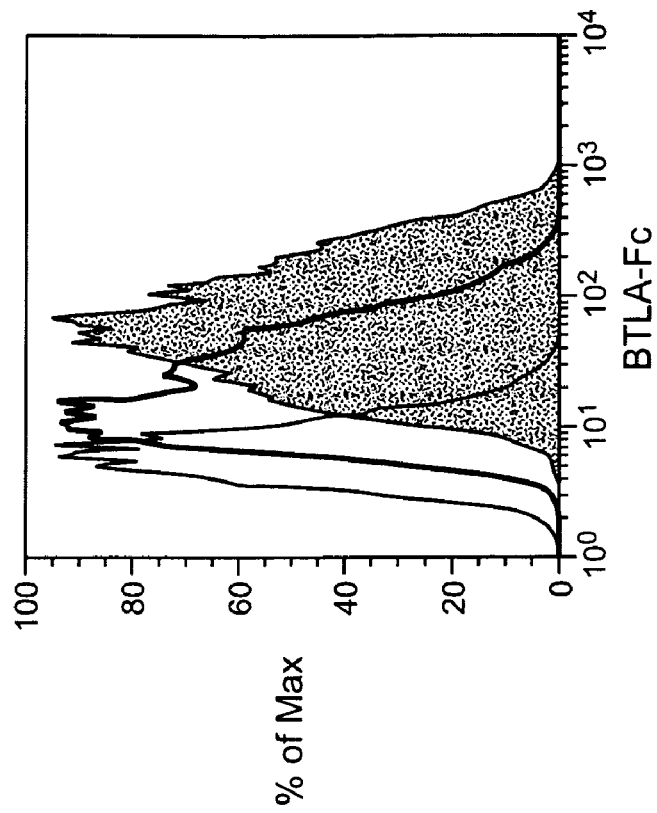
Figure 21C:
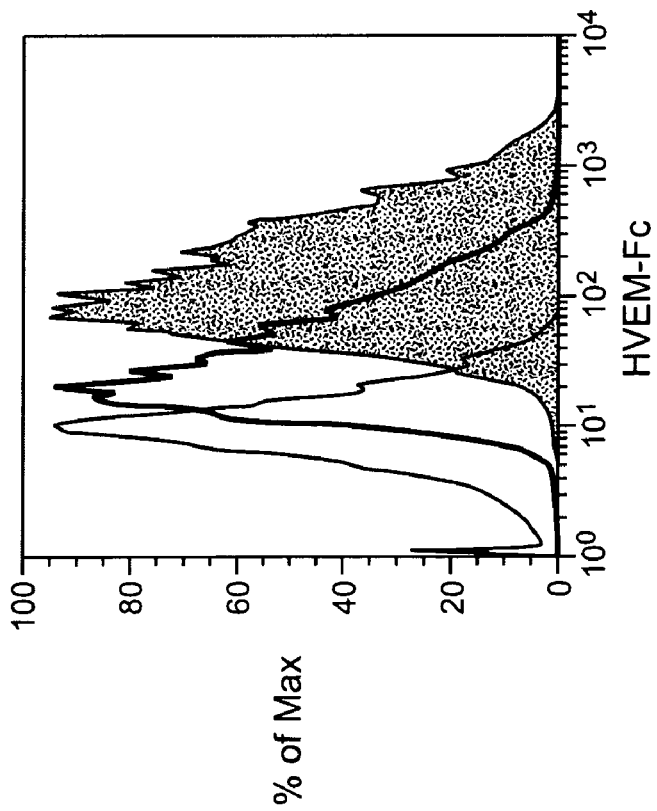

HVEM was initially identified as the cellular receptor for the entry of herpes simplex virus-1 (HSV-1) into the cell, and was shown to bind the HSV-1 glycoprotein D (gD) (Mongomery et al., Cell 87:427-436 (1996)). HVEM contains three cysteine rich domains (CRD) which is a common structural feature to all TNFR family members. Resolution of the crystal structure of gD protein complexed with HVEM showed that the first CRD of HVEM binds the gD protein, while the second CRD of HVEM provides structural support for the first CRD (Carfi et al., Mol. Cell. 8: 169-179 (2001)). The result is PRO87299 interacts with LIGHT and does not compete for HVEM binding, lead to the hypothesis that PRO87299 interacts with the outside surface of the HVEM/LIGHT complex. To test this hypothesis, a phage derived peptide (BP-2) that is capable of blocking HVEM binding to herpes glycoprotein D (gD), but not to LIGHT was generated (Sarrias et al., Mol. Immuno. 37:665-673: (2000)). At concentrations that inhibit gD binding, BP-2 inhibited the binding of PRO87299 to HVEM (FIG. 21A). In a direct comparison, a recombinant gD protein (Δ290-299 form. Milne et al., J. Virology. 77:8962-8972 (2003)) protein also inhibited HVEM binding to PRO87299 (FIG. 21B). This result was repeated in cell binding assays that show the recombinant gD (Δ290-299) inhibits the binding of soluble PRO87299-Fc and HVEM-Fc to 293 cells expressing HVEM or PRO87299 (FIGS. 21C and D respectively). These results indicate that PRO87299 interacts with the first CRD of HVEM on a site that is distinct from the LIGHT binding site. The discovery that PRO87299 interacts both with LIGHT and HVEM will allow the generation of antibodies or small molecules against HVEM that can selectively inhibit PRO87299/HVEM interaction without disrupting PRO87299/LIGHT interaction. Another type of antibody or small molecule that is contemplated by this discovery is one that will block both PRO87299/HVEM interaction and PRO87299/LIGHT interaction. These two different classes of molecules may have different therapeutic effects.

Example 18

PRO87299 Inhibits T-Cell Activation

Figure 22A:
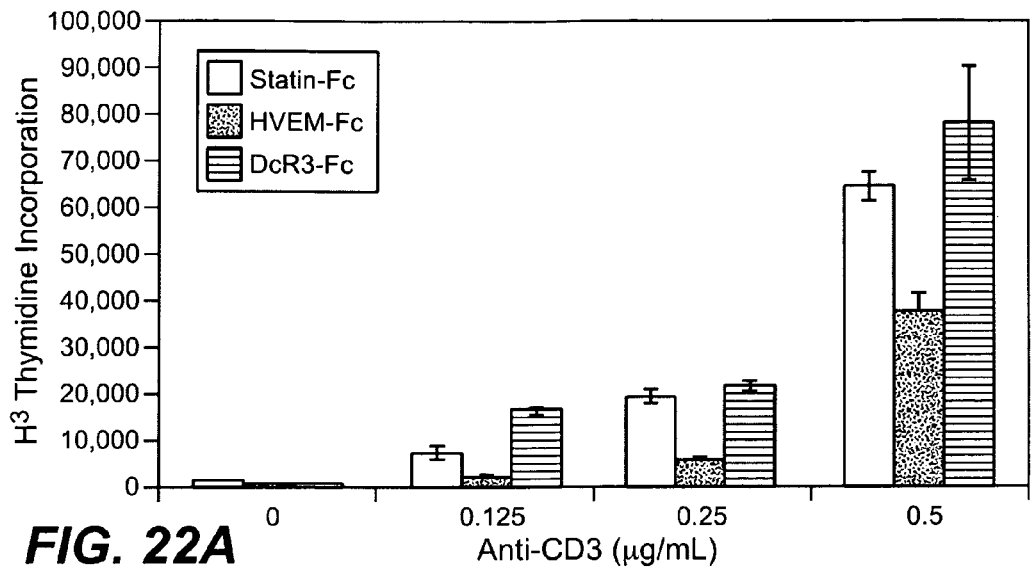
FIG. 22 shows PRO87299 inhibitory effect on CD4+ T cells.

As mentioned in Example 1, PRO87299 was cloned for further research into ITIM domain containing proteins. The intracellular domain of PRO87299 contains two ITIM domains that are inducibily phosphorylated, which allows for the recruitment and binding of SHP-1 and SHP-2, which indicates that the function of PRO87299 is inhibitory (Watanabe N., et al., Nature Immuno. 4:670-679 (2003)). In this experiment, primary CD4+ T cells were stimulated with different concentrations of immobilized anti-CD3 antibody. An Fc-tagged control protein, HVEM-Fc or DcR3-Fc were also crosslinked onto the plate by using a pre-coated anti-Fc antibody. The proliferation of the CD4+ Tcells was measured by H3 thymidine incorporation after a 72 hour incubation. This experiment was performed in triplicate wells, and the inhibition is shown as an average (FIG. 22A). HVEM was hypothesized to be inhibitory to T-cell proliferation due to its blocking of LIGHT. This experiment shows that it is not HVEM/LIGHT repression, but HVEM activating PRO87299 that causes the reduction of T-cell proliferation.

Figure 22B:
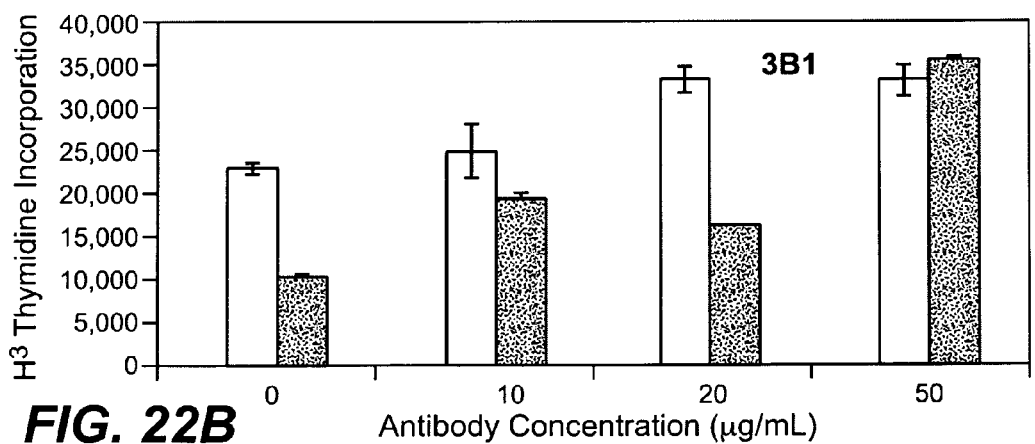
Figure 22C:
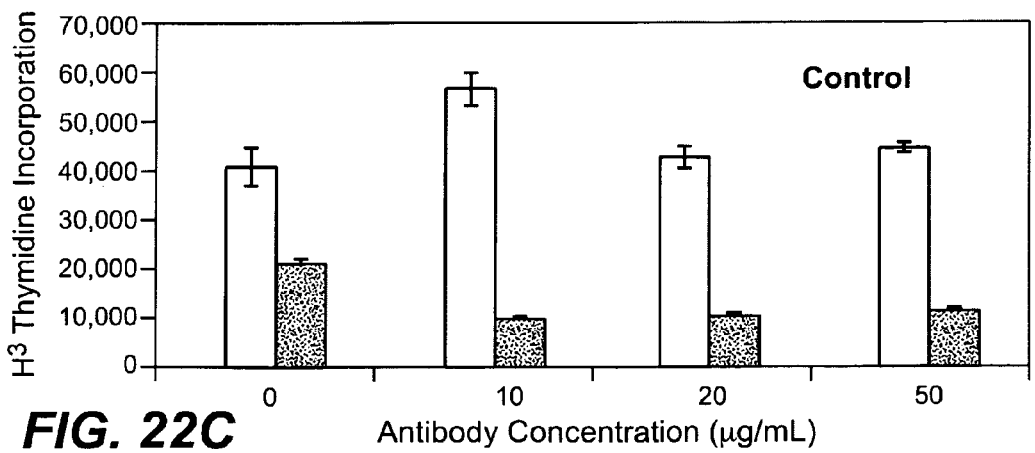

To further show that PRO87299 is inhibitory to T cell proliferation, the experiment was performed as described above, but including the inhibitory anti-PRO87299 antibody 3B1.9. 3B1.9 antibody was shown to block the binding of PRO87299 to HVEM (see Example 16). When CD4+ T cells were stimulated by plate immobilized anti-CD3 and +/−HVEM. The 3B1.9 antibody and a control antibody were then added to the media. The data shows the 3B1.9 antibody can interfere with the interaction of PRO87299/HVEM and thus relieve the cell of the inhibitory signal. The result is the 3B1.9 treated cells proliferated at the same rate as the untreated cells (FIG. 22B). Only when large concentrations of HVEM were used was the 3B1.9 antibody ineffective. This data demonstrates that PRO87299 or agonist antibodies could have utility in suppressing T cell related autoimmune diseases, or conversely, antagonist antibodies such as 3B1.9 would be useful in stimulating T cells to ward off infection by pathogens.

Example 19

Graft Verus Host Disease

Figure 23:
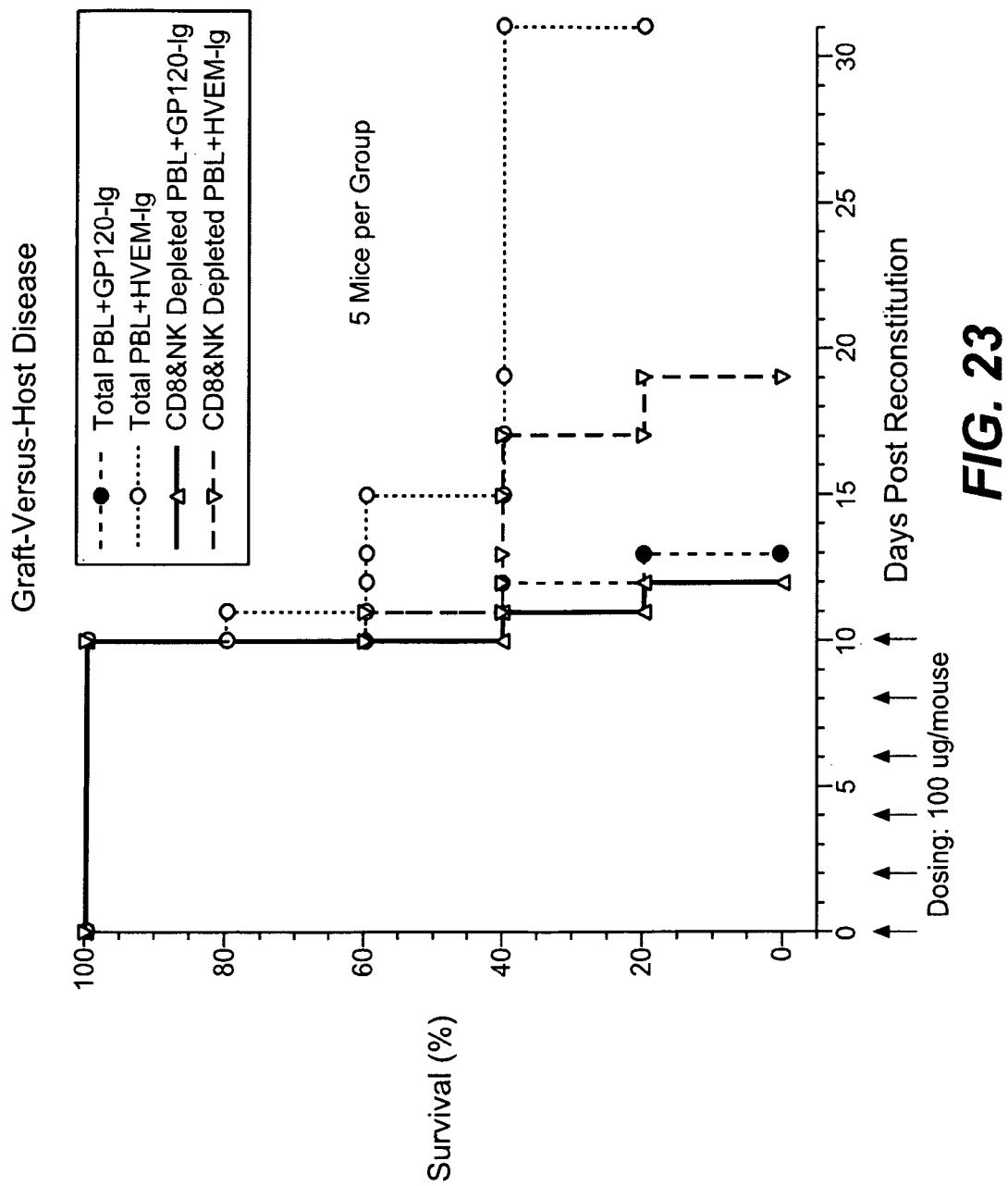
FIG. 23 shows the activation of PRO87299 by HVEM-Fc promotes survival in a GVHR model.

Graft-versus-host disease occurs when immunocompetent cells are transplanted into immunosuppressed or tolerant patients. The donor T cells recognize host antigens and become activated, secrete cytokines, proliferate and differentiate into effector cells. This response is known as graft-versus-host-reaction (GVHR). The GVHR response comprise a multiorgan syndrome and the effects can vary from life threatening severe inflammation to mild cases of diarrhea and weight loss. Graft-versus-host disease models in mice have been used to model the clinical disorders of acute and chronic GVHR that occur after bone marrow transplantation and autoimmune diseases. A general procedure is described in detail in Current Protocols in Immunology, supra, unit 4.3. In this instance, human PBMCs were purified from leukopack of a normal donor by Ficol gradient. CD8 and NK cell were depleted using MACS CD8 and NK cell depletion kits. 40×10e6 cells were injected into 8-10 week old female SCID Beige mouse on day 0. 100 µg HVEM-Fc or control protein was injected intravenously on day 0, 2, 4, 6, 8, 10. As is shown in FIG. 23, the activation of PRO87299 by HVEM-Fc in a GVHR model significantly prolonged survival. The mice not treated with HVEM-Fc had 100% mortality by day 13 of post-reconstitution. Mice treated with HVEM-Fc lived to day 19 post-reconstitution in one procedure and to day 30 post-reconstitution in another. This result indicates that activation of PRO87299 by an agonist would be useful in tissue transplantation, where administration of a PRO87299 agonist would prevent or alleviate rejection of the transplanted tissue by the host.

Example 20

Deposit of Materials

The following hybridoma cell line has been deposited with the American Type Culture Collection, 10801 University Blvd., Manassas, Va. 20110-2209 USA (ATCC):

| Hybridoma/Antibody Designation | ATCC No. | Deposit Date |
|---|---|---|
| Btig5F5.1 | PTA-6302 | Nov. 11, 2004 |
| Btig3B1.9 | PTA-6301 | Nov. 11, 2004 |

This deposit was made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The cell line will be made available by ATCC under the terms of the Budapest Treaty, and subject to an agreement between Genentech, Inc. and ATCC, which assures (a) that access to the culture will be available during pendency of the patent application to one determined by the Commissioner to be entitled thereto under 37 CFR §1.14 and 35 USC §122, and (b) that all restrictions on the availability to the public of the culture so deposited will be irrevocably removed upon the granting of the patent.

The assignee of the present application has agreed that if the culture on deposit should die or be lost or destroyed when cultivated under suitable conditions, it will be promptly replaced on notification with a viable specimen of the same culture. Availability of the deposited cell line is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the material deposited, since the deposited embodiment is intended as a single illustration of certain aspects of the invention and any constructs that are functionally equivalent are within the scope of this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed:

1. An isolated antibody which specifically binds to the polypeptide of SEQ ID NO:2, wherein said antibody is an agonist antibody that inhibits CD4+ T cell proliferation.

2. The antibody of claim 1, wherein said antibody inhibits lymphoma cell proliferation.

3. The antibody of claim 1, wherein said antibody inhibits NK cell proliferation.

4. The antibody of claim 1, wherein the antibody does not block binding of a polypeptide comprising amino acids 1-199 of SEQ ID NO:4 to a polypeptide comprising amino acids 1-155 of SEQ ID NO:2.

5. The antibody of claim 1, wherein the antibody is a monoclonal antibody.

6. The antibody of claim 1, wherein the antibody is an antibody fragment.

7. The antibody of claim 6, wherein the antibody fragment is a Fab, Fab', F(ab')$_2$, or Fv fragment.

8. The antibody of claim 6, wherein the antibody fragment is a single-chain antibody.

9. The antibody of claim 1, wherein the antibody is a humanized antibody.

10. The antibody of claim 1, wherein the antibody is a human antibody.

11. The isolated antibody of claim 1, wherein the isolated antibody specifically binds to amino acids 1-155 of SEQ ID NO:2.

12. A method of inhibiting CD4+ T cell proliferation, the method comprising exposing CD4+ T cells to the antibody of claim 1.

* * * * *

SEQUENCE LISTING

```
<160> NUMBER OF SEQ ID NOS: 10

<210> SEQ ID NO 1
<211> LENGTH: 1066
<212> TYPE: DNA
<213> ORGANISM: Homo sapiens

<400> SEQUENCE: 1
```

-continued

| | |
|---|---|
| cctcggttct atcgattgaa ttcatgaaga cattgcctgc catgcttgga | 50 |
| actgggaaat tattttgggt cttcttctta atcccatatc tggacatctg | 100 |
| gaacatccat gggaaagaat catgtgatgt acagctttat ataaagagac | 150 |
| aatctgaaca ctccatctta gcaggagatc cctttgaact agaatgccct | 200 |
| gtgaaatact gtgctaacag gcctcatgtg acttggtgca agctcaatgg | 250 |
| aacaacatgt gtaaaacttg aagatagaca acaagttgg aaggaagaga | 300 |
| agaacatttc attttcatt ctacattttg aaccagtgct tcctaatgac | 350 |
| aatgggtcat accgctgttc tgcaaatttt cagtctaatc tcattgaaag | 400 |
| ccactcaaca actctttatg tgacagatgt aaaaagtgct tcagaacgac | 450 |
| cctccaagga cgaaatggca agcagaccct ggctcctgta tagtttactt | 500 |
| cctttggggg gattgcctct actcatcact acctgtttct gcctgttctg | 550 |
| ctgcctgaga aggcaccaag gaaagcaaaa tgaactctct gacacagcag | 600 |
| gaagggaaat taacctggtt gatgctcacc ttaagagtga gcaaacagaa | 650 |
| gcaagcacca ggcaaaattc ccaagtactg ctatcagaaa ctggaattta | 700 |
| tgataatgac cctgaccttt gtttcagaat gcaggaaggg tctgaagttt | 750 |
| attctaatcc atgcctggaa gaaaacaaac caggcattgt ttatgcttcc | 800 |
| ctgaaccatt ctgtcattgg actgaactca agactggcaa gaaatgtaaa | 850 |
| agaagcacca acagaatatg catccatatg tgtgaggagt taaggatcct | 900 |
| ctagagtcga cctgcagaag cttggccgcc atggcccaac ttgtttattg | 950 |
| cagcttataa gtgttacaaa taaacaaata atatttctca atttgagaat | 1000 |
| ttttacttta gaaatgttca tgttagtgct tgggtctgaa gggtccatag | 1050 |
| gacaaatgat taaaat | 1066 |

<210> SEQ ID NO 2
<211> LENGTH: 289
<212> TYPE: PRT
<213> ORGANISM: Homo sapiens

<400> SEQUENCE: 2

Met Lys Thr Leu Pro Ala Met Leu Gly Thr Gly Lys Leu Phe Trp
 1               5                  10                  15

Val Phe Phe Leu Ile Pro Tyr Leu Asp Ile Trp Asn Ile His Gly
                20                  25                  30

Lys Glu Ser Cys Asp Val Gln Leu Tyr Ile Lys Arg Gln Ser Glu
                35                  40                  45

His Ser Ile Leu Ala Gly Asp Pro Phe Glu Leu Glu Cys Pro Val
                50                  55                  60

Lys Tyr Cys Ala Asn Arg Pro His Val Thr Trp Cys Lys Leu Asn
                65                  70                  75

Gly Thr Thr Cys Val Lys Leu Glu Asp Arg Gln Thr Ser Trp Lys
                80                  85                  90

Glu Glu Lys Asn Ile Ser Phe Phe Ile Leu His Phe Glu Pro Val
                95                  100                 105

Leu Pro Asn Asp Asn Gly Ser Tyr Arg Cys Ser Ala Asn Phe Gln
                110                 115                 120

Ser Asn Leu Ile Glu Ser His Ser Thr Thr Leu Tyr Val Thr Asp
                125                 130                 135

Val Lys Ser Ala Ser Glu Arg Pro Ser Lys Asp Glu Met Ala Ser
            140                 145                 150

Arg Pro Trp Leu Leu Tyr Ser Leu Leu Pro Leu Gly Gly Leu Pro
            155                 160                 165

Leu Leu Ile Thr Thr Cys Phe Cys Leu Phe Cys Cys Leu Arg Arg
            170                 175                 180

His Gln Gly Lys Gln Asn Glu Leu Ser Asp Thr Ala Gly Arg Glu
            185                 190                 195

Ile Asn Leu Val Asp Ala His Leu Lys Ser Glu Gln Thr Glu Ala
            200                 205                 210

Ser Thr Arg Gln Asn Ser Gln Val Leu Leu Ser Glu Thr Gly Ile
            215                 220                 225

Tyr Asp Asn Asp Pro Asp Leu Cys Phe Arg Met Gln Glu Gly Ser
            230                 235                 240

Glu Val Tyr Ser Asn Pro Cys Leu Glu Glu Asn Lys Pro Gly Ile
            245                 250                 255

Val Tyr Ala Ser Leu Asn His Ser Val Ile Gly Leu Asn Ser Arg
            260                 265                 270

Leu Ala Arg Asn Val Lys Glu Ala Pro Thr Glu Tyr Ala Ser Ile
            275                 280                 285

Cys Val Arg Ser

<210> SEQ ID NO 3
<211> LENGTH: 1049
<212> TYPE: DNA
<213> ORGANISM: Homo sapiens

<400> SEQUENCE: 3

| | |
|---|---|
| gccgcagcaa tggcgctgag ttcctctgct ggagttcatc ctgctagctg | 50 |
| ggttcccgag ctgccggtct gagcctgagg catggagcct cctggagact | 100 |
| gggggcctcc tccctggaga tccacccca gaaccgacgt cttgaggctg | 150 |
| gtgctgtatc tcaccttcct gggagccccc tgctacgccc agctctgcc | 200 |
| gtcctgcaag gaggacgagt acccagtggg ctccgagtgc tgccccaagt | 250 |
| gcagtccagg ttatcgtgtg aaggaggcct gcggggagct gacgggcaca | 300 |
| gtgtgtgaac cctgccctcc aggcacctac attgcccacc tcaatggcct | 350 |
| aagcaagtgt ctgcagtgcc aaatgtgtga cccagccatg gcctgcgcg | 400 |
| cgagccggaa ctgctccagg acagagaacg ccgtgtgtgg ctgcagccca | 450 |
| ggccacttct gcatcgtcca ggacgggac cactgcgccg cgtgccgcgc | 500 |
| ttacgccacc tccagcccgg gccagagggt gcagaaggga ggcaccgaga | 550 |
| gtcaggacac cctgtgtcag aactgccccc cggggacctt ctctcccaat | 600 |
| gggaccctgg aggaatgtca gcaccagacc aagtgcagct ggctggtgac | 650 |
| gaaggccgga gctgggacca gcagctccca ctgggtatgg tggtttctct | 700 |
| cagggagcct cgtcatcgtc attgtttgct ccacagttgg cctaatcata | 750 |
| tgtgtgaaaa gaagaaagcc aagggtgat gtagtcaagg tgatcgtctc | 800 |
| cgtccagcgg aaaagacagg aggcagaagg tgaggccaca gtcattgagg | 850 |
| ccctgcaggc cctccggac gtcaccacgg tggccgtgga ggagacaata | 900 |
| ccctcattca cggggaggag cccaaaccac tgacccacag actctgcacc | 950 |

```
ccgacgccag agatacctgg agcgacggct gctgaaagag gctgtccacc      1000
tggcgaaacc accggagccc ggaggcttgg gggctccgcc ctgggctgg       1049

<210> SEQ ID NO 4
<211> LENGTH: 283
<212> TYPE: PRT
<213> ORGANISM: Homo sapiens

<400> SEQUENCE: 4

Met Glu Pro Pro Gly Asp Trp Gly Pro Pro Trp Arg Ser Thr
  1               5                  10                  15

Pro Arg Thr Asp Val Leu Arg Leu Val Leu Tyr Leu Thr Phe Leu
             20                  25                  30

Gly Ala Pro Cys Tyr Ala Pro Ala Leu Pro Ser Cys Lys Glu Asp
             35                  40                  45

Glu Tyr Pro Val Gly Ser Glu Cys Cys Pro Lys Cys Ser Pro Gly
             50                  55                  60

Tyr Arg Val Lys Glu Ala Cys Gly Glu Leu Thr Gly Thr Val Cys
             65                  70                  75

Glu Pro Cys Pro Pro Gly Thr Tyr Ile Ala His Leu Asn Gly Leu
             80                  85                  90

Ser Lys Cys Leu Gln Cys Gln Met Cys Asp Pro Ala Met Gly Leu
             95                 100                 105

Arg Ala Ser Arg Asn Cys Ser Arg Thr Glu Asn Ala Val Cys Gly
            110                 115                 120

Cys Ser Pro Gly His Phe Cys Ile Val Gln Asp Gly Asp His Cys
            125                 130                 135

Ala Ala Cys Arg Ala Tyr Ala Thr Ser Ser Pro Gly Gln Arg Val
            140                 145                 150

Gln Lys Gly Gly Thr Glu Ser Gln Asp Thr Leu Cys Gln Asn Cys
            155                 160                 165

Pro Pro Gly Thr Phe Ser Pro Asn Gly Thr Leu Glu Glu Cys Gln
            170                 175                 180

His Gln Thr Lys Cys Ser Trp Leu Val Thr Lys Ala Gly Ala Gly
            185                 190                 195

Thr Ser Ser Ser His Trp Val Trp Trp Phe Leu Ser Gly Ser Leu
            200                 205                 210

Val Ile Val Ile Val Cys Ser Thr Val Gly Leu Ile Ile Cys Val
            215                 220                 225

Lys Arg Arg Lys Pro Arg Gly Asp Val Lys Val Ile Val Ser
            230                 235                 240

Val Gln Arg Lys Arg Gln Glu Ala Glu Gly Glu Ala Thr Val Ile
            245                 250                 255

Glu Ala Leu Gln Ala Pro Pro Asp Val Thr Thr Val Ala Val Glu
            260                 265                 270

Glu Thr Ile Pro Ser Phe Thr Gly Arg Ser Pro Asn His
            275                 280

<210> SEQ ID NO 5
<211> LENGTH: 1159
<212> TYPE: DNA
<213> ORGANISM: Homo sapiens

<400> SEQUENCE: 5
ggtttcctct gaggttgaag gacccaggcg tgtcagccct gctccagaca       50
```

-continued

| | |
|---|---|
| ccttgggcat ggaggagagt gtcgtacggc cctcagtgtt tgtggtggat | 100 |
| ggacagaccg acatcccatt cacgaggctg ggacgaagcc accggagaca | 150 |
| gtcgtgcagt gtggcccggg tgggtctggg tctcttgctg ttgctgatgg | 200 |
| gggccgggct ggccgtccaa ggctggttcc tcctgcagct gcactggcgt | 250 |
| ctaggagaga tggtcacccg cctgcctgac ggacctgcag gctcctggga | 300 |
| gcagctgata caagagcgaa ggtctcacga ggtcaaccca gcagcgcatc | 350 |
| tcacaggggc caactccagc ttgaccggca gcggggggcc gctgttatgg | 400 |
| gagactcagc tgggcctggc cttcctgagg ggcctcagct accacgatgg | 450 |
| ggcccttgtg gtcaccaaag ctggctacta ctacatctac tccaaggtgc | 500 |
| agctgggcgt gtgggctgc ccgctgggcc tggccagcac catcacccac | 550 |
| ggcctctaca gcgcacacc ccgctacccc gaggagctgg agctgttggt | 600 |
| cagccagcag tcaccctgcg gacgggccac cagcagctcc cgggtctggt | 650 |
| gggacagcag cttcctgggt ggtgtggtac acctggaggc tggggaggag | 700 |
| gtggtcgtcc gtgtgctgga tgaacgcctg gttcgactgc gtgatggtac | 750 |
| ccggtcttac ttcggggctt tcatggtgtg aaggaaggag cgtggtgcat | 800 |
| tggacatggg tctgacacgt ggagaactca gagggtgcct caggggaaag | 850 |
| aaaactcacg aagcagaggc tgggcgtggt ggctctcgcc tgtaatccca | 900 |
| gcactttggg aggccaaggc aggcggatca cctgaggtca ggagttcgag | 950 |
| accagcctgg ctaacatggc aaaaccccat ctctactaaa aatacaaaaa | 1000 |
| ttagccggac gtggtggtgc ctgcctgtaa tccagctact caggaggctg | 1050 |
| aggcaggata attttgctta aacccgggag gcggaggttg cagtgagccg | 1100 |
| agatcacacc actgcactcc aacctgggaa acgcagtgag actgtgcctc | 1150 |
| aaaaaaaag | 1159 |

<210> SEQ ID NO 6
<211> LENGTH: 240
<212> TYPE: PRT
<213> ORGANISM: Homo sapiens

<400> SEQUENCE: 6

```
Met Glu Glu Ser Val Val Arg Pro Ser Val Phe Val Val Asp Gly
  1               5                  10                  15

Gln Thr Asp Ile Pro Phe Thr Arg Leu Gly Arg Ser His Arg Arg
                 20                  25                  30

Gln Ser Cys Ser Val Ala Arg Val Gly Leu Gly Leu Leu Leu Leu
                 35                  40                  45

Leu Met Gly Ala Gly Leu Ala Val Gln Gly Trp Phe Leu Leu Gln
                 50                  55                  60

Leu His Trp Arg Leu Gly Glu Met Val Thr Arg Leu Pro Asp Gly
                 65                  70                  75

Pro Ala Gly Ser Trp Glu Gln Leu Ile Gln Glu Arg Arg Ser His
                 80                  85                  90

Glu Val Asn Pro Ala Ala His Leu Thr Gly Ala Asn Ser Ser Leu
                 95                 100                 105

Thr Gly Ser Gly Gly Pro Leu Leu Trp Glu Thr Gln Leu Gly Leu
                110                 115                 120

Ala Phe Leu Arg Gly Leu Ser Tyr His Asp Gly Ala Leu Val Val
```

```
                125                 130                 135
Thr Lys Ala Gly Tyr Tyr Tyr Ile Tyr Ser Lys Val Gln Leu Gly
            140                 145                 150
Gly Val Gly Cys Pro Leu Gly Leu Ala Ser Thr Ile Thr His Gly
            155                 160                 165
Leu Tyr Lys Arg Thr Pro Arg Tyr Pro Glu Glu Leu Glu Leu Leu
            170                 175                 180
Val Ser Gln Gln Ser Pro Cys Gly Arg Ala Thr Ser Ser Ser Arg
            185                 190                 195
Val Trp Trp Asp Ser Ser Phe Leu Gly Gly Val Val His Leu Glu
            200                 205                 210
Ala Gly Glu Glu Val Val Val Arg Val Leu Asp Glu Arg Leu Val
            215                 220                 225
Arg Leu Arg Asp Gly Thr Arg Ser Tyr Phe Gly Ala Phe Met Val
            230                 235                 240
```

<210> SEQ ID NO 7
<211> LENGTH: 726
<212> TYPE: DNA
<213> ORGANISM: Homo sapiens

<400> SEQUENCE: 7

```
atgaagacat tgcctgccat gcttggaact gggaaattat tttgggtctt         50
cttcttaatc ccatatctgg acatctggaa catccatggg aaagaatcat        100
gtgatgtaca gctttatata agagacaat ctgaacactc catcttagca         150
ggagatccct ttgaactaga atgccctgtg aaatactgtg ctaacaggcc        200
tcatgtgact tggtgcaagc tcaatggaac aacatgtgta aaacttgaag        250
atagacaaac aagttggaag gaagagaaga acatttcatt tttcattcta        300
cattttgaac cagtgcttcc taatgacaat gggtcatacc gctgttctgc        350
aaatttcag tctaatctca ttgaaagcca ctcaacaact ctttatgtga         400
caggaaagca aaatgaactc tctgacacag caggaaggga aattaacctg        450
gttgatgctc accttaagag tgagcaaaca gaagcaagca ccaggcaaaa        500
ttcccaagta ctgctatcag aaactggaat ttatgataat gaccctgacc        550
tttgtttcag gatgcaggaa gggtctgaag tttattctaa tccatgcctg        600
gaagaaaaca aaccaggcat tgtttatgct tccctgaacc attctgtcat        650
tggactgaac tcaagactgg caagaaatgt aaaagaagca ccaacagaat        700
atgcatccat atgtgtgagg agttaa                                  726
```

<210> SEQ ID NO 8
<211> LENGTH: 241
<212> TYPE: PRT
<213> ORGANISM: Homo sapiens

<400> SEQUENCE: 8

```
Met Lys Thr Leu Pro Ala Met Leu Gly Thr Gly Lys Leu Phe Trp
  1               5                  10                  15
Val Phe Phe Leu Ile Pro Tyr Leu Asp Ile Trp Asn Ile His Gly
                 20                  25                  30
Lys Glu Ser Cys Asp Val Gln Leu Tyr Ile Lys Arg Gln Ser Glu
                 35                  40                  45
His Ser Ile Leu Ala Gly Asp Pro Phe Glu Leu Glu Cys Pro Val
```

```
                  50                  55                  60
Lys Tyr Cys Ala Asn Arg Pro His Val Thr Trp Cys Lys Leu Asn
             65                  70                  75
Gly Thr Thr Cys Val Lys Leu Glu Asp Arg Gln Thr Ser Trp Lys
         80                  85                  90
Glu Glu Lys Asn Ile Ser Phe Phe Ile Leu His Phe Glu Pro Val
     95                  100                 105
Leu Pro Asn Asp Asn Gly Ser Tyr Arg Cys Ser Ala Asn Phe Gln
                 110                 115                 120
Ser Asn Leu Ile Glu Ser His Ser Thr Thr Leu Tyr Val Thr Gly
             125                 130                 135
Lys Gln Asn Glu Leu Ser Asp Thr Ala Gly Arg Glu Ile Asn Leu
         140                 145                 150
Val Asp Ala His Leu Lys Ser Glu Gln Thr Glu Ala Ser Thr Arg
     155                 160                 165
Gln Asn Ser Gln Val Leu Leu Ser Glu Thr Gly Ile Tyr Asp Asn
                 170                 175                 180
Asp Pro Asp Leu Cys Phe Arg Met Gln Glu Gly Ser Glu Val Tyr
             185                 190                 195
Ser Asn Pro Cys Leu Glu Glu Asn Lys Pro Gly Ile Val Tyr Ala
         200                 205                 210
Ser Leu Asn His Ser Val Ile Gly Leu Asn Ser Arg Leu Ala Arg
     215                 220                 225
Asn Val Lys Glu Ala Pro Thr Glu Tyr Ala Ser Ile Cys Val Arg
                 230                 235                 240
Ser
```

<210> SEQ ID NO 9
<211> LENGTH: 888
<212> TYPE: DNA
<213> ORGANISM: Homo sapiens

<400> SEQUENCE: 9

| | |
|---|---|
| atgaagacat tgcctgccat gcttggaact gggaaattat tttgggtctt | 50 |
| cttcttaatc ccatatctgg acatctggaa catccatggg aaagaatcat | 100 |
| gtgatgtaca gctttatata aagagacaat ctgaacactc catcttagca | 150 |
| ggagatccct ttgaactaga atgccctgtg aaatactgtg ctaacaggcc | 200 |
| tcatgtgact tggtgcaagc tcaatggaac aacatgtgta aaacttgaag | 250 |
| atagacaaac aagttggaag gaagagaaga acatttcatt tttcattcta | 300 |
| cattttgaac cagtgcttcc taatgacaat gggtcatacc gctgttctgc | 350 |
| aaattttcag tctaatctca ttgaaagcca ctcaacaact ctttatgtga | 400 |
| cagcatttac taacattcca gatgtaaaaa gtgcctcaga acgaccctcc | 450 |
| aaggacgaaa tggcaagcag accctggctc ctgtatagtt tacttccttt | 500 |
| gggggattg cctctactca tcactacctg tttctgcctg ttctgctgcc | 550 |
| tgagaaggca ccaaggaaag caaatgaac tctctgacac agcaggaagg | 600 |
| gaaattaacc tggttgatgc tcaccttaag agtgagcaaa cagaagcaag | 650 |
| caccaggcaa aattcccaag tactgctatc agaaactgga atttatgata | 700 |
| atgaccctga cctttgtttc aggatgcagg aagggtctga agtttattct | 750 |
| aatccatgcc tggaagaaaa caaaccaggc attgtttatg cttccctgaa | 800 |

```
ccattctgtc attggactga actcaagact ggcaagaaat gtaaaagaag          850
caccaacaga atatgcatcc atatgtgtga ggagttaa                       888
```

<210> SEQ ID NO 10
<211> LENGTH: 295
<212> TYPE: PRT
<213> ORGANISM: Homo sapiens

<400> SEQUENCE: 10

```
Met Lys Thr Leu Pro Ala Met Leu Gly Thr Gly Lys Leu Phe Trp
 1               5                  10                  15

Val Phe Phe Leu Ile Pro Tyr Leu Asp Ile Trp Asn Ile His Gly
                20                  25                  30

Lys Glu Ser Cys Asp Val Gln Leu Tyr Ile Lys Arg Gln Ser Glu
                35                  40                  45

His Ser Ile Leu Ala Gly Asp Pro Phe Glu Leu Glu Cys Pro Val
                50                  55                  60

Lys Tyr Cys Ala Asn Arg Pro His Val Thr Trp Cys Lys Leu Asn
                65                  70                  75

Gly Thr Thr Cys Val Lys Leu Glu Asp Arg Gln Thr Ser Trp Lys
                80                  85                  90

Glu Glu Lys Asn Ile Ser Phe Phe Ile Leu His Phe Glu Pro Val
                95                 100                 105

Leu Pro Asn Asp Asn Gly Ser Tyr Arg Cys Ser Ala Asn Phe Gln
               110                 115                 120

Ser Asn Leu Ile Glu Ser His Ser Thr Thr Leu Tyr Val Thr Ala
               125                 130                 135

Phe Thr Asn Ile Pro Asp Val Lys Ser Ala Ser Glu Arg Pro Ser
               140                 145                 150

Lys Asp Glu Met Ala Ser Arg Pro Trp Leu Leu Tyr Ser Leu Leu
               155                 160                 165

Pro Leu Gly Gly Leu Pro Leu Leu Ile Thr Thr Cys Phe Cys Leu
               170                 175                 180

Phe Cys Cys Leu Arg Arg His Gln Gly Lys Gln Asn Glu Leu Ser
               185                 190                 195

Asp Thr Ala Gly Arg Glu Ile Asn Leu Val Asp Ala His Leu Lys
               200                 205                 210

Ser Glu Gln Thr Glu Ala Ser Thr Arg Gln Asn Ser Gln Val Leu
               215                 220                 225

Leu Ser Glu Thr Gly Ile Tyr Asp Asn Asp Pro Asp Leu Cys Phe
               230                 235                 240

Arg Met Gln Glu Gly Ser Glu Val Tyr Ser Asn Pro Cys Leu Glu
               245                 250                 255

Glu Asn Lys Pro Gly Ile Val Tyr Ala Ser Leu Asn His Ser Val
               260                 265                 270

Ile Gly Leu Asn Ser Arg Leu Ala Arg Asn Val Lys Glu Ala Pro
               275                 280                 285

Thr Glu Tyr Ala Ser Ile Cys Val Arg Ser
               290                 295
```